US011517572B2

(12) United States Patent
Kirkland et al.

(10) Patent No.: US 11,517,572 B2
(45) Date of Patent: Dec. 6, 2022

(54) KILLING SENESCENT CELLS AND TREATING SENESCENCE-ASSOCIATED CONDITIONS USING A SRC INHIBITOR AND A FLAVONOID

(71) Applicant: Mayo Foundation for Medical Education and Research, Rochester, MN (US)

(72) Inventors: James L. Kirkland, Rochester, MN (US); Tamar Tchkonia, Rochester, MN (US); Yi Zhu, Rochester, MN (US); Allyson K. Palmer, Rochester, MN (US); Nathan K. LeBrasseur, Rochester, MN (US); Jordan D. Miller, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 16/865,179

(22) Filed: May 1, 2020

(65) Prior Publication Data
US 2020/0316066 A1 Oct. 8, 2020

Related U.S. Application Data

(63) Continuation of application No. 15/113,723, filed as application No. PCT/US2015/013376 on Jan. 28, 2015, now abandoned.

(60) Provisional application No. 61/932,711, filed on Jan. 28, 2014, provisional application No. 61/932,704, filed on Jan. 28, 2014.

(51) Int. Cl.
| | | |
|---|---|---|
| A61K 31/506 | (2006.01) | |
| A61K 31/352 | (2006.01) | |
| A61K 31/7048 | (2006.01) | |
| A61K 45/06 | (2006.01) | |
| A61K 31/353 | (2006.01) | |
| A61K 31/665 | (2006.01) | |

(52) U.S. Cl.
CPC .......... *A61K 31/506* (2013.01); *A61K 31/352* (2013.01); *A61K 31/353* (2013.01); *A61K 31/665* (2013.01); *A61K 31/7048* (2013.01); *A61K 45/06* (2013.01)

(58) Field of Classification Search
CPC .. A61K 31/506; A61K 31/352; A61K 31/353; A61K 31/665; A61K 31/7048; A61K 45/06
USPC ........................................................ 514/35
See application file for complete search history.

(56) References Cited

U.S. PATENT DOCUMENTS

| | | |
|---|---|---|
| 5,668,152 A | 9/1997 | Heath, Jr. et al. |
| 6,596,746 B1 | 7/2003 | Das et al. |
| 6,617,346 B1 | 9/2003 | Kong et al. |
| 6,664,443 B1 | 12/2003 | Hutton et al. |
| 6,734,302 B2 | 5/2004 | Kong et al. |
| 7,125,875 B2 | 10/2006 | Das et al. |
| 7,153,856 B2 | 12/2006 | Banish et al. |
| 7,482,134 B2 | 1/2009 | Jang et al. |
| 7,491,725 B2 | 2/2009 | Lajeunesse et al. |
| 7,705,007 B2 | 4/2010 | Fotouhi et al. |
| 7,767,684 B2 | 8/2010 | Bruncko et al. |
| 7,842,681 B2 | 11/2010 | Elmore et al. |
| 7,851,626 B2 | 12/2010 | Ding et al. |
| 7,893,278 B2 | 2/2011 | Haley et al. |
| 8,114,893 B2 | 2/2012 | Baell et al. |
| 8,168,645 B2 | 5/2012 | Baell et al. |
| 8,168,784 B2 | 5/2012 | Franczyk, II et al. |
| 8,343,967 B2 | 1/2013 | Ding et al. |
| 8,426,422 B2 | 4/2013 | Hexamer et al. |
| 8,563,735 B2 | 10/2013 | Bruncko et al. |
| 8,586,754 B2 | 11/2013 | Bruncko et al. |
| 8,691,184 B2 | 4/2014 | Wang et al. |
| 9,018,381 B2 | 4/2015 | Diebold et al. |
| 9,248,140 B2 | 2/2016 | Diebold et al. |
| 9,266,860 B2 | 2/2016 | Guy et al. |
| 9,360,471 B2 | 6/2016 | Qi |
| 9,527,847 B2 | 12/2016 | Palombella et al. |
| 9,630,990 B2 | 4/2017 | Shetty et al. |
| 9,993,472 B2 | 6/2018 | Laberge et al. |
| 10,328,058 B2 | 6/2019 | Baker et al. |
| 2002/0054915 A1 | 5/2002 | Goldenheim et al. |
| 2002/0197602 A1 | 12/2002 | Burmer et al. |

(Continued)

FOREIGN PATENT DOCUMENTS

| | | |
|---|---|---|
| CN | 101528223 A | 9/2009 |
| CN | 101641338 A | 2/2010 |

(Continued)

OTHER PUBLICATIONS

Glossary of medical education terms, Institute of International Medical Education. http://www.iime.org/glossary.htm Accessed in Mar. 2013. (Year: 2013).*

(Continued)

*Primary Examiner* — Yih-Horng Shiao
(74) *Attorney, Agent, or Firm* — Fish & Richardson P.C.

(57) ABSTRACT

Provided herein are methods and uses for treatment or prophylaxis of a senescent cell associated disease or disorder by administering a senolytic combination comprising dasatinib and quercetin or an analog thereof to a subject in need thereof. In certain embodiments, the senescent cell associated disease or disorder is a cardiovascular disease or disorder, inflammatory disease or disorder, a pulmonary disease or disorder, a neurological disease or disorder, or a metabolic disease or disorder.

3 Claims, 41 Drawing Sheets

(56) References Cited

U.S. PATENT DOCUMENTS

| | | |
|---|---|---|
| 2003/0086916 A1 | 5/2003 | Goligorsky et al. |
| 2003/0157028 A1 | 8/2003 | Lewis et al. |
| 2004/0242545 A1 | 12/2004 | Otsuka et al. |
| 2005/0019865 A1 | 1/2005 | Kihm et al. |
| 2005/0181076 A1 | 8/2005 | Ziegler |
| 2005/0282803 A1 | 12/2005 | Haley et al. |
| 2006/0122150 A1 | 6/2006 | Argentieri et al. |
| 2006/0182781 A1 | 8/2006 | Hughes et al. |
| 2007/0027135 A1 | 2/2007 | Bruncko et al. |
| 2007/0129416 A1 | 6/2007 | Ding et al. |
| 2007/0292475 A1 | 12/2007 | Campbell et al. |
| 2008/0221132 A1 | 9/2008 | Cai et al. |
| 2008/0234362 A1 | 9/2008 | Chandler |
| 2009/0068155 A1 | 3/2009 | Frey, II et al. |
| 2009/0105319 A1 | 4/2009 | Pellecchia et al. |
| 2010/0016218 A1 | 1/2010 | Lighter et al. |
| 2010/0087436 A1 | 4/2010 | Bardwell et al. |
| 2010/0093648 A1 | 4/2010 | Cruz |
| 2010/0152183 A1 | 6/2010 | Bruncko et al. |
| 2010/0227838 A1 | 9/2010 | Shah et al. |
| 2010/0292200 A1 | 11/2010 | Kile et al. |
| 2010/0310504 A1 | 12/2010 | Lowe et al. |
| 2011/0027177 A1 | 2/2011 | Jacoby et al. |
| 2011/0028437 A1 | 2/2011 | Robbins et al. |
| 2011/0070184 A1 | 3/2011 | Bernhagen et al. |
| 2011/0071151 A1 | 3/2011 | Zhang et al. |
| 2011/0212909 A1 | 9/2011 | Wen et al. |
| 2011/0218206 A1 | 9/2011 | Chan |
| 2012/0005765 A1 | 1/2012 | Kumar et al. |
| 2012/0028925 A1 | 2/2012 | Tao et al. |
| 2012/0035134 A1 | 2/2012 | Diebold et al. |
| 2012/0046333 A1 | 2/2012 | Hardie et al. |
| 2012/0071468 A1 | 5/2012 | John et al. |
| 2012/0108590 A1 | 5/2012 | Birtalan et al. |
| 2012/0115880 A1 | 5/2012 | Dyer et al. |
| 2012/0129853 A1 | 5/2012 | Elmore et al. |
| 2012/0156134 A1 | 6/2012 | Squires |
| 2012/0156197 A1 | 6/2012 | Errico et al. |
| 2012/0183534 A1 | 7/2012 | Gruber |
| 2012/0189539 A1 | 7/2012 | Wang et al. |
| 2012/0276093 A1 | 11/2012 | Ballinari et al. |
| 2012/0277210 A1 | 11/2012 | Catron et al. |
| 2012/0283269 A1 | 11/2012 | Blagosklonny et al. |
| 2013/0096121 A1 | 4/2013 | Wang et al. |
| 2013/0149314 A1 | 6/2013 | Bullerdiek et al. |
| 2013/0225594 A1 | 8/2013 | Craighead et al. |
| 2013/0225603 A1 | 8/2013 | Chavala et al. |
| 2013/0267534 A1 | 10/2013 | Bruncko et al. |
| 2013/0287763 A1 | 10/2013 | Sathyanarayanan et al. |
| 2013/0302283 A1 | 11/2013 | Kihm |
| 2013/0317043 A1 | 11/2013 | Wagner et al. |
| 2014/0005190 A1 | 1/2014 | Baell et al. |
| 2014/0017341 A1 | 1/2014 | Gourlaouen |
| 2014/0018302 A1 | 1/2014 | Walensky et al. |
| 2014/0073640 A1 | 3/2014 | Judd et al. |
| 2014/0100366 A1 | 4/2014 | Babu et al. |
| 2014/0134163 A1 | 5/2014 | Errico et al. |
| 2014/0220111 A1 | 8/2014 | Hayes et al. |
| 2014/0242545 A1 | 8/2014 | Brun et al. |
| 2014/0256721 A1 | 9/2014 | Hamblin et al. |
| 2014/0272947 A1 | 9/2014 | Zhang et al. |
| 2014/0275082 A1 | 9/2014 | Tao et al. |
| 2014/0328893 A1 | 11/2014 | Adnot |
| 2015/0051215 A1 | 2/2015 | Wooster et al. |
| 2015/0126573 A1 | 5/2015 | Boczkowski et al. |
| 2015/0140036 A1 | 5/2015 | Mannick et al. |
| 2015/0231136 A1 | 8/2015 | Chavala et al. |
| 2016/0000744 A1 | 1/2016 | Day et al. |
| 2016/0022720 A1 | 1/2016 | Jordan |
| 2016/0122758 A1 | 5/2016 | Krizhanovsky et al. |
| 2017/0056421 A1 | 3/2017 | Zhou et al. |
| 2017/0119789 A1 | 5/2017 | Campisi et al. |
| 2017/0216286 A1 | 8/2017 | Kirkland et al. |
| 2017/0266211 A1 | 9/2017 | David et al. |
| 2018/0000816 A1 | 1/2018 | David et al. |
| 2018/0104222 A1 | 4/2018 | Childs |
| 2019/0000846 A1 | 1/2019 | Van Deursen et al. |
| 2019/0175623 A1 | 6/2019 | Laberge |
| 2019/0269675 A1 | 9/2019 | Chinta et al. |

FOREIGN PATENT DOCUMENTS

| | | |
|---|---|---|
| CN | 101679382 A | 3/2010 |
| EP | 3099380 A1 | 12/2016 |
| EP | 3139942 A1 | 3/2017 |
| KR | 20120118596 A | 10/2012 |
| KR | 20130139512 A | 12/2013 |
| RU | 2358734 C2 | 6/2009 |
| WO | WO-0164717 A1 | 9/2001 |
| WO | WO-03028443 A1 | 4/2003 |
| WO | WO-03051359 A1 | 6/2003 |
| WO | WO-2006018632 A2 | 2/2006 |
| WO | WO-2006039704 A2 | 4/2006 |
| WO | WO-2008014216 A1 | 1/2008 |
| WO | WO-2008106507 A2 | 9/2008 |
| WO | WO-2008113131 A1 | 9/2008 |
| WO | WO-2008125487 A1 | 10/2008 |
| WO | WO-2009039553 A1 | 4/2009 |
| WO | WO-2009105234 A2 | 8/2009 |
| WO | WO-2009151069 A1 | 12/2009 |
| WO | WO-2010080478 A1 | 7/2010 |
| WO | WO-2010148447 A1 | 12/2010 |
| WO | WO-2011056961 A2 | 5/2011 |
| WO | WO-2011068560 A1 | 6/2011 |
| WO | WO-2011083150 A2 | 7/2011 |
| WO | WO-2012103524 A2 | 8/2012 |
| WO | WO-2012105707 A1 | 8/2012 |
| WO | WO-2012120048 A1 | 9/2012 |
| WO | WO 2012/177927 | 12/2012 |
| WO | WO 2013/090645 | 6/2013 |
| WO | WO 2013/155077 | * 10/2013 |
| WO | WO-2014145389 A1 | 9/2014 |
| WO | WO-2014186878 A1 | 11/2014 |
| WO | WO 2014/205244 | 12/2014 |
| WO | WO-2015051252 A1 | 4/2015 |
| WO | WO-2015066442 A1 | 5/2015 |
| WO | WO-2015116735 A1 | 8/2015 |
| WO | WO-2015116740 A1 | 8/2015 |
| WO | WO-2015181526 A1 | 12/2015 |

OTHER PUBLICATIONS

Schafer et al. Cellular senescence mediates fibrotic pulmonary disease. Nature Communications 8:14532, 2017, DOI: 10.1038/ncomms14532 (Year: 2017).*

Day et al. Inhibition of collagen-induced discoidin domain receptor 1 and 2 activation by imatinib, nilotinib and dasatinib. European Journal of Pharmacology 599 (2008) 44-53. (Year: 2008).*

Nakamura et al. Attenuation of Transforming Growth Factor-ß-Stimulated Collagen Production in Fibroblasts by Quercetin-Induced Heme Oxygenase-1. Am J Respir Cell Mol Biol vol. 44. pp 614-620, 2011. (Year: 2011).*

Axanova, Linara S. et al. 1,25-Dihydroxyvitamin D3 and PI3K/AKT Inhibitors Synergistically Inhibit Growth and Induce Senescence in Prostate Cancer Cells. Prostate. 70(15):1658-1671 (Nov. 1, 2010).

Bai, et al. BM-1197: a novel and specific Bcl-2/Bcl-xL inhibitor inducing complete and long-lasting tumor regression in vivo. PLoS One. Jun. 5, 2014;9(6):e99404. 13 pages.

Chand et al. A Small Molecule Bcl-2 Inhibitor Switches Il-13 to a Cell Death Inducer for Allergen-Induced Metaplastic Mucous Cells. Am J Respir Crit Care Med 189 (2014): A2049 (poster session May 18, 2014).

Chappell, William H. Ras/Raf/MEK/ERK and PI3K/PTEN/Akt/mTOR inhibitors: rationale and importance to inhibiting these pathways in human health. Oncotarget. Mar. 2011;2(3):135-64.

Collado et al. Inhibition of the phosphoinositide 3-kinase pathway induces a senescence-like arrest mediated by p27Kip1. J Biol Chem 275(29):21960-21968 (Jul. 21, 2000). First published Apr. 28, 2000.

Demidenko et al. Paradoxical suppression of cellular senescence by p53. PNAS 107(21):9660-9664 (May 10, 2010).

(56) References Cited

OTHER PUBLICATIONS

Dienstmann, Rodrigo et al. Picking the point of inhibition: a comparative review of PI3K/AKT/mTOR pathway inhibitors. Mol Cancer Ther. May 2014;13(5):1021-31. Epub Apr. 18, 2014.
EP15743068.7 Office Action dated Mar. 13, 2019.
EP15743068.7 Office Action dated Nov. 28, 2019.
EP19216214.7 Extended European Search Report dated May 28, 2020.
Gorenne, et al. Vascular smooth muscle cell senescence in atherosclerosis. Cardiovasc Res. Oct. 1, 2006 ;72(1):9-17. Epub Jun. 6, 2006.
Hartung et al. Resolution of Apoptosis in Atherosclerotic Plaque by Dietary Modification and Statin Therapy. J Nucl Med 46(12):2051-2056 (Dec. 2005).
Hashimoto, T. et al. Inhibition of MDM2 attenuates neointimal hyperplasia via suppression of vascular proliferation and inflammation. Cardiovascular Research, 91(4):711-719 (Sep. 1, 2011) [E-Pub Apr. 14, 2011].
Ihling, C. et al. Co-Expression of p53 and MDM2 in Human Atherosclerosis: Implications for the Regulation of Cellularity for the Regulation of Atherosclerotic lesions. Journal of Pathology, 185(3):303-312 (Jul. 1998).
Kegel, Magdalena. Cancer Drug Candidate to Be Tested on Lung Fibrosis in Phase 1 Clinical Trial. Pulmonary Fibrosis News. pp. 1-2 (May 2, 2016).
Kutuk et al. Bcl-2 protein family: Implications in vascular apoptosis and atherosclerosis. Apoptosis 11(10):1661-1675 (Aug. 24, 2006).
Lazo et al. Pharmacologic profiling of phosphoinositide 3-kinase inhibitors as mitigators of ionizing radiation-induced cell death. J Pharmacol Exp Ther 347(3):669-80 (2013).
Le Cras, Timothy D. et al. Inhibition of PI3K by PX-866 Prevents Transforming Growth Factor-α-Induced Pulmonary Fibrosis, Am J Pathol. Feb. 2010;176(2):679-86. Epub Dec. 30, 2009.
Lessene et al. Structure-guided Design of a Selective BCL-X(L) Inhibitor. Nat Chem Biol Actions. Jun. 2013;9(6):390-7.doi: 10.1038/nchembio.1246. Epub Apr. 21, 2013.
Liu, Shuang et al. The PI3K-Akt pathway inhibits senescence and promotes self-renewal of human skin-derived precursors in vitro. Aging Cell. Aug. 2011;10(4):661-74. Epub May 3, 2011 .
Markman et al. Targeting the PI3K/Akt/mTOR Pathway—Beyond Rapalogs. Oncotarget 1(7):530-543 (Oct. 22, 2010).
Mehta et al. Studies of Apoptosis and bcl-2 in Experimental Atherosclerosis in Rabbit and Influence of Selenium Supplementation. Gen Physiol Biophys 21:125-29 (Mar. 1, 2002).
Mercer et al. Endogenous p53 Protects Vascular Smooth Muscle Cells From Apoptosis and Reduces Atherosclerosis in ApoE Knockout Mice. Circulation Research 96(6):667-674 (Mar. 3, 2005).
Minamino et al. Endothelial Cell Senescence in Human Atherosclerosis. Circulation 105(13):1541-1544 (Mar. 18, 2002).
Munoz-Espin et al. Cellular senescence: from physiology to pathology. Nat Rev Mol Cell Biol 15(7):482-496 (Jun. 23, 2014).
Shen et al. Introduction to p53 and mdm2. China Tropical Medicine, Issue 1, pp. 103-105 (2007).
Silvestre-Roig et al. Atherosclerotic Plaque Destabilization. Circulation Research 114(1):214-226 (Jan. 3, 2014).
Tanaka et al. Discovery of Potent Mcl-1/Bcl-xL Dual Inhibitors by Using a Hybridization Strategy Based on Structural Analysis of Target Proteins. Journal of Medicinal Chemistry 56(23):9635-9645 (Nov. 11, 2013).
Tchkonia, et al. Cellular senescence and the senescent secretory phenotype: therapeutic opportunities. J Clin Invest. Mar. 2013;123(3):966-72. doi: 10.1172/JCI64098. Epub Mar. 1, 2013.
U.S. Appl. No. 15/113,723 Final Office Action dated Feb. 19, 2019.
U.S. Appl. No. 15/113,723 Non-Final Office Action dated Jul. 26, 2018.
U.S. Appl. No. 15/455,684 Notice of Allowance dated Oct. 31, 2018.
U.S. Appl. No. 15/792,593 Final Office Action dated Jan. 8, 2019.
U.S. Appl. No. 15/792,593 Notice of Allowance dated Feb. 14, 2019.
U.S. Appl. No. 15/792,593 Pre-Interview Office Action dated Sep. 20, 2018.
U.S. Appl. No. 15/950,965 Final Office Action dated Apr. 24, 2019.
U.S. Appl. No. 15/950,965. First Action Interview Pilot Program Pre-Interview Communication dated Dec. 21, 2018.
U.S. Appl. No. 15/955,542 Notice of Allowance dated Dec. 5, 2018.
U.S. Appl. No. 15/956,613 First Action Interview Office Action Summary dated Apr. 4, 2019.
U.S. Appl. No. 15/956,613 Pre-Interview Office Action dated Jan. 15, 2019.
U.S. Appl. No. 15/981,696 Non-Final Office Action dated Apr. 22, 2019.
U.S. Appl. No. 15/981,696 Pre-Interview Office Action dated Jan. 17, 2019.
U.S. Appl. No. 16/007,880 Non-Final Office Action dated Mar. 15, 2019.
U.S. Appl. No. 16/054,667 Final Office Action dated Mar. 1, 2019.
U.S. Appl. No. 16/054,667 Notice of Allowance dated Mar. 28, 2019.
U.S. Appl. No. 16/054,667 Pre Office Action Interview Response dated Nov. 20, 2018.
U.S. Appl. No. 15/455,630 Office Action dated Nov. 15, 2019.
U.S. Appl. No. 15/950,965 Notice of Allowance dated Jul. 3, 2019.
U.S. Appl. No. 15/956,613 Notice of Allowance dated Aug. 28, 2019.
U.S. Appl. No. 15/956,613 Office Action dated Jul. 29, 2019.
U.S. Appl. No. 15/981,696 Notice of Allowance dated Oct. 8, 2019.
U.S. Appl. No. 16/007,880 Office Action dated Aug. 9, 2019.
U.S. Appl. No. 16/025,238 First Action Interview Pilot Program Pre-Interview Communication dated Apr. 9, 2019.
U.S. Appl. No. 16/025,238 Office Action dated Sep. 9, 2019.
U.S. Appl. No. 15/455,630 Office Action dated Aug. 9, 2019.
U.S. Appl. No. 16/007,880 Notice of Allowance dated Sep. 18, 2019.
U.S. Appl. No. 16/403,389 First Action Interview Office Action Summary dated May 18, 2020.
U.S. Appl. No. 16/403,389 First Action Interview Pilot Program Pre-Interview Communication dated Mar. 23, 2020.
Verheye et al. Selective clearance of macrophages in atherosclerotic plaques by autophagy. J Ann Coll Cardiol. 49(6):706-15 (2007).
Wang et al. Interferon-gamma induces human vascular smooth muscle cell proliferation and intimal expansion by phosphatidylinositol 3-kinase dependent mammalian target of rapamycin raptor complex 1 activation. Circ Res. 101(6 ):560-9 (2007).
Wang et al. Aging and atherosclerosis: mechanisms, functional consequences, and potential therapeutics for cellular senescence. Circ Res. 111(2):245-259 (Jul. 6, 2012).
Wang et al. Effects of rapamycin on expression of Bcl-2 and Bax in human lens epithelial cells and cell cycle in rats. J Huazhong Univ Sci Technol [Med Sci] 31(4):555-559 (2011).
Wang et al. Vascular Smooth Muscle Cell Senescence Promotes Atherosclerosis and Features of Plaque Vulnerability. Circulation 32(20):1909-1919 (Nov. 17, 2015). Epub Sep. 28, 2015.
Weber et al. Atherosclerosis: current pathogenesis and therapeutic options. Nature Medicine vol. 17:1410-1422 (Nov. 7, 2011).
Wouters et al. Bone Marrow p16INK4a—Deficiency Does Not Modulate Obesity, Glucose Homeostasis or Atherosclerosis Development. PLoS ONE 7(3): e32440 (Mar. 2012). 9 pages.
Zhai et al. Selective inhibition of PI3K/Akt/nnTOR signaling pathway regulates autophagy of macrophage and vulnerability of atherosclerotic plaque. PLoS One 9(3):e90563 (2014).
Zhu, Yi et al. The Achilles' heel of senescent cells: from transcriptome to senolytic drugs. Aging Cell. Aug. 2015;14(4):644-58. Epub Apr. 22, 2015.
Zhuang et al. Advances on small-molecule inhibitors of interfacing with p53-MDM2 protein-protein interactions. Chinese Journal of Medicinal Chemistry, Issue 5, pp. 403-407, 413 (2010).
Anderson, et al. Why is Osteoarthritis an Age-Related Disease? Best Pract Res Clin Rheumatol. Feb. 2010; 24(1):15.
Arya, et al. Nutlin-3, the small-molecule inhibitor of MDM2, promotes senescence and radiosensitises laryngeal carcinoma cells harbouring wild-type p53. Br J Cancer. Jul. 13, 2010;103(2):186-95.

(56) References Cited

OTHER PUBLICATIONS

Bajwa, et al. Inhibitors of the anti-apoptotic Bcl-2 proteins: a patent review. Expert Opin Ther Pat. Jan. 2012;22(1):37-55.
Baker, et al. Clearance of p16lnk4a—positive senescent cells delays ageing-associated disorders. Nature 479(7372):232-236 (2011).
Barak, et al. mdm2 expression is induced by wild type p53 activity. EMBO J. Feb. 1993;12(2):461-8.
Bhattacharya, S. et al. Age-Related Susceptibility to Apoptosis in Human Retinal Pigment Epithelial Cells Is Triggered by Disruption of p53-Mdm2 Association. Investigative Ophthalmology & Visual Science, 53(13):8350- 8366 (Dec. 2012).
Brenkman, et al. Mdm2 induces mono-ubiquitination of FOXO4. PLoS One. Jul. 30, 2008;3(7):e2819.
Campisi, et al. Cell senescence: role in aging and age-related diseases. Interdiscip Top Gerontol. 2014;39:45-61.
Campisi, J. Cellular senescence as a tumor-suppressor mechanism. Trends Cell Biol. Nov. 2001;11(11):S27-31.
Campisi, J. Cellular senescence: putting the paradoxes in perspective. Curr Opin Genet Dev. Feb. 2011;21(1):107-12.
Campisi, J. Senescent cells, tumor suppression, and organismal aging: good citizens, bad neighbors. Cell. Feb. 25, 2005;120(4):513-22.
Caruso, et al. Apoptotic-like tumor cells and apoptotic neutrophils in mitochondrion-rich gastric adenocarcinomas: a comparative study with light and electron microscopy between these two forms of cell death. Rare Tumors. Jun. 7, 2013;5(2):68-71.
Chang, et al. Clearance of senescent cells by ABT263 rejuvenates aged hematopoietic stem cells in mice. Nat Med. Dec. 14, 2015.
Coppe, et al. A Human-Like Senescence-Associated Secretory Phenotype Is Conserved in Mouse Cells Dependent on Physiological Oxygen. PLoS One 5:e9188 (2010).
Coppe, et al. Senescence-associated secretory phenotypes reveal cell-nonautonomous functions of oncogenic RAS and the p53 tumor suppressor. PLoS Biol. Dec. 2, 2008;6(12):2853-68.
Doroshevskaya, et al. Apoptosis Regulator Proteins: Basis for the Development of Innovation Strategies for the Treatment of Rheumatoid Arthritis in Patients of Different Age. Bulletin of Experimental Biology and Medicine. Jan. 2014, vol. 156, Issue 3, pp. 377-380.
Efeyan, et al. Induction of p53-dependent senescence by the MDM2 antagonist nutlin-3a in mouse cells of fibroblast origin. Cancer Res. Aug. 1, 2007;67(15):7350-7.
Faber, C. et al. Age-related Macular Degeneration Is Associated with Increased Proportion of CD56+ T Cells in Peripheral Blood. Ophthalmology, 120(11):2310-2316 (Nov. 2013).
Freund, et al. p38MAPK is a novel DNA damage response-independent regulator of the senescence-associated secretory phenotype. EMBO J. Apr. 20, 2011;30(8):1536-48.
Gagarina, et al. SirT1 enhances survival of human osteoarthritic chondrocytes by repressing protein tyrosine phosphatase 1B and activating the insulin-like growth factor receptor pathway. Arthritis Rheum. May 2010;62(5):1383-92.
Gannon et al., Mdm2-p53 signaling regulates epidermal stem cell senescence and premature aging phenotypes in mouse skin. Developmental Biology, 353:1-9, 2011.
Golstein, et al. Cell death by necrosis: towards a molecular definition. Trends in Biochemical Sciences. vol. 32, Issue 1, p. 37-43, Jan. 2007.
Guan, et al. Imidazoline derivatives: a patent review (2006—present). Expert Opin Ther Pat. Nov. 2012;22(11):1353-65.
Hashimoto, et al. Role of p53 in human chondrocyte apoptosis in response to shear strain. Arthritis Rheum. Aug. 2009;60(8):2340-9. First published Jul. 30, 2009.
Haupt, et al. Mdm2 promotes the rapid degradation of p53. Nature. May 15, 1997;387(6630):296-9.
Holford et al., Pharmacokinetics and Pharmacodynamics: Dose Selection & the Time Course of Drug Action, In: Katzung B.G., ed. Basic & Clinical Pharmacology (7th ed.), Appleton & Lange, Stamford, CT, 1998: 34-49.
Honda, et al. Oncoprotein MDM2 is a ubiquitin ligase E3 for tumor suppressor p53. FEBS Lett. Dec. 22, 1997;420(1):25-7.
Huang, et al. Reduced transcriptional activity in the p53 pathway of senescent cells revealed by the MDM2 antagonist nutlin-3. Aging (Albany NY). Oct. 2009; 1(10): 845-854.
Ianitti, et al. Intra-articular injections for the treatment of osteoarthritis: focus on the clinical use of hyaluronic acid. Drugs R D. 2011;11(1):13-27.
International search report and written opinion dated May 6, 2015 for PCT/US2015/013376.
Jakubsick, Claudia et al. Human Pulmonary Fibroblasts Exhibit Altered Interleukin-4 and Interleukin-13 Receptor Subunit Expression in Idiopathic Interstitial Pneumonia. Am J Pathol. Jun. 2004; 164(6): 1989-2001.
Jeon, et al. Local clearance of senescent cells attenuates the development of post-traumatic osteoarthritis and creates a pro-regenerative environment. Nat Med. Jun. 2017;23(6):775-781.
Juven, et al. Wild type p53 can mediate sequence-specific transactivation of an internal promoter within the mdm2 gene. Oncogene. Dec. 1993;8(12):3411-6.
Kerr, et al. Apoptosis: a basic biological phenomenon with wide-ranging implications in tissue kinetics. Br J Cancer. Aug. 1972;26(4):239-57.
Kroemer, et al. Classification of cell death: recommendations of the Nomenclature Committee on Cell Death 2009. Cell Death Differ. Jan. 2009; 16(1): 3-11.
Kubbutat, et al. Regulation of p53 stability by Mdm2. Nature. May 15, 1997;387(6630):299-303.
Laberge, et al. Glucocorticoids suppress selected components of the senescence-associated secretory phenotype. Aging Cell 11(4):569-578, 2012.
Laberge, et al. Mitochondrial DNA damage induces apoptosis in senescent cells. Cell Death Dis. Jul. 18, 2013;4:e727.
Lahav, Galit. Oscillations by the p53-Mdm2 feedback loop. Adv Exp Med Biol. 2008;641:28-38.
Leist, et al. Four deaths and a funeral: from caspases to alternative mechanisms. Nat Rev Mol Cell Biol. Aug. 2001;2(8):589-98.
Lessene; et al., "Structure-guided design of a selective BCL-X(L) inhibitor.", Nat Chem Biol., Jun. 2013, 9(6), 390-7.
Loeser, Richard F. Aging and Osteoarthritis: The Role of Chondrocyte Senescence and Aging Changes in the Cartilage Matrix. Osteoarthritis Cartilage. Aug. 2009; 17(8): 971-979.
Manfredi, James. The Mdm2-p53 relationship evolves: Mdm2 swings both ways as an oncogene and a tumor suppressor. Genes Dev. Aug. 1, 2010;24(15):1580-9.
Martin, et al. Chondrocyte senescence, joint loading and osteoarthritis. Clin Orthop Relat Res. Oct. 2004;(427 Suppl):S96-103.
Miyazaki, M. et al. Discovery of novel dihydroimidazothiazole derivatives as p53-MDM2 protein-protein interaction inhibitors: synthesis, biological evaluation and structure-activity relationships. Bioorg Med Chem Lett. Oct. 15, 2012;22(20):6338-42. Epub Aug. 30, 2012.
Miyazaki, M. et al. Lead optimization of novel p53-MDM2 interaction inhibitors possessing dihydroimidazothiazole scaffold. Bioorg Med Chem Lett. Feb. 1, 2013;23(3):728-32. Epub Dec. 1, 2012.
Momand, et al. The mdm-2 oncogene product forms a complex with the p53 protein and inhibits p53-mediated transactivation. Cell. Jun. 26, 1992;69(7):1237-45.
European Patent Application No. EP15743068.7. Extended Search Report and Search Opinion dated Aug. 28, 2017.
No Author. Idasanutlin CAS Registry File (retrieved Jan. 2018). (2018).
No Author. Navitoclax, Retrieved from CAS Registry Jan. 2018. (2018).
No Author. Form S-1 Registration Statement as Filed with the Securities and Exchange Commission on Apr. 23, 2018, pp. 1-243.
No Author. Glossary of medical education terms, institute of International Medical Education. pp. 1-23. http://www.iime.ogr/glossary.htm [Accessed Mar. 2013].
Oliner, et al. Oncoprotein MDM2 conceals the activation domain of tumour suppressor p53. Nature. Apr. 29, 1993;362(6423):857-60.
PCT/US2015/013376 International Preliminary Report on Patentability dated Aug. 2, 2016.

(56) References Cited

OTHER PUBLICATIONS

PCT/US2015/013387 International Preliminary Report on Patentability dated Aug. 2, 2016.
Perry, et al. The mdm-2 gene is induced in response to UV light in a p53-dependent manner. Proc Natl Acad Sci U S A. Dec. 15, 1993;90(24):11623-7.
Prieur, et al. Cellular senescence in vivo: a barrier to tumorigenesis. Curr Opin Cell Biol. Apr. 2008;20(2):150-5. Epub Mar. 18, 2008.
Rodier, et al. Persistent DNA damage signaling triggers senescence-associated inflammatory cytokine secretion. Nat Cell Biol. Aug. 2009;11(8):973-9.
Saczewski, et al. Imidazoline Scaffold in Medicinal Chemistry: A Patent Review (2012-2015). Expert Opin Ther Pat 26 (9), 1031-1048. Jul. 20, 2016.
Shangary, et al. Temporal activation of p53 by a specific MDM2 inhibitor is selectively toxic to tumors and leads to complete tumor growth inhibition. Proc Natl Acad Sci U S A. Mar. 11, 2008;105(10):3933-8.
Taranto, et al. Detection of the p53 regulator murine double-minute protein 2 in rheumatoid arthritis. J Rheumatol. Mar. 2005;32(3):424-9.
Thomasova, et al. p53-lndependent Roles of MDM2 in NF-κB Signaling: Implications for Cancer Therapy, Wound Healing, and Autoimmune Diseases. Neoplasia. Dec. 2012; 14(12): 1097-1101.
Tovar, et al. MDM2 small-molecule antagonist RG7112 activates p53 signaling and regresses human tumors in preclinical cancer models. Cancer Res. Apr. 15, 2013;73(8):2587-97.
UAMS News Bureau. UAMS Research Findings Show Radiation, Aging Effects Can Be Cleared with Drug; Findings Published in Nature Medicine, http://www.uamshealth.com/news. Dec. 14, 2015. 2 pages.
Uraoka, et al. Loss of bcl-2 during the senescence exacerbates the impaired angiogenic functions in endothelial cells by deteriorating the mitochondrial redox state. Hypertension. Aug. 2011;58(2):254-63.
U.S. Appl. No. 15/069,769 Office Action dated May 17, 2017.
U.S. Appl. No. 15/114,762 Final Office Action dated Feb. 5, 2018.
U.S. Appl. No. 15/114,762 Office Communication dated Sep. 14, 2017.
U.S. Appl. No. 15/455,575. First Action Interview Pilot Program Pre-Interview Communication dated May 16, 2017.
U.S. Appl. No. 15/455,575 Notice of Allowance dated Aug. 18, 2017 and corresponding allowed claims.
U.S. Appl. No. 15/455,630 Non-Final Office Action dated May 22, 2018.
U.S. Appl. No. 15/455,630 Non-Final Office Action dated Nov. 28, 2017.
U.S. Appl. No. 15/455,684 First Action Interview Office Action Summary dated Apr. 12, 2018.
U.S. Appl. No. 15/455,684 First Action Interview Pilot Program, Pre-Interview Communication dated Dec. 15, 2017.
U.S. Appl. No. 15/467,129 Notice of Allowance dated Aug. 3, 2017 and corresponding allowed claims.
U.S. Appl. No. 15/467,129 Office Communication dated Jul. 21, 2017.
"U.S. Appl. No. 15/481,129 First Action Interview dated Nov. 20, 2017".
U.S. Appl. No. 15/481,129 Office Communication dated Sep. 27, 2017.
U.S. Appl. No. 15/647,688 First Action Interview Pilot Program Pre-Interview Communication dated Feb. 6, 2018.
U.S. Appl. No. 15/827,539 First Action Interview Program Pre-Interview Communication dated Feb. 7, 2018.
U.S. Appl. No. 15/955,542 First Action Interview Pilot Program Pre-Interview Communication, dated Jun. 13, 2018.
Uthman, et al. Intra-articular therapy in osteoarthritis. Postgrad Med. J. 79:449-453 (2003).
Van Deursen, Jan M. The role of senescent cells in ageing. Nature. May 22, 2014;509(7501):439-46.
Vassilev, et al. In vivo activation of the p53 pathway by small-molecule antagonists of MDM2. Science. Feb. 6, 2004;303(5659):844-8. Epub Jan. 2, 2004.
Wang. Senescent human fibroblasts resist programmed cell death, and failure to suppress bcl2 is involved. Cancer Res. Jun. 1, 1995;55(11):2284-92.
Wilson C., Sweep Away Senile Cells. Life Extension Magazine, Mar. 2015, pp. 1-17.
Zauli, et al. Dasatinib plus Nutlin-3 shows synergistic antileukemic activity in both p53 wild-type and p53 mutated B chronic lymphocytic leukemias by inhibiting the Akt pathway. Clin Cancer Res. Feb. 15, 2011;17(4):762-70.
Zhang, et al. MDM2 Promotes Rheumatoid Arthritis via Activation of MAPK and NF-κB. Int Immunopharmacol 30, 69-73. Dec. 2, 2015.
Zhao, et al. Small molecule inhibitors of MDM2-p53 and MDMX-p53 interactions as new cancer therapeutics. BioDiscovery, 8. 2013; 8(4).15 pages.
Zhu, et al. Identification of a novel senolytic agent, navitoclax, targeting the Bcl-2 family of anti-apoptotic factors. Aging Cell. Jun. 2016;15(3):428-35. Epub Mar. 18, 2016.
Zhu, X. et al. Peripheral T Cell Functions Correlate with the Severity of Chronic Obstructive Pulmonary Disease. J. Immunol. 182(5):3270-3277 (Mar. 1, 2009).
EP19216214.7 Office Action dated Jan. 18, 2021.
Hartmann et al. Increased Expression and Redistribution of the Antiapoptotic Molecule Bcl-xL in Parkinson's Disease. Neurobiol Dis. 10:28-32 (2002).
Office action dated Aug. 27, 2020 for U.S. Appl. No. 16/508,119.
Office action dated Oct. 13, 2020 for U.S. Appl. No. 16/403,389.
U.S. Appl. No. 16/403,389 Office Action dated Jun. 18, 2021.
Veech et al. Disrupted Mitochondrial Electron Transport Function Increases Expression of Anti-Apoptotic Bcl-2 and Bcl-X(L) Proteins in SH-SY5Y Neuroblastoma and in Parkinson Disease Cybrid Cells through Oxidative Stress. J Neurosci Res 61:693-700 (2000).
Alder et al., "Short telomeres are a risk factor for idiopathic pulmonary fibrosis," Proc. Natl. Acad. Sci. USA, Sep. 2, 2008, 105(35):13051-13056.
Appel et al., "Mesoscopic atomic entanglement for precision measurements beyond the standard quantum limit," Proc. Natl. Acad. Sci. USA, Jan. 1991, 88(2):647-651.
Borchelt et al., "Accelerated amyloid deposition in the brains of transgenic mice coexpressing mutant presenilin 1 and amyloid precursor proteins," Neuron, Oct. 1, 1997, 19(4):939-945.
Brod, "Unregulated inflammation shortens human functional longevity," Inflamm. Research, Nov. 2000, 49(11):561-570.
Byeon et al., "The Role of Src Kinase in Macrophage-Mediated Inflammatory Responses," Mediators of Inflammation, Nov. 11, 2012, 2012:512926, 19 pages.
Campisi, "Aging, cellular senescence, and cancer," Annu. Rev. Physiology, 2013, 75:685-705.
CDC.gov [online], "National Diabetes Fact Sheet, 2011," 2011, retrieved on Mar. 17, 2022, retrieved from URL<https://www.cdc.gov/diabetes/pubs/pdf/methods11.pdf>, 10 pages.
Chavala et al., "Retinal angiogenesis suppression through small molecule activation of p53," J. Clin. Investigation, Oct. 2013, 123(10):4170-4181.
Christen et al., "Dietary ω-3 fatty acid and fish intake and incident age-related macular degeneration in women," Arch. Ophthalmology, Jul. 2011, 129(7):921-929.
Chung et al., "Molecular inflammation: underpinnings of aging and age-related diseases," Ageing Res. Reviews, Jan. 2009, 8(1):18-30.
Cohen et al., "The pathobiology of Parkinson's disease: biochemical aspects of dopamine neuron senescence," J. Neural Transm. Supplementum, Jan. 1983, 19:89-103.
Coppé et al., "Secretion of vascular endothelial growth factor by primary human fibroblasts at senescence," J. Biol. Chemistry, Oct. 6, 2006, 281(40):29568-29574.
Davalos et al., "p53-dependent release of Alarmin HMGB1 is a central mediator of senescent phenotypes," J. Cell Biology, May 13, 2013, 201(4):613-629.
De Boer et al., "Premature aging in mice deficient in DNA repair and transcription," Science, May 17, 2002, 296(5571):1276-1279.

(56) References Cited

OTHER PUBLICATIONS

Demedts et al., "Role of apoptosis in the pathogenesis of COPD and pulmonary emphysema," Respir. Research, Mar. 30, 2006, 7:53, 10 pages.

Dickson et al., "Alzheimer's disease. A double-labeling immunohistochemical study of senile plaques," Am. J. Pathology, Jul. 1988, 132(1):86-101.

Dimri et al., "A biomarker that identifies senescent human cells in culture and in aging skin in vivo," Proc. Natl. Acad. Sci. USA, Sep. 26, 1995, 92(20):9363-9367.

Feskanich et al., "Menopausal and reproductive factors and risk of age-related macular degeneration," Arch. Ophthalmology, Apr. 2008, 126(4):519-524.

Fischer et al., "Increased expression of senescence markers in cystic fibrosis airways," Am. J. Physiol. Lung Cell Mol. Physiology, Mar. 15, 2013, 304(6):L394-L400.

Freund et al., "Lamin B1 loss is a senescence-associated biomarker," Mol. Biol. Cell, Jun. 2012, 23(11):2066-2075.

Fried et al., "Frailty in older adults: evidence for a phenotype," J. Gerontol. A Biol. Sci. Med. Sciences, Mar. 2001, 56(3):M146-M156.

Funayama et al., "Loss of linker histone H1 in cellular senescence," J. Cell Biology, Dec. 11, 2006, 175(6):869-880.

Goren et al., "Severely impaired insulin signaling in chronic wounds of diabetic ob/ob mice: a potential role of tumor necrosis factor-alpha," Am. J. Pathology. Mar. 2006. 168(3):765-777.

Gorin et al., "The genetics of age-related macular degeneration," Mol. Vision, Apr. 8, 1999, 5:29, 6 pages.

Götz et al., "Tau filament formation in transeenic mice expressing P301L tau," J. Biol. Chemistry, Jan. 5, 2001, 276(1):529-534.

Hebert et al., "Alzheimer disease in the US population: prevalence estimates using the 2000 census," Arch. Neurology, Aug. 2003, 60(8):1119-1122.

Hendel et al., "Granzymes in age-related cardiovascular and pulmonary diseases," Cell Death Differentiation, Apr. 2010, 17(4):596-606.

Higuchi et al., "19F and 1H MRI detection of amyloid beta plaques in vivo," Nat. Neuroscience, Apr. 2005, 8(4):527-533.

Holcomb et al., "Accelerated Alzheimer-type phenotype in transeenic mice carrying both mutant amyloid precursor protein and presenilin 1 transgenes," Nat. Medicine, Jan. 1998, 4(1):97-100.

Hudson et al., "Clinical Ascertainment of Health Outcomes Among Adults Treated for Childhood Cancer," JAMA, Jun. 12, 2013, 309(22):2371-2381.

Iriyama et al., "A2E, a Pigment of the Lipofuscin of Retinal Pigment Epithelial Cells, Is an Endogenous Ligand for Retinoic Acid Receptor," J. Biol. Chemistry, May 2, 2008, 283(18):11947-11953.

Ishihara et al., "Age-dependent emergence and progression of a tauopathy in transgenic mice overexpressing the shortest human tau isoform," Neuron, Nov. 1999, 24(3):751-762.

Ivanov et al., "Lysosome-mediated processing of chromatin in senescence," J. Cell Biology, Jul. 8, 2013, 202(1):129-143.

Iyengar et al., "Dissection of Genomewide-Scan Data in Extended Families Reveals a Major Locus and Oligogenic Susceptibility for Age-Related Macular Degeneration," Am. J. Hum. Genetics, Jan. 1, 2004, 74(1):20-39.

Katzman et al., "Age-related hyperkyphosis: its causes, consequences, and management," J. Orthop. Sports Phys. Therapy, Jun. 2010, 40(6):352-360.

Kenealy et al., "Linkage analysis for age-related macular degeneration supports a gene on chromosome 10q26," Mol. Vision, Jan. 26, 2004, 10:57-61.

Klunk et al., "Imaging brain amyloid in Alzheimer's disease with Pittsburgh Compound-B," Ann. Neurology, Mar. 2004, 55(3):306-319.

Krtolica et al., "Senescent fibroblasts promote epithelial cell growth and tumorigenesis: a link between cancer and aging," Proc. Natl. Acad. Sci. USA, Oct. 9, 2001, 98(21):12072-12077.

Kuilman et al., "Senescence-messaging secretome: SMS-ing cellular stress," Nat. Reviews, Feb. 2009, 9(2):81-94.

Liang et al., "Caipain Activation Promotes BACE1 Expression, Amyloid Precursor Protein Processing, and Amyloid Plaque Formation in a Transgenic Mouse Model of Alzheimer Disease," J. Biol. Chemistry, Sep. 3, 2010, 285(36):27737-27744.

Lindstrom et al., "Rheumatoid arthritis: a role for immunosenescence?," J. Am. Geriatr. Society, Aug. 2010, 58(8):1565-1575.

Liton et al., "Cellular senescence in the glaucomatous outflow pathway," Exp. Gerontology, Aug./Sep. 2005, 40(8-9):745-748.

Lotz et al., "Compression-induced degeneration of the intervertebral disc: an in vivo mouse model and finite-element study," Spine, Dec. 1, 1998, 23(23):2493-2506.

Mandybur et al., "Astrocytes and the plaques of Alzheimer's disease," Neurology, Apr. 1, 1990, 40(4),635-639.

Millen et al., "Vitamin D status and early age-related macular degeneration in postmenopausal women," Arch. Ophthalmology, Apr. 2011, 129(4):481-489.

Minagawa et al., "Accelerated epithelial cell senescence in IPF and the inhibitory role of SIRT6 in TGF-βinduced senescence of human bronchial epithelial cells," Am. J. Physiol. Lung Cell. Mol. Physiology, Mar. 2011, 300(3):L391-L401.

Minamino et al., "A crucial role for adipose tissue p53 in the regulation of insulin resistance," Nat. Medicine, Sep. 2009, 15(9):1082-1087.

Mouratis et al., "Modeling pulmonary fibrosis with bleomycin," Curr. Opin. Pulm. Medicine, Sep. 2011, 17(5):355-361.

Mudhasani et al., "Loss of miRNA biogenesis induces p19Arf-p53 signaling and senescence in primary cells," J. Cell. Biology, Jun. 30, 2008, 181(7):1055-1063.

Nagele et al., "Contribution of glial cells to the development of amyloid plaques in Alzheimer's disease," Neurobiol. Aging, May/Jun. 2004, 25(5):663-674.

Naylor et al., "Senescent cells: a novel therapeutic target for aging and age-related diseases," Clin. Pharmacol. Therapy, Jan. 2013, 93(1):105-116.

Niemir et al., "Podocytes are the major source of IT-la and IL-113 in human glomerulonephiitides," Kidney International, Aug. 1997, 52(2):393-403.

Okutani et al., "Src protein tyrosine kinase family and acute inflammatory responses," Am. J. Physiol. Lung Cell Mol. Physiology, Aug. 2006, 291(2):LI29-L141.

Park et al., "Bmi1, stem cells, and senescence regulation," J. Clin. Investigation. Jan. 2004, 113(2):175-179.

Parrinello et al., "Stromal-epithelial interactions in aging and cancer: senescent fibroblasts alter epithelial cell differentiation," J. Cell Science, Feb. 1, 2005, 118(Pt 3):485-496.

Peng et al., "Bleomycin induces molecular changes directly relevant to idiopathic pulmonary fibrosis: a model for "active" disease," PLoS One, Apr. 2, 2013, 8(4):e59348, 15 pages.

Pennesi et al., "Animal models of age related macular degeneration," Mol. Aspects Medicine, Aug. 2012, 33(4):487-509.

Pepeu, "Mild cognitive impairment: animal models," Dialogues Clin. Neuroscience, Dec. 2004, 6(4):369-377.

Ray et al., "Imaging tri-fusion multimodality reporter gene expression in living subjects," Cancer Research, Feb. 15, 2004, 64(4):1323-1330.

Rich et al., "Reduced Endplate Currents Underlie Motor Unit Dysfunction in Canine Motor Neuron Disease," J. Neurophysiology, Dec. 2002, 88(6):3293-3304.

Roberts et al., "Senescence in human intervertebral discs," Eur. Spine Journal, Aug. 2006, 15(Suppl 3):S312-S316.

Roos et al., "Transcriptional and phenotypic changes in aorta and aortic valve with aging and MnSOD deficiency in mice," Am. J. Physiol. Heart Cir. Physiology, Nov. 15, 2013, 305(10):H1428-H1439.

Seitz et al., "Wound healing in mice with high-fat diet- or ob gene-induced diabetesobesity syndromes: a comparative study," Exp. Diabetes Research, 2010, 2010:476969, 16 pages.

Shapiro et al., "The pathogenesis of chronic obstructive pulmonary disease: advances in the past 100 years," Am. J. Respir. Cell Mol. Biology, May 2005, 32(5):367-372.

Sharma et al., "Effect of aging on respiratory svstem physiology and immunology," Clin. Interv. Aging, 2006, 1(3):253-260.

(56) References Cited

OTHER PUBLICATIONS

Sis et al., "Accelerated expression of senescence associated cell cycle inhibitor p16INK4A in kidneys with glomerular disease," Kidney International, Feb. 2007, 71(3):218-226.

Skovronsky et al., "In vivo detection of amyloid plaques in a mouse model of Alzheimer's disease," Proc. Natl. Acad. Sci. USA, Jun. 20, 2000, 97(13):7609-7614.

Sousa-Victor et al., "Geriatric muscle stem cells switch reversible quiescence into senescence," Nature, Feb. 20, 2014, 506(7488):316-321.

Stanley et al., "Senescence and the healing rates of venous ulcers," J. Vas. Surgery, Jun. 1, 2011, 33(6):1206-1211.

Sun et al., "Treatment-induced damage to the tumor microenvironment promotes prostate cancer therapy resistance through WNT16B," Nat, Medicine, Sep. 2012, 18(9):1359-1368.

Tchkonia et al., "Fat tissue, aging, and cellular senescence," Aging Cell, Oct. 2010, 9(5):667-684.

Thomas et al., "Cellular functions regulated by Src family kinases," Annu. Rev. Cell Dev. Biology, 1997, 13:513-609.

Wang et al., "Characterization of regulatory elements on the promoter region of p16(INK4a) that contribute to over expression of p16 in senescent fibroblasts," J. Biol. Chemistry, Dec. 28, 2001, 276(52):48655-48661.

Wang, "Regulation of cell death by the Abl tyrosine kinase," Oncogene, Nov. 20, 2000, 19(49):5643-5650.

Wengenack et al., "Tarsetins Alzheimer amyloid plaques in vivo," Nat. Biotechnology, Aug. 2000, 18(8):868-872.

Wesselink et al., "Glaucoma Monitoring in a Clinical Setting: Glaucoma Progression Analysis vs Nonparametric Progression Analysis in the Groningen Longitudinal Glaucoma Study," Arch. Ophthalmology, Mar. 9, 2009, 127(3):270-274.

Xue, "The frailty syndrome: definition and natural history," Clin. Geriatr. Medicine, Feb. 1, 2011, 27(1):1-15.

Zeiss, "Review Paper: Animals as Models of Age-Related Macular Deseneration: An Imperfect Measure of the Truth," Vet. Pathology, Apr. 9, 2010, 47(3):396-413.

Zhao et al., "The cell biology of intervertebral disc aging and degeneration," Ageing Res. Reviews, Oct. 2007, 6(3):247-261.

\* cited by examiner

KILLING SENESCENT CELLS AND TREATING SENESCENCE-ASSOCIATED CONDITIONS USING A SRC INHIBITOR AND A FLAVONOID

STATEMENT OF GOVERNMENT INTEREST

This invention was made with government support under AG041122 and AG046061 awarded by the National Institutes of Health. The government has certain rights in the invention.

BACKGROUND OF THE INVENTION

Technical Field

The disclosure herein relates generally to methods for treatment and prophylaxis of senescent cell-associated diseases and disorders.

Description of the Related Art

Senescent cells accumulate in tissues and organs of individuals as they age and are found at sites of age-related pathologies. Senescent cells are believed important to inhibiting proliferation of dysfunctional or damaged cells and particularly to constraining development of malignancy (see, e.g., Campisi, Curr. Opin. Genet. Dev. 21:107-12 (2011); Campisi, Trends Cell Biol. 11:S27-31 (2001); Prieur et al., Curr. Opin. Cell Biol. 20:150-55 (2008)); nevertheless, the presence of senescent cells in an individual may contribute to aging and aging-related dysfunction (see, e.g., Campisi, Cell 120:513-22 (2005)). Given that senescent cells have been causally implicated in certain aspects of age-related decline in health and may contribute to certain diseases, and are also induced as a result of necessary life-preserving chemotherapeutic and radiation treatments, the presence of senescent cells may have deleterious effects to millions of patients worldwide. However, identifying and developing treatments of such diseases and conditions by selective elimination of senescent cells has been an arduous undertaking. The present disclosure addresses these needs and offers related advantages.

BRIEF SUMMARY

Provided herein are methods and agents for selective killing of senescent cells that are associated with numerous pathologies and diseases, including age-related pathologies and diseases. Described herein are the following embodiments.

In one embodiment, a method is provided for treating a senescence associated disease or disorder in a subject comprising administering to the subject a senolytic combination, which senolytic combination comprises (a) a first agent that alters either one or both of a cell survival signaling pathway and an inflammatory pathway; and (b) a second agent that alters either one or both of a cell survival signaling pathway and an inflammatory pathway; wherein the senescence associated disease or disorder is not a cancer, wherein the first agent and second agent are different, and wherein the senolytic combination is administered during a treatment course of 1-7 days every 0.5-12 months; provided that if the senescence associated disease or disorder is a senescence associated metabolic disorder, the senolytic combination is administered during a treatment course of 1-7 days every 4-12 months. In certain embodiments, the senolytic combination is administered once every 0.5-12 months; provided that if the senescence associated disease or disorder is a senescence associated metabolic disorder, the senolytic combination is administered once every 4-12 months. In other certain embodiments, the senescent cell-associated disease or disorder is a cardiovascular disease or disorder, inflammatory disease or disorder, a pulmonary disease or disorder, a neurological disease or disorder. In a specific embodiment, the cardiovascular disease or disorder is atherosclerosis. In another specific embodiment, the inflammatory disease or disorder is osteoarthritis. In another specific embodiment, the pulmonary disease or disorder is idiopathic pulmonary fibrosis or chronic obstructive pulmonary disease. In another specific embodiment, the neurological disease or disorder is selected from mild cognitive impairment; motor neuron dysfunction; Alzheimer's disease; Parkinson's disease; and macular degeneration. In another specific embodiment, the senescence associated metabolic disease or disorder is selected from diabetes, metabolic syndrome, and obesity. In another specific embodiment, the senescence-associated disease or disorder is a dermatological disease or disorder is selected from eczema, psoriasis, hyperpigmentation, nevi, rashes, atopic dermatitis, urticaria, diseases and disorders related to photosensitivity or photoaging, rhytides; pruritus; dysesthesia; eczematous eruptions; eosinophilic dermatosis; reactive neutrophilic dermatosis; pemphigus; pemphigoid; immunobullous dermatosis; fibrohistocytic proliferations of skin; cutaneous lymphomas; and cutaneous lupus.

In one embodiment, a method is provided for treating a senescence-associated metabolic disease or disorder in a subject comprising administering to the subject a senolytic combination, which senolytic combination comprises (a) a first agent that alters either one or both of a cell survival signaling pathway and an inflammatory pathway; and (b) a second agent that alters either one or both of a cell survival signaling pathway and an inflammatory pathway, wherein the first agent and second agent are different, wherein the senolytic combination is administered during a treatment course of 1-7 days every 4-12 months, and wherein the metabolic disease or disorder is selected from diabetes, metabolic syndrome, and obesity. In a specific embodiment, the senolytic combination is administered once every 4-12 months. In another specific embodiment, the senescent cell is selected from a senescent fibroblast, a senescent pre-adipocyte, a senescent epithelial cell, a senescent chondrocyte, a senescent neuron, and a senescent endothelial cell. In another specific embodiment, the senescent cell is a senescent pre-adipocyte.

In the above embodiments and the embodiments described herein, the first agent is a src inhibitor and the second agent is a flavonoid. In more specific embodiments, the first agent is dasatinib and the second agent is a compound having a structure of the following formula (I):

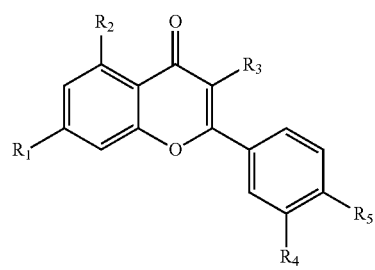

Formula (I)

or a pharmaceutically acceptable salt, stereoisomer, tautomer, or prodrug thereof, wherein $R_1$ is —OH or H;
$R_2$ is —OH or H;
$R_3$ is —OH, H, $R_6$, or —OCH$_2$PO(OH)$_2$;
$R_4$ is —OH, —OPO(OH)(O—), —OCH$_3$, —OCH$_2$PO(OH)$_2$, $R_6$, H, or —OSO$_3$—; and
$R_5$ is —OH, H, $R_6$, or —OCH$_3$,
wherein $R_6$ is

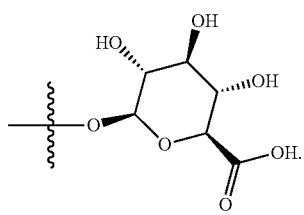 [SMILES: *O[C@@H]1O[C@H](C(=O)O)[C@@H](O)[C@H](O)[C@H]1O]

In a specific embodiment, $R_3$ is —OH, $R_6$, or —OCH$_2$PO(OH)$_2$.

In a specific embodiment, $R_3$ is —OH.

In a specific embodiment, $R_4$ is —OH, —OPO(OH)(O), —OCH$_3$, —OCH$_2$PO(OH)$_2$, $R_6$, or —OSO$_3$—.

In a specific embodiment, $R_4$ is —OH, —OPO(OH)(O—), —OCH$_2$PO(OH)$_2$, $R_6$, or —OSO$_3$—.

In a specific embodiment, $R_4$ is —OH, $R_6$, or —OSO$_3$—.

In a specific embodiment, $R_5$ is —OH or $R_6$.

In a specific embodiment, the compound of Formula (1) is selected from:

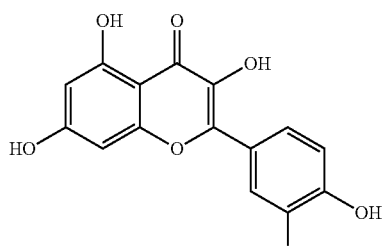

(quercetin)

(Ia)

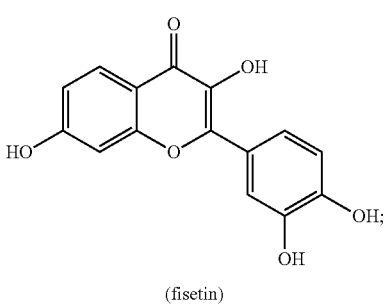

(fisetin)

(Ib)

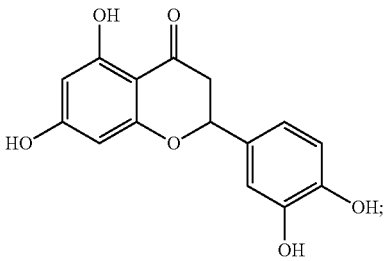

(luteolin)

(Ic)

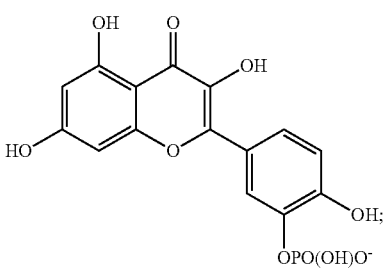

(Id)

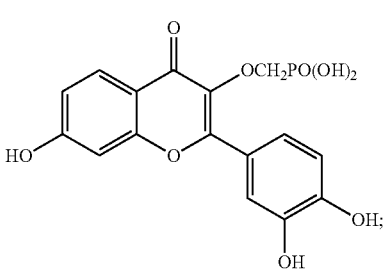

(Ie)

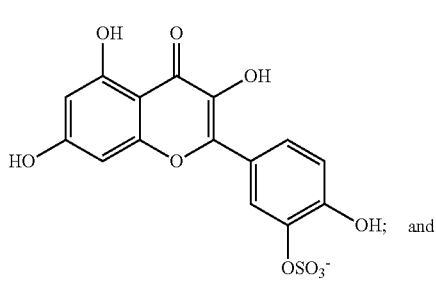

(If)

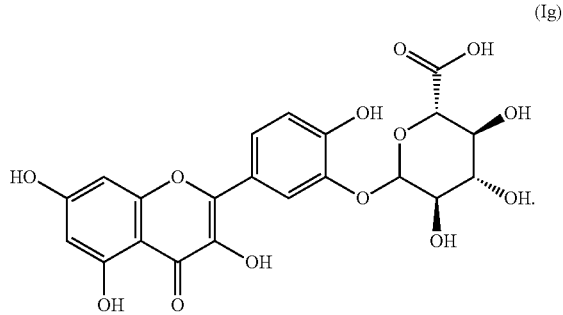

(Ig)

In one embodiment, a method is provided for treating, reducing the likelihood of occurrence of, or delaying onset of a senescent cell-associated disease or disorder in a subject who has a senescent cell-associated disease or disorder or who has at least one predisposing factor for developing the senescent cell-associated disease or disorder, comprising administering to the subject a senolytic combination that comprises (a) a first agent that alters either one or both of a cell survival signaling pathway and an inflammatory pathway in the senescent cell, and (b) a second agent that alters either one or both of a cell survival signaling pathway and an inflammatory pathway in the senescent cell, thereby promoting death of the senescent cell, wherein the senescent cell-associated disease or disorder is a cardiovascular disease or disorder, inflammatory disease or disorder, a pulmonary disease or disorder, a neurological disease or disorder, with the proviso that if the subject has a cancer, neither the first agent nor the second agent is a primary therapy for treating the cancer, and wherein the first agent is administered once every 0.5-12 months and the second agent is administered once every 0.5-12 months, and wherein the first and second agents are different.

In another embodiment, a method is provided for treating, reducing the likelihood of occurrence of, or delaying onset of a senescent cell-associated disease or disorder in a subject who has a senescent cell-associated disease or disorder or who has at least one predisposing factor for developing the senescent cell-associated disease or disorder, comprising administering to the subject a senolytic combination comprising (a) a first agent that alters either one or both of a cell survival signaling pathway and an inflammatory pathway in the senescent cell, and (b) a second agent that alters either one or both of a cell survival signaling pathway and an inflammatory pathway in the senescent cell, thereby promoting death of the senescent cell, wherein the senescent cell-associated disease or disorder is a metabolic disorder selected from diabetes, metabolic syndrome, and obesity, and wherein the senolytic combination is administered once every 4-12 months, and wherein the first and second agents are different.

In another embodiment, a method is provided for treating, reducing the likelihood of occurrence of, or delaying onset of a senescent cell-associated condition or disorder in a subject who has a senescent cell-associated disease or disorder or who has at least one predisposing factor for developing the senescent cell-associated disease or disorder, comprising administering to the subject a senolytic combination comprising (a) a first agent that alters either one or both of a cell survival signaling pathway and an inflammatory pathway in the senescent cell, and (b) a second agent that alters either one or both of a cell survival signaling pathway and an inflammatory pathway in the senescent cell, thereby promoting death of the senescent cell, and wherein the senescent cell-associated disease or disorder is selected from atherosclerosis, osteoarthritis, idiopathic pulmonary fibrosis, and chronic obstructive pulmonary disease, and wherein the senolytic combination is administered once every 0.5-12 months, and wherein the first and second agents are different.

In another embodiment, a method is provided for killing a senescent cell comprising contacting the senescent cell and a senolytic combination comprising (a) a first agent that alters either one or both of a cell survival signaling pathway and an inflammatory pathway in the senescent cell and (b) a second agent that alters either one or both of a cell survival signaling pathway and an inflammatory pathway in the senescent cell, thereby promoting death of the senescent cell, wherein the senescence cell is present in a subject who has a senescent cell-associated disease or disorder or who has at least one predisposing factor for developing the senescent cell-associated disease or disorder, with the proviso that if the subject has a cancer, neither the first agent nor the second agent of the combination is a primary therapy for treating the cancer, wherein the senescent cell-associated disease or disorder is a cardiovascular disease or disorder, inflammatory disease or disorder, a pulmonary disease or disorder, a neurological disease or disorder, wherein the combination is administered once every 0.5-12 months, and wherein the first and second agents are different.

In certain embodiments of the methods described above and herein, the senescent cell-associated disease or disorder is selected from atherosclerosis; osteoarthritis; idiopathic pulmonary fibrosis; chronic obstructive pulmonary disease; mild cognitive impairment; motor neuron dysfunction; Alzheimer's disease; Parkinson's disease; and macular degeneration.

In another embodiment, a method is provided for killing a senescent cell comprising contacting the senescent cell and a senolytic combination comprising (a) a first agent that alters either one or both of a cell survival signaling pathway and an inflammatory pathway in the senescent cell and (b) a second agent that alters either one or both of a cell survival signaling pathway and an inflammatory pathway in the senescent cell, thereby promoting death of the senescent cell, wherein the senescence cell is present in a subject who has a senescent cell-associated disease or disorder or who has at least one predisposing factor for developing the senescent cell-associated disease or disorder, wherein the senescent cell-associated disease or disorder is a metabolic disorder selected from diabetes, metabolic syndrome, and obesity, and wherein the combination is administered once every 4-12 months, and wherein the first and second agents are different.

In another embodiment, a method is provided for treating or reducing the likelihood of occurrence of atherosclerosis in a subject who has atherosclerosis or who has at least one predisposing factor for developing atherosclerosis, comprising administering to the subject a senolytic combination comprising (a) a first agent that alters either one or both of a cell survival signaling pathway and an inflammatory pathway in the senescent cell, and (b) a second agent that alters either one or both of a cell survival signaling pathway and an inflammatory pathway in the senescent cell, thereby promoting death of the senescent cell, wherein the combination is administered once every 0.5-12 months, and wherein the first and second agents are different.

In certain embodiments of the methods described above and herein, the senescent cell is selected from a senescent fibroblast, a senescent pre-adipocyte, a senescent epithelial cell, a senescent chondrocyte, a senescent neuron, a senescent smooth muscle cell, a senescent mesenchymal cell, a senescent macrophage, and a senescent endothelial cell. In certain specific embodiments, the senescent cell is a senescent pre-adipocyte.

In certain embodiments of the methods described above and herein, at least one of the first agent and the second agent inhibits Src kinase (e.g., dasatinib) and the second agent is a flavonoid, (e.g., quercetin or an analog thereof).

In certain embodiments of the methods described above and herein, the first agent of the combination is dasatinib and the second agent is a compound having a structure of the following formula (I) (i.e., quercetin or an analog thereof) as described above and in greater detail herein.

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising," are to be construed in an open, inclusive sense, that is, as "including, but not limited to." In addition, the term "comprising" (and related terms such as "comprise" or "comprises" or "having" or "including") is not intended to exclude that in other certain embodiments, for example, an embodiment of any composition of matter, composition, method, or process, or the like, described herein, may "consist of or "consist essentially of the described features. Headings provided herein are for convenience only and do not interpret the scope or meaning of the claimed embodiments.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Also, as used in this specification and the appended claims, the singular forms "a," "an," and "the" include plural referents unless the content clearly dictates otherwise. Thus, for example, reference to "a non-human animal" may refer to one or more non-human animals, or a plurality of such animals, and reference to "a cell" or "the cell" includes reference to one or more cells and equivalents thereof (e.g., plurality of cells) known to those skilled in the art, and so forth. When steps of a method are described or claimed, and the steps are described as occurring in a particular order, the description of a first step occurring (or being performed) "prior to" (i.e., before) a second step has the same meaning if rewritten to state that the second step occurs (or is performed) "subsequent" to the first step. The term "about" when referring to a number or a numerical range means that the number or numerical range referred to is an approximation within experimental variability (or within statistical experimental error), and thus the number or numerical range may vary between 1% and 15% of the stated number or numerical range. For example, the use of "about X" shall encompass+/-1%, 2%, 3%, 4%, 5%, 6%, 7%, 8%, 9%, 10%, 11%, 12%, 13%, 14% and 15% of the value X. It should also be noted that the term "or" is generally employed in its sense including "and/or" unless the content clearly dictates otherwise. The term, "at least one," for example, when referring to at least one compound or to at least one composition, has the same meaning and understanding as the term, "one or more."

BRIEF DESCRIPTION OF THE DRAWINGS

FIG. 2A shows possible target proteins affected indirectly by quercetin, which alters a cell signaling pathway. FIG. 2B illustrates downstream components of the Src kinase pathway. FIG. 2C shows the downstream components of the PI3K pathway. FIG. 2D illustrates downstream components of the Akt pathway. A solid arrow between two components indicates that the component at the source of the solid line has a direct role in upregulating the component to which the arrow is pointing.

FIG. 4A presents the effect of quercetin on senescent and proliferating, endothelial cells at the concentrations shown. FIG. 4B illustrates the effect of dasatinib alone on senescent and proliferating endothelial cells at the concentrations shown. FIG. 4C illustrates the effect of dasatinib in combination with quercetin on senescent and proliferating endothelial cells at the concentrations shown. FIG. 4D presents the effect of enzastaurin on senescent and proliferating, endothelial cells at the concentrations shown; FIG. 4E illustrates the effect of dasatinib in combination with enzastaurin on senescent and proliferating endothelial cells at the concentrations shown. FIG. 4F illustrates the effect of enzastaurin in combination with quercetin on senescent and proliferating endothelial cells at the concentrations shown.

FIG. 5A presents the effect of quercetin on senescent, proliferating, and differentiated preadipocytes at the concentrations shown. FIG. 5B illustrates the effect of dasatinib alone on senescent, proliferating, and differentiated preadipocytes at the concentrations shown. FIG. 5C illustrates the effect of dasatinib in combination with quercetin on senescent, proliferating, and differentiated preadipocytes at the concentrations shown. FIG. 5D presents the effect of enzastaurin on senescent and proliferating preadipocytes cells at the concentrations shown; FIG. 5E illustrates the effect of dasatinib in combination with enzastaurin on senescent and proliferating preadipocytes cells at the concentrations shown. FIG. 5F illustrates the effect of enzastaurin in combination with quercetin on senescent and proliferating preadipocytes cells at the concentrations shown.

FIG. 7A illustrates the percent luminescence (y-axis) for each animal treatment group. FIG. 7B presents the luminescent images of representative mice in each group.

FIG. 10A presents the effect of dasatinib+quercetin on senescent or non-senescent cells. FIG. 10B shows DAPI stained non-senescent cells treated with dasatinib+quercetin; FIG. 10D shows DAPI stained senescent cells treated with vehicle; and FIG. 10F presents DAPI stained senescent cells treated with dasatinib+quercetin, respectively. TUNEL stained non-senescent cells treated with dasatinib+quercetin are shown in FIG. 10C; senescent cells treated with vehicle in FIG. 10E, and senescent cells treated with dasatinib+quercetin in FIG. 10G Treatment with dasatinib+quercetin induced apoptosis in senescent (FIG. 10G) but not in non-senescent cells (FIG. 10C).

FIG. 23A presents fat depot size in diet-induced obese (DIO) animals and chow fed animals treated with D+Q or vehicle. Mice were treated with dasatinib and quercetin (D+Q) once per week (5 mg/kg D, 100 mg/kg Q) at 4 months of age. Mice were sacrificed after 28 weeks of treatment. Fat depot weights were measured at time of sacrifice and are expressed as percent of whole body weight. Epi=epididymal fat; Mes=mesenteric fat; Peri=perirenal fat. An increase in subscapular fat depot weight was seen in diet-induced obese (DIO) mice treated with D+Q (n=6) compared with vehicle-treated mice (n=10). No difference in chow-fed mice fat depot weights were seen between treatment and vehicle groups (n=9). The weights of other organs obtained from the animals are shown FIG. 23B.

DETAILED DESCRIPTION

Figure 1:
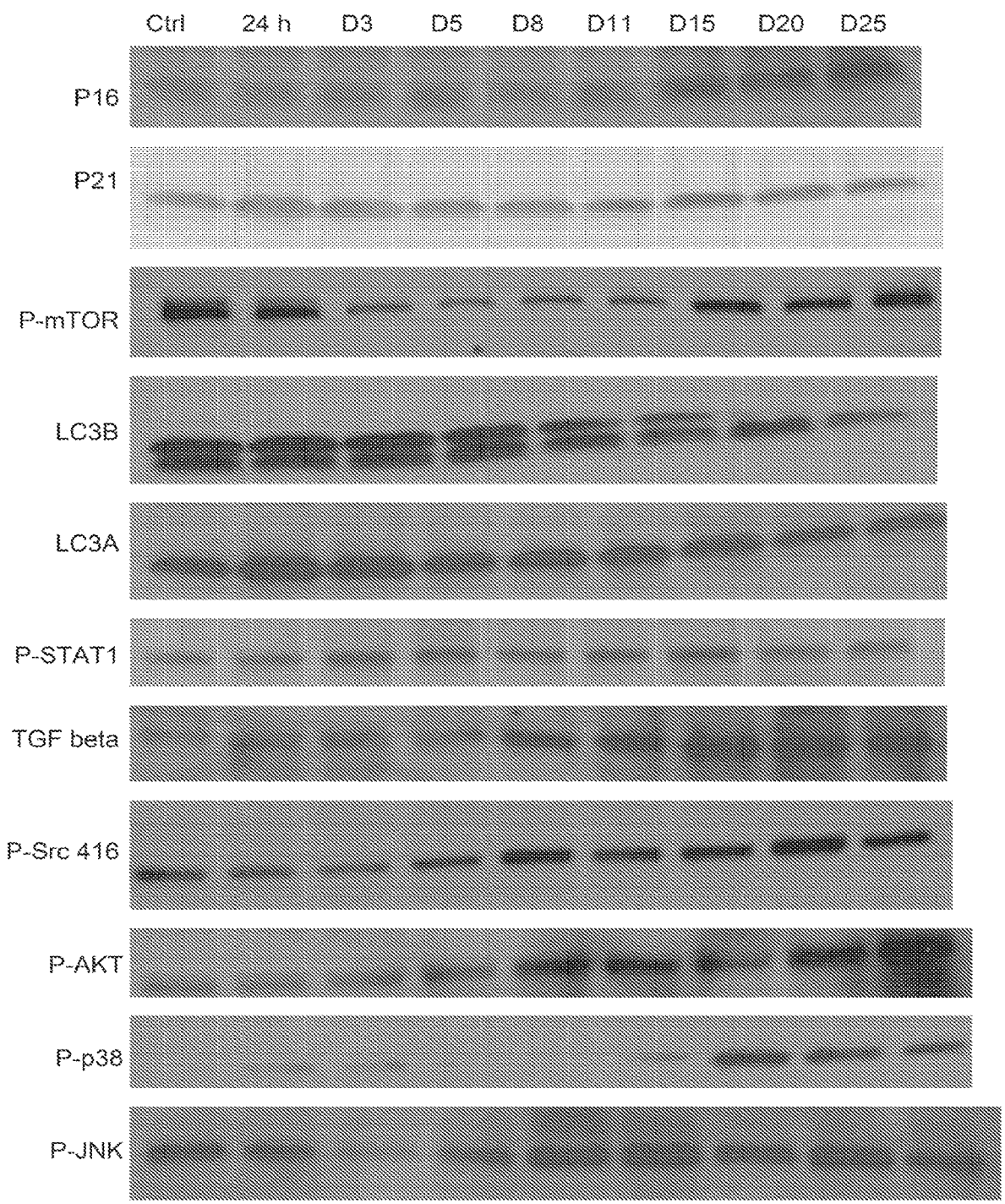
FIG. 1 shows an immunoblot showing the level of different cellular proteins in senescent and non-senescent human abdominal subcutaneous preadipocytes. Senescence was induced as described in Example 1. Lysates were prepared at several time points after induction of senescence, and the level of each protein in the lysates detected at 24 hours and at days 3, 5, 8, 11, 15, 20, and 25 (D3, D5, D8, D11, D15, D20, and D25).

Aging is a risk factor for most chronic diseases, disabilities, and declining health. Senescent cells, which are cells in replicative arrest, accumulate as an individual ages and may contribute partially or significantly to cell and tissue deterioration that underlies aging and age related diseases. Cells may also become senescent after exposure to an environmental, chemical, or biological insult or as a result of a disease. Provided herein are methods and agents for use in combination to selectively kill senescent cells that are associated with numerous pathologies and diseases, including age-related pathologies and diseases. Senescent cell associated diseases and disorders (also called herein senescence-associated diseases and disorders) may be treated or prevented (i.e., the likelihood of occurrence is reduced) by administering a senolytic agent (one that selectively kills senescent cells alone) or a combination of agents that together selective kill senescent cells. Examples of senolytic combinations include dasatinib and quercetin or analogs thereof. In certain embodiments as described herein, agents are administered in combination to provide a senolytic effect, that is, selectively killing senescent cells over non-senescent cells. The agents may be compounds that alter either a cell survival signaling pathway or an inflammatory pathway or may alter both the cell survival signaling pathway and the inflammatory pathway in a senescent cell. Selective killing of senescent cells may occur when at least two different agents are used in combination (called senolytic combination). In certain instances, agents of a senolytic combination may have minimal, if any, observed selective killing of senescent cells when used alone. In particular embodiments, a senolytic combination provides a greater senolytic effect than when either agent is used alone.

The senescent cell-associated disease or disorder treated or prevented by the agents and methods described herein include a cardiovascular disease or disorder, inflammatory disease or disorder, a pulmonary disease or disorder, a neurological disease or disorder, a chemotherapeutic side effect, a radiotherapy side effect, or metastasis, or a metabolic disease, all of which are described in greater detail herein. In some embodiments, a senescent cell-associated disease or disorder does not include cancer. In particular embodiments, each of the at least two agents may be minimally or not senolytic when used alone. For convenience, when two or more agents are described herein as being used in combination, one agent will be called a first agent, and the other agent will be called the second agent. The adjectives, first, second, third, and such, in this context are used for convenience only and are not to be construed as describing order or administration, preference, or level of activity or other parameter unless expressly described otherwise herein. A single dose of the senolytic combination described herein is sufficient to kill senescent cells.

Senolytic Combination

A senolytic combination "selectively" (preferentially or to a greater degree) destroys or kills a senescent cell. In other words, the senolytic combination destroys or kills a senescent cell in a biologically, clinically, and/or statistically significant manner compared with its capability to destroy or kill a non-senescent cell. A senolytic combination is used in an amount and for a time sufficient that selectively kills established senescent cells but is insufficient to kill (destroy, cause the death of) a non-senescent cell in a clinically significant or biologically significant manner. In certain embodiments, the senolytic combination described herein alters at least one signaling pathway in a manner that induces (initiates, stimulates, triggers, promotes) and results in (i.e., causes, leads to) death of the senescent cell. The senolytic combination may alter, for example, either or both of a cell survival signaling pathway (e.g., Akt pathway) or an inflammatory pathway, for example, by antagonizing a protein within the cell survival and/or inflammatory pathway.

Without wishing to be bound by a particular theory, the mechanism by which the combination described herein selectively kills senescent cells is by inducing (activating, stimulating, removing inhibition of) an apoptotic pathway that leads to cell death. Non-senescent cells may be proliferating cells or may be quiescent cells. In certain instances, exposure of non-senescent cells to the senolytic combination as used in the methods described herein may temporarily reduce the capability of non-senescent cell to proliferate; however, an apoptotic pathway is not induced and the non-senescent cell is not destroyed.

The methods described herein are useful for treating a senescence-associated disorder or disease that is not a cancer. The method used for treating a senescence associated disease or disorder with a senolytic combination described herein may comprise one or more of a decreased daily dose, decreased cumulative dose over a single treatment cycle, or decreased cumulative dose of the agent from multiple treatment cycles than the dose of an agent required for cancer therapy, which methods are described in greater detail herein. The reduced doses of the agents may also result in the likelihood of decreased adverse effects (i.e., side effects). In other words, when treating a senescent cell associated disease or disorder (that is not cancer) in a subject, including a subject who has a cancer, by using the methods described herein, the senolytic combination may be used in a manner inconsistent with a primary therapy for treating the cancer. To further reduce toxicity, a senolytic combination may be administered at a site proximal to or in contact with senescent cells (not tumor cells). Localized delivery of a senolytic combination is described in greater detail herein. A "primary therapy for cancer" as used herein means that when an agent, which may be used alone or together with one or more agents, is intended to be or is known to be an efficacious treatment for the cancer as determined by a person skilled in the medical and oncology arts, administration protocols for treatment of the cancer using the agent have been designed to achieve the relevant cancer-related endpoints.

The senolytic combination described herein alter (i.e., interfere with, affect) one or more cellular pathways that are activated during the senescence process of a cell. Senolytic combinations may alter either a cell survival signaling pathway or an inflammatory pathway or alter both a cell survival signaling pathway and an inflammatory pathway. Activation of certain cellular pathways during senescence decreases or inhibits the cell's capability to induce, and ultimately undergo apoptosis. Without wishing to be bound by theory, the mechanism by which a senolytic combination selectively kills senescent cells is by inducing (activating, stimulating, removing inhibition of) an apoptotic pathway that leads to cell death. A senolytic combination may alter one or more signaling pathways by interacting with one, two, or more target proteins in the one or more pathways, which results in removing or reducing suppression of a cell death pathway, such as an apoptotic pathway. Contacting or exposing a senescent cell to a senolytic combination to alter one, two, or more cellular pathways in the senescent cell, restores the cell's mechanisms and pathways for initiating apoptosis. In certain embodiments, a senolytic combination alters a signaling pathway, which in turn inhibits secretion and/or expression of one or more gene products important for survival of a senescent cell. The senolytic combination may inhibit a biological activity of the gene product(s) important for survival of the senescent cell. Alternatively, the decrease or reduction of the level of the gene product(s) in the senescent cell may alter the biological activity of another cellular component, which triggers, initiates, or stimulates an apoptotic pathway or removes or reduces suppression of the apoptotic pathway. As described herein, neither agent of the senolytic combination is necessarily linked or conjugated to a cytotoxic moiety (e.g., a toxin or cytotoxic peptide or cytotoxic nucleic acid). The senolytic combination is also active in selectively killing senescent cells in the absence of linkage or conjugation of either one or both agents of the combination to a targeting moiety (e.g., an antibody or antigen-binding fragment thereof; cell binding peptide) that selectively binds senescent cells.

Two alternative modes of cell death can be distinguished, apoptosis and necrosis. The term apoptosis was initially used by Kerr and colleagues (*Br. J. Cancer* 26:239-57 (1972)) to describe the phenomenon as a mode of cell death morphologically distinct from coagulative necrosis. Apoptosis is typically characterized by the rounding of the cell, chromatin condensation (pyknosis), nuclear fragmentation (karyorhexis), and engulfment by neighboring cells (see, e.g., Kroemer et al., *Cell Death Differ.* 16:3-11 (2009)). Several molecular assays have been developed and are used in the art; however, the morphological changes, which are detected by light and electron microscopy, are viewed in the art as the optimal techniques to differentiate the two distinct modes of cell death (see, e.g., Kroemer et al., supra). Alternative cell death modes, such as caspase-independent apoptosis-like programmed cell death (PCD), autophagy, necrosis-like PCD, and mitotic catastrophe, have also been characterized (see, e.g., Golstein, *Biochem. Sci.* 32:37-43 (2007); Leist et al., *Nat. Rev. Mol. Cell Biol.* 2:589-98 (2001)). See, e.g., Caruso et al., *Rare Tumors* 5(2): 68-71 (2013); published online 2013 Jun. 7. doi: 10.3081/rt.2013.e18. Techniques and methods routinely practiced in the art and described herein (e.g., TUNEL) may be used to show that apoptotic cell death results from contact with the senolytic combination described herein.

In certain embodiments, a senolytic combination as used in the methods described herein is comprises two small molecule compounds. In certain embodiments, an agent of the combination is a small molecule that may be activated or that is a pro-drug that is converted to the active form by enzymes within the cell. In a more specific embodiment, the enzymes that convert a pro-drug to an active form are those expressed at a higher level in senescent cells than in non-senescent cells.

Methods are provided herein for treating or preventing a senescence-associated disease by administering to a subject in need thereof a senolytic combination that comprises two small molecule compounds, such as dasatinib and quercetin or an analog thereof When used alone, at least one or both of the small molecule compounds in a senolytic combination has insufficient senolytic activity to selectively kill senescent cells and provide a therapeutic effect. Each compound may alter either a cell survival signaling pathway or an inflammatory pathway or both the cell survival signaling pathway and the inflammatory pathway in a senescent cell. For convenience, when two or more compounds are described herein as being used in combination, one compound may be called a first agent or first compound, and another compound may be called the second agent or second compound, etc. In other certain embodiments, the methods described herein comprise administering at least three compounds (a first agent, second agent, and third agent). The adjectives, first, second, third, and such, in this context are used for convenience only and are not to be construed as describing order or administration, preference, or level of activity or other parameter unless expressly described otherwise. Use of the at least two compounds results in significantly increased killing of senescent cells compared with use of each compound alone.

As described in greater detail herein, a senolytic combination may alter a signaling pathway such as a cell survival signaling pathway. Each agent of the combination may alter one or more cell survival signaling pathways, for example, a Src kinase signaling pathway, a PI3K/Akt pathway, PI3K/Akt/mTor pathway, p38/MAPK pathway, ERK/MAPK pathway, mTOR pathway, insulin/IGF-1 signaling pathway, or a TGF-13 signaling pathway. The agent may instead alter or also alter an inflammatory pathway. Examples of inflammatory pathways that may be altered by an agent of a senolytic combination include one or more of a p38/MAPK signaling pathway, ERK/MAPK pathway, a Src kinase signaling pathway, or an NF-κB pathway. In certain embodiments, an agent of the combination or the combination alters one or more of a p38/MAPK signaling pathway, ERK/MAPK pathway, or a Src kinase signaling pathway. Depending on the specific cellular polypeptide with which an agent of the combination directly interacts in the p38/MAPK signaling pathway, ERK/MAPK pathway, or Src kinase signaling pathway, the pathway affected may be either one or both of a cell survival pathway or an inflammatory pathway.

Scnolytic combinations described herein that may alter at least one signaling pathway may comprise an agent that inhibits an activity of at least one of a src kinase, Akt kinase, ERK MAPK, p38 MAPK, histone deacetylase (HDAC), polar auxin transporter, monamine oxidase (MAO), protein kinase C-beta, calcineurin, and calmodulin. In certain embodiments, an agent of the combination can alter at least one or at least two signaling pathways by inhibiting two or more signaling pathway components. The agent or combination of agents may inhibit two or more of a src kinase, Akt kinase, ERK MAPK, p38 MAPK, histone deacetylase (HDAC), polar auxin transporter, monoamine oxidase (MAO), calcineurin, and calmodulin.

In certain embodiments, methods are provided wherein the senolytic combination alters either a cell survival signaling pathway or an inflammatory pathway or alters both the cell survival signaling pathway and the inflammatory pathway in a senescent cell. In other particular embodiments, methods comprise use of a senolytic combination that comprises at least two agents wherein at least one agent and a second agent are each different and independently alter either one or both of a survival signaling pathway and an inflammatory pathway.

Senolytic combinations that may be used in the methods for treating or preventing a senescence cell associated disorder described herein include, but are not limited to, small organic molecules. A small molecule compound of interest may be derivatized, either randomly or by SAR, to obtain analog compounds with an improved bioavail ability, pharmacokinetic characteristic, or other characteristic (e.g., solubility, stability). Small organic molecules typically have molecular weights less than 10' daltons, less than $10^4$ daltons, or less than $10^3$ daltons. In certain embodiments, a small molecule compound does not violate the following criteria more than once: (1) no more than 5 hydrogen bond donors (the total number of nitrogen—hydrogen and oxygen—hydrogen bonds); (2) not more than 10 hydrogen bond acceptors (all nitrogen or oxygen atoms); (3) a molecular mass less than 500 daltons; (4) an octanol-water partition coefficient[5] log P not greater than 5.

In yet another embodiment, the senolytic combination used in the methods described herein for treating a senescence associated disease or disorder comprises a flavonoid, such as quercetin or an analog thereof and a src inhibitor (e.g., dasatinib). In a particular embodiment, the small molecule compound has a structure of formula (I) as described below, which includes quercetin and analogs thereof.

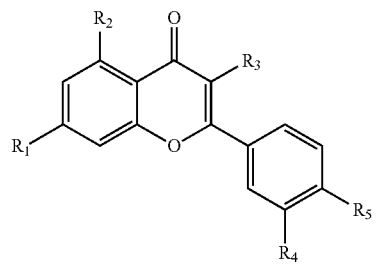

Formula (I)

or a pharmaceutically acceptable salt, stereoisomer, tautomer, or prodrug thereof, wherein
$R_1$ is —OH or H;
$R_2$ is —OH or H;
$R_3$ is —OH, H, $R_6$, or —OCH$_2$PO(OH)$_2$;
$R_4$ is —OH, —OPO(OH)(O—), —OCH$_3$, —OCH$_2$PO(OH)$_2$, $R_6$, H, or —OSO$_3$—; and
$R_5$ is —OH, H, $R_6$, or —OCH$_3$,
wherein $R_6$ is

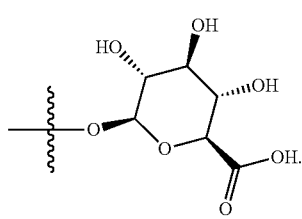 [SMILES: *O[C@@H]1O[C@H](C(=O)O)[C@@H](O)[C@H](O)[C@H]1O]

In certain embodiments, $R_1$ is —OH. In other certain embodiments, $R_1$ is H.

In certain embodiments, $R_2$ is —OH. In other certain embodiments, $R_2$ is H.

In certain embodiments, $R_3$ is —OH. In other certain embodiments, $R_3$ is H. In still other specific embodiments, $R_3$ is —OCH$_2$PO(OH)$_2$.

In other specific embodiments, $R_4$ is —OH, —OPO(OH)(O$^-$), —OCH$_3$, —OCH$_2$PO(OH)$_2$; $R_6$, or —OSO$_3^-$. In another particular embodiment, $R_4$ is —OH, —OPO(OH)(O), —OCH$_2$PO(OH)$_2$, $R_6$, or —OSO$_3$. In certain particular embodiments, $R_4$ is —OH, $R_6$, or —OSO$_3^-$. In a more specific embodiment, $R_4$ is —OH. In other specific embodiments, $R_4$ is —OPO(OH)(O). In yet other specific embodiments, $R_4$ is In other specific embodiments, $R_4$ is —OCH$_2$PO(OH)$_2$. In still a more specific embodiment, $R_4$ is $R_6$. In still another embodiment, $R_4$ is —OCH$_3$.

In other particular embodiments, $R_5$ is —OH or —OCH$_3$. In certain particular embodiments, $R_5$ is —OH. In another embodiment, $R_5$ is H. In other particular embodiments, $R_5$ is $R_6$.

In one embodiment, the compound of formula (I) has the structure of formula (Ia):

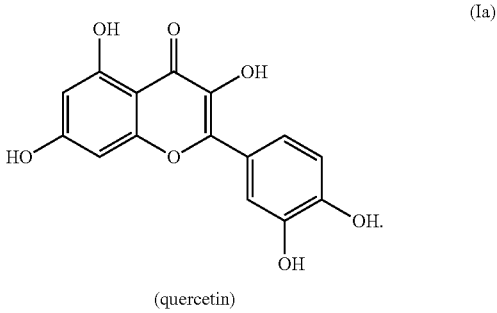 [SMILES: O=c1c(O)c(-c2ccc(O)c(O)c2)oc2cc(O)cc(O)c12]

(quercetin)

In another embodiment, the compound of formula (I) has the structure of formula (Ib):

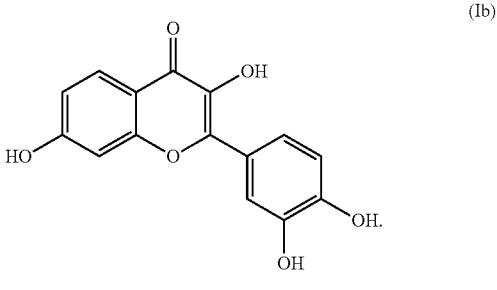

(fisetin)

In another specific embodiment, the compound of formula (I) has the structure of formula (Ic):

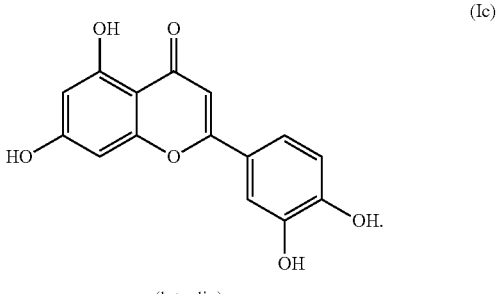

(luteolin)

In still another specific embodiment, the compound of formula (I) has the structure of formula (Id):

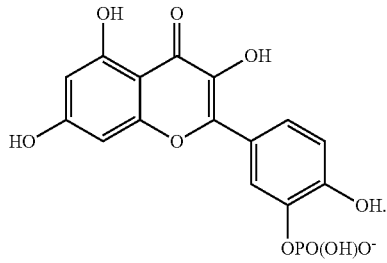
(Id)

In a particular embodiment, the pharmaceutically acceptable salt of the compound of structure (Id) is a sodium salt.

In another specific embodiment, the compound of formula (I) has the structure of formula (Ie):

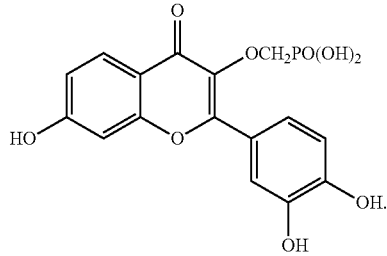
(Ie)

In another specific embodiment, the compound of formula (I) has the structure of formula (If):

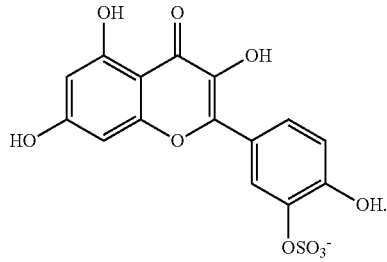
(If)

In a particular embodiment, the pharmaceutically acceptable salt of the compound of structure (If) is a potassium salt.

In another particular embodiment, the compound of formula I has the structure of formula (Ig):

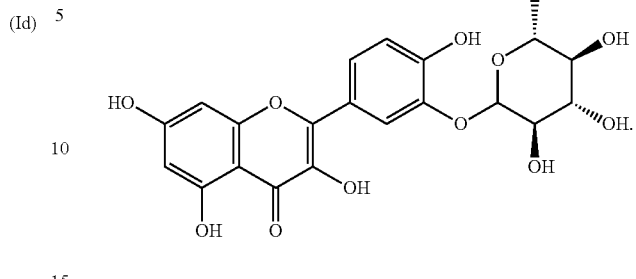
(Ig)

This compound may also be referred to herein as quercetin-3'-glucuronide. In a certain particular embodiment, the pharmaceutically acceptable salt of the compound of structure (Ig) is a sodium salt.

Quercetin, fisetin, and luteolin (compounds of structure (Ia), (Ib), and (Ic), respectively) are flavonoids found in plants and have been studied for their potential therapeutic properties. Quercetin is a flavonoid that is present in fruits and vegetables including apples; black, green and buckwheat tea; onions; red grapes; cherries; raspberries; and citrus fruits and in some plants including *Ginkgo biloba* and St. John's Wort. A naturally occurring analog of quercetin that may be used in a senolytic combination in the methods described herein is fisetin, which is found in a variety of trees, shrubs, fruits, and vegetables, herbs, and teas. Luteolin is a flavone and is also found in plants. Reports suggest that luteolin has anti-inflammatory activity; however, its biological activities have been less extensively studied than those of quercetin or fisetin. With respect to the methods and uses for treating senescence cell associated diseases and disorders as described herein, the methods are not intended to include administration of natural occurring compounds, e.g., quercetin or fisetin, or luteolin, by administering plants, foods, or drinks that naturally contain quercetin.

Quercetin has been described in the art as being capable of inhibiting src kinase, Akt kinase, histone deacetylase (HDAC), aldose reductase, and low-density lipoprotein oxidation. Quercetin can act as a calmodulin antagonist and it also inhibits cyclooxygenase and lipooxygenase and certain phospholipases. Fisetin acts as a sirtuin-activating compound (STAC), and thus has an effect on sirtuins, a group of enzymes that use NAD+ to remove acetyl groups from proteins. Fisetin may act as a caloric restriction mimetic. The compounds of formula (I), (i.e., quercetin and analogs described herein) may alter any one or more of a Src kinase signaling pathway, a PI3K/Akt pathway, a P38/MAPK pathway, and an insulin/IGF-1 signaling pathway.

Isolated compounds of formula (I) (e.g., compounds of formula (Ia), (Ib), (Ic), (Id), (Ie), (If), and (Ig)) may be prepared by chemical synthetic methods according to any one or more synthesis methods known and routinely practiced in the chemical art. Alternatively, quercetin or other natural analogs, such as fisetin and luteolin, may be isolated from a plant, fruit, or vegetable to obtain highly purified quercetin (e.g., >95%, 96%, 97%, 98% or greater than 99% purity).

With regard to stereoisomers of quercetin and its analogs, the compounds may have one or more chiral (or asymmetric) centers, and may thus give rise to enantiomers, diastereomers, and other stereoisomeric forms that may be defined, in terms of absolute stereochemistry, as (R)- or (S)-. When the compounds described herein contain olefinic double bonds or other centers of geometric asymmetry, and unless specified otherwise, it is intended that the compounds include both E and Z geometric isomers (e.g., cis or trans). Likewise, unless otherwise specified, all possible isomers, as well as their racemic and optically pure forms, and all tautomeric forms are also intended to be included. It is therefore contemplated that various stereoisomers and mixtures thereof and includes "enantiomers," which refers to two stereoisomers whose molecules are nonsuperimposeable mirror images of one another. Thus, the compounds may occur in any isomeric form, including racemates, racemic mixtures, and as individual enantiomers or di astereomers. A "tautomer" refers to a proton shift from one atom of a molecule to another atom of the same molecule. Some embodiments of the compounds include tautomers of the compound.

Quercetin or an analog thereof may be used as a "prodrug," meant to indicate a compound that may be converted under physiological conditions or by solvolysis to a biologically active compound. Thus, the term "prodrug" refers to a metabolic precursor of a compound that is pharmaceutically acceptable. A prodrug may be inactive when administered to a subject in need thereof, but is converted in vivo to an active compound as described herein. Prodrugs are typically rapidly transformed in vivo to yield the parent compound, for example, by hydrolysis in blood. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam). A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein.

The term "prodrug" is also meant to include any covalently bonded carriers which release the active compound as described herein in vivo when such prodrug is administered to a mammalian subject. Prodrugs of a compound may be prepared by modifying functional groups present in the compound in such a way that the modifications are cleaved, either in routine manipulation or in vivo, to the parent compound described herein. Prodrugs include compounds wherein a hydroxy, amino or mercapto group is bonded to any group that, when the prodrug of the compound is administered to a mammalian subject, cleaves to form a free hydroxy, free amino or free mercapto group, respectively. Examples of prodrugs include, but are not limited to, ester and amide derivatives of hydroxy, carboxy, mercapto or amino functional groups in the compounds and the like.

To form a senolytic combination, quercetin or an analog thereof may be combined with a small molecule compound that alters a protein tyrosine kinase pathway. In certain embodiments, the protein kinase tyrosine pathway is altered by a compound that directly inhibits a protein tyrosine kinase (e.g., Src, Lck, Yes, Fyn). In certain embodiments, the compound used in the senolytic combination inhibits a Src protein kinase. An example of such a Src kinase inhibitor is dasatinib ((N-(2-chloro-6-methylphenyl)-2-[[6-[4-(2-hydroxyethyl)-1-piperazinyl]-2-methyl-4-pyrimidinyl]lamino]-5-thiazole carboxamide monohydrate) (SPRYCEL) (Bristol-Myers Squibb, New York, N.Y.). Dasatinib inhibits the Bcr-abl and src family of kinases, which includes Src, Lck, Yes, and Fyn. It is also described as affecting c-Kit (CD117), Pha2, and inhibits PDGFR-beta. Dasatinib has been approved by regulatory agencies for treating Philadelphia chromosome+chronic myelogenous leukemia (CP-CML); and for treating chronic, accelerated or myeloid or lymphoid blast phase Ph+ CML resistant/intolerant to prior therapy that included imatinib; and Ph+ ALL (acute lymphoblastic leukemia) with resistance to intolerance prior to therapy. Dasatinib analogs include compounds described in U.S. Pat. Nos. 6,596,746; 7,125,875; 7,153,856; 7,491,725, which patents arc all herein incorporated by reference in their entirety. Processes for making dasatinib and analogs thereof may be performed by persons skilled in the art using methods and techniques routinely practiced in the art and as described in U.S. Pat. Nos. 6,596,746; 7,125,875; 7,153,856; 7,491,725. Dasatinib may affect any one or more of a Src kinase signaling pathway, a PI3K/Akt pathway, a P13K pathway, a P38/MAPK pathway, and an ERK/MAPK pathway. Other compounds classified as BCR-ABL inhibitors, such as imatinib and sorafenib, are not Src inhibitors and arc significantly less effective for use in the methods described herein.

Another example of a small molecule agent that may be included in a senolytic combination is enzastaurin, which is a protein kinase C-beta (PKCI3) inhibitor. Enzastaurin (3-(1-Methylindol-3-yl)-4-[1-[1-(pyridin-2-ylmethyl)piperidin-4-yl]indol-3-yl]pyrrole-2,5-dione) (LY317615; Eli Lilly and Company, Indianapolis, Ind.) (see U.S. Pat. No. 5,668, 152) is a serine/threonine kinase inhibitor that inhibits protein kinase C beta (PKC-(3) and inhibits the AKT pathway, which induces apoptosis of cancer cells. PKC-f3 mediates VEGFR2 signaling through MEK and MAP kinase activation. By activating Akt through phosphorylation, PKC-I3 interacts with the phosphatase and tensin homolog (PTEN)/PI3K/Akt pathway. In a particular embodiment, a PKC-13 inhibitor, such as enzastaurin, is combined with a compound of formula I, such as quercetin or an analog thereof, for use in the methods for treating or preventing a senescence cell associated disease or disorder, which in certain embodiments is not a cancer.

Also as described herein, in particular embodiments, when two or more agents are used in combination for treatment or prophylaxis of a senescence-associated disease or disorder, any one of the compounds of formula (I) (e.g., a compound of formula (Ia), (Ib), (Ic), (Id), (Ie), (If), and (Ig)) may be combined with a second compound, such as by way of non-limiting example, dasatinib or an analog thereof, or enzastaurin or an analog thereof In other specific embodiments, any one of the compounds of formula (I) (e.g., a compounds of formula (Ia), (Ib), (Ic), (Id), (Ie), (If), and (Ig)) may be combined with a second and a third compound, such as by way of non-limiting example, dasatinib or an analog thereof, and enzastaurin or an analog thereof.

Quercetin analogs that may be used in the methods for treating a senescent cell associated disease or disorder described herein include a compound having a structure of formula (Tb) (fisetin), (Ic) (luteolin), (Id), (Te), (If), or (Ig). In certain embodiments, two or more compounds of formula (I) may be used in these methods in combination with a third agent, such as dasatinib. By way of example, the two or more compounds of formula (I) may include a combination of quercetin (Ia) with any one of a compound having the structure of formula (Ib), (Ic), (Id), (Ie), (If), or (Ig) and a third agent that is not quercetin or an analog thereof. In other embodiments, the methods described herein may comprise use of any two compounds of formula (I), independently selected from compounds of formula (Ia), (Tb), (Ic), (Id), (Ie), (If), and (Ig) and a third agent that is not quercetin or an analog thereof. In still other embodiments, any two or all three of quercetin, fisctin, and lutcolin may be used in these methods in combination with a non-quercetin agent, such as dasatinib. In other embodiments, a combination of quercetin and fisetin and a third agent that is not quercetin or an analog thereof, such as dasatinib is used in the methods described herein.

The compounds described herein may generally be used as the free acid or free base. Alternatively, the compounds may be used in the form of acid or base addition salts. Acid addition salts of the free base amino compounds may be prepared according to methods well known in the art, and may be formed from organic and inorganic acids. Suitable organic acids include (but are not limited to) maleic, fumaric, benzoic, ascorbic, succinic, methanesulfonic, acetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include (but are not limited to) hydrochloric, hydrobromic, sulfuric, phosphoric, and nitric acids. Base addition salts of the free acid compounds of the compounds described herein may also be prepared by methods well known in the art, and may be formed from organic and inorganic bases. Suitable inorganic bases included (but are not limited to) the hydroxide or other salt of sodium, potassium, lithium, ammonium, calcium, magnesium, iron, zinc, copper, manganese, aluminum, and the like, and organic bases such as substituted ammonium salts. Thus, the term "pharmaceutically acceptable salt" of compounds described herein is intended to encompass any and all pharmaceutically suitable salt forms.

Compounds may sometimes be depicted as an anionic species. One of ordinary skill in the art will recognize that the compounds exist with an equimolar ratio of cation. For instance, the compounds described herein can exist in the fully protonated form, or in the form of a salt such as sodium, potassium, ammonium or in combination with any inorganic base as described above. When more than one anionic species is depicted, each anionic species may independently exist as either the protonated species or as the salt species. In some specific embodiments, the compounds described herein exist as the sodium salt. In other specific embodiments, the compounds described herein exist as the potassium salt.

Furthermore, some of the crystalline forms of any compound described herein may exist as polymorphs, which are also included and contemplated by the present disclosure. In addition, some of the compounds may form solvates with water or other organic solvents. Often crystallizations produce a solvate of the disclosed compounds. As used herein, the term "solvate" refers to an aggregate that comprises one or more molecules of any of the disclosed compounds with one or more molecules of solvent. The solvent may be water, in which case the solvate may be a hydrate.

Alternatively, the solvent may be an organic solvent. Thus, the presently disclosed compounds may exist as a hydrate, including a monohydrate, dihydrate, hemihydrate, sesquihydrate, trihydrate, tetrahydrate and the like, as well as the corresponding solvated forms. Certain embodiments of the compounds may be true solvates, while in other cases, some embodiments of the compounds may merely retain adventitious water or be a mixture of water plus some adventitious solvent.

Specific and analogous reactants may also be identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs may be prepared by custom chemical synthesis houses, where many of the standard chemical supply houses (e.g., those listed above) provide custom synthesis services. A reference for the preparation and selection of pharmaceutical salts of the present disclosure is P. H. Stahl & C. G. Wermuth "Handbook of Pharmaceutical Salts," Verlag Helvetica Chimica Acta, Zurich, 2002. Methods known to one of ordinary skill in the art may be identified through various reference books and databases. Suitable reference books and treatises detail the synthesis of reactants useful in the preparation of compounds described herein, or provide references to articles that describe the preparation.

In general, the compounds used in the methods described herein may be made according to organic synthesis techniques known to those skilled in this art, starting from commercially available chemicals and/or from compounds described in the chemical literature.

Assays and techniques for identifying senolytic combinations are described in greater detail herein. In addition, identifying and selecting small compounds for use in senolytic combinations, a person skilled in the medicinal chemistry art may also consider other properties of a small molecule, such as solubility, bioavailability, pharmacokinetics, Lipinski Rule of 5, and the like.

Senescent Cells

A senolytic agent and a senolytic combination selectively kills or destroys senescent cells in a clinically significant or biologically significant manner. A senolytic combination may selectively kill one or more types of senescent cells (e.g., senescent preadipocytes, senescent endothelial cells, senescent fibroblasts, senescent neurons, senescent epithelial cells, senescent chondrocytes, senescent mesenchymal cells, senescent macrophages, senescent smooth muscle cells). In certain embodiments, a senolytic combination is capable of selectively killing at least senescent preadipocytes. Senolytic combinations that selective kill preadipocytes may be useful for treatment or prophylaxis of diabetes (particularly type 2 diabetes), metabolic syndrome, or obesity. In other embodiments, a senolytic combination is capable of selectively killing at least senescent endothelial cells. Such senolytic combinations may be useful for treatment or prophylaxis or a cardiovascular disease (e.g., atherosclerosis). In other particular embodiments, a senolytic combination is capable of selectively killing at least senescent fibroblasts. In still another embodiment, a senolytic combination may selectively kill at least senescent neurons, including dopamine-producing neurons. In still another embodiment, a senolytic combination may kill at least senescent retinal pigmented epithelial cells or other senescent epithelial cells (e.g., pulmonary senescent epithelial cells or senescent kidney epithelial cells). Selective killing of pulmonary epithelial cells may be useful for treating pulmonary diseases, such as chronic obstructive pulmonary disease. In yet other embodiments, a senolytic combination may selectively kill at least senescent immune cells (e.g., senescent macrophages). In still another embodiment, a senolytic combination may kill at least chondrocytes, which may be useful for treatment or prophylaxis of an inflammatory disorder, such as osteoarthritis.

A senescent cell may exhibit any one or more of the following characteristics. (1) Senescence growth arrest is essentially permanent and cannot be reversed by known physiological stimuli. (2) Senescent cells increase in size, sometimes enlarging more than twofold relative to the size of non-senescent counterparts. (3) Senescent cells express a senescence-associated β-galactosidase (SA-β-gal), which partly reflects the increase in lysosomal mass. (4) Most senescent cells express p16INK4a, which is not commonly expressed by quiescent or terminally differentiated cells. (5) Cells that senesce with persistent DDR signaling harbor persistent nuclear foci, termed DNA segments with chromatin alterations reinforcing senescence (DNA-SCARS). These foci contain activated DDR proteins and are distinguishable from transient damage foci. DNA-SCARS include dysfunctional telomeres or telomere dysfunction-induced foci (TIF). (6) Senescent cells express and may secrete molecules associated with senescence, which in certain instances may be observed in the presence of persistent DDR signaling, which in certain instances may be dependent on persistent DDR signaling for their expression. (7) The nuclei of senescent cells lose structural proteins such as Lamin B1 or chromatin-associated proteins such as histones and HMGB1. See, e.g., Freund et al., *Mol. Biol. Cell* 23:2066-75 (2012); Davalos ct al., *J. Cell Biol.* 201:613-29 (2013); Ivanov ct al., *J. Cell Biol.* DOI:10.1083/jcb.201212110, page 1-15; published online Jul. 1, 2013; Funayama et al., *J. Cell Biol.* 175:869-80 (2006)).

Senescent cells and senescent cell associated molecules can be detected by techniques and procedures described in the art. For example, the presence of senescent cells in tissues can be analyzed by histochemistry or immunohistochemistry techniques that detect the senescence marker, SA-beta galactosidase (SA-β gal) (see, e.g., Dimri et al., Proc. Natl. Acad. Sci. USA 92: 9363-9367 (1995)). The presence of the senescent cell-associated polypeptide p16 can be determined by any one of numerous immunochemistry methods practiced in the art, such as immunoblotting analysis. Expression of p16 mRNA in a cell can be measured by a variety of techniques practiced in the art including quantitative PCR. The presence and level of senescence cell associated polypeptides (e.g., polypeptides of the SASP) can be determined by using automated and high throughput assays, such as an automated Luminex array assay described in the art (see, e.g., Coppe et al., *PLoS Biol* 6: 2853-68 (2008)).

The presence of senescent cells can also be determined by detection of senescent cell-associated molecules, which include growth factors, proteases, cytokines (e.g., inflammatory cytokines), chemokines, cell-related metabolites, reactive oxygen species (e.g., H2O2), and other molecules that stimulate inflammation and/or other biological effects or reactions that may promote or exacerbate the underlying disease of the subject. Senescent cell-associated molecules include those that are described in the art as comprising the senescence-associated secretory phenotype (SASP, i.e., which includes secreted factors which may make up the pro-inflammatory phenotype of a senescent cell), senescent-messaging secretome, and DNA damage secretory program (DDSP). These groupings of senescent cell associated molecules, as described in the art, contain molecules in common and are not intended to describe three separate distinct groupings of molecules. Senescent cell-associated molecules include certain expressed and secreted growth factors, proteases, cytokines, and other factors that may have potent autocrinc and paracrinc activities (see, e.g., Coppc et al., supra; Coppe et al. *J. Biol. Chem.* 281:29568-74 (2006); Coppe et al. *PLoS One* 5:39188 (2010); Krtolica et al. *Proc. Natl. Acad. Sci. U.S.A.* 98:12072-77 (2001); Parrinello et al., *J. Cell Sci.* 118:485-96 (2005). ECM associated factors include inflammatory proteins and mediators of ECM remodeling and which are strongly induced in senescent cells (see, e.g., Kuilman et al., *Nature Reviews* 9:81-94 (2009)). Other senescent cell-associated molecules include extracellular polypeptides (proteins) described collectively as the DNA damage secretory program (DDSP) (see, e.g., Sun et al., *Nature Medicine* published online 5 Aug. 2012; doi:10.1038/nm.2890). Senescent cell-associated proteins also include cell surface proteins (or receptors) that are expressed on senescent cells, which include proteins that are present at a detectably lower amount or are not present on the cell surface of a non-senescent cell.

Senescence cell-associated molecules include secreted factors which may make up the pro-inflammatory phenotype of a senescent cell (e.g., SASP). These factors include, without limitation, GM-CSF, GROα, GROα,β,γ, IGFBP-7, IL-1α, IL-6, 1L-7, 1L-8, MCP-1, MCP-2, MIP-1α, MMP-1, MMP-10, MMP-3, Amphiregulin, ENA-78, Eotaxin-3, GCP-2, GITR, HGF, ICAM-1, IGFBP-2, IGFBP-4, IGFBP-5, IGFBP-6, IL-13, IL-1β, MCP-4, MIF, MIP-3α, MMP-12, MMP-13, MMP-14, NAP2, Oncostatin M, osteoprotegerin, PIGF, RANTES, sgp130, TIMP-2, TRAIL-R3, Acrp30, angiogenin, Axl, bFGF, BLC, BTC, CTACK, EGF-R, Fas, FGF-7, G-CSF, GDNF, HCC-4, 1-309, IFN-γ, IGFBP-1, IGFBP-3, IL-1R1, IL-11, IL-15, IL-2R-α, TL-6R, I-TAC, Leptin, LIF, MMP-2, MSP-a, PAI-1, PAI-2, PDGF-BB, SCF, SDF-1, sTNF RI, sTNF R11, Thrombopoietin, T1MP-1, tPA, uPA, uPAR, VEGF, MCP-3, 1GF-1, TGF-133, MIP-1-delta, IL-4, FGF-7, PDGF-BB, IL-16, BMP-4, MDC, MCP-4, IL-10, TIMP-1, Fit-3 Ligand, ICAM-1, Axl, CNTF, INF-γ, EGF, BMP-6. Additional identified factors, which include those sometimes referred to in the art as senescence messaging secretome (SMS) factors, some of which are included in the listing of SASP polypeptides, include without limitation, IGF1, IGF2, and IGF2R, IGFBP3, IDFBP5, IGFBP7, PAll, TGF-13, WNT2, IL-1a, IL-6, IL-8, and CXCR2-binding chemokines. Cell-associated molecules also include without limitation the factors described in Sun et al., Nature Medicine, supra, and include, including, for example, products of the genes, MMP1, WNT16B, SFRP2, WP12, SPINK1, MMP10, ENPP5, EREG, BMP6, ANGPTL4, CSGALNACT, CCL26, AREG, ANGPT1, CCK, THBD, CXCL14, NOV, GAL, NPPC, FAM150B, CST], GDNF, MUCL1, NPTX2, TMEM155, EDN1, PSG9, ADAMTS3, CD24, PPBP, CXCL3, MMP3, CST2, PSG8, PCOLCE2, PSG7, TNFSFJ5, C17,91167, CALCA, FGF18, IL8, BMP2, MATN3, TFP1, SERPINI 1, TNFRSF25, and IL23A. Senescent cell-associated proteins also include cell surface proteins (or receptors) that are expressed on senescent cells, which include proteins that are present at a detectably lower amount or are not present on the cell surface of a non-senescent cell.

Methods for Characterizing and Identifying Senolytic Combinations

Characterizing a senolytic combination can be determined using one or more cell-based assays and one or more animal models described herein or in the art and with which a person skilled in the art will be familiar. A senolytic combination may selectively kill one or more types of senescent cells (e.g., senescent preadipocytes, senescent endothelial cells, senescent fibroblasts, senescent neurons, senescent epithelial cells, senescent mesenchymal cells, senescent smooth muscle cells, senescent macrophages, or senescent chondrocytes).

A person skilled in the art will readily appreciate that characterizing a combination of agents and determining the level of killing by the combination can be accomplished by comparing the activity of a test agent or combination with appropriate negative controls (e.g., vehicle only and/or a composition or compound known in the art not to kill senescent cells) and appropriate positive controls. In vitro cell-based assays for characterizing senolytic combinations also include controls for determining the effect of an agent and combination comprising the agent on non-senescent cells (e.g., quiescent cells or proliferating cells). A senolytic combination reduces (i.e., decreases) percent survival of a plurality of senescent cells (i.e., in some manner reduces the quantity of viable senescent cells in the animal or in the cell-based assay) compared with one or more negative controls. Conditions for a particular in vitro assay include temperature, buffers (including salts, cations, media), and other components, which maintain the integrity of the test agent and reagents used in the assay, and which are familiar to a person skilled in the art and/or which can be readily determined.

The source of senescent cells for use in assays may be a primary cell culture, or culture adapted cell line, including but not limited to, genetically engineered cell lines that may contain chromosomally integrated or episomal recombinant nucleic acid sequences, immortalized or immortalizable cell lines, somatic cell hybrid cell lines, differentiated or differentiatable cell lines, transformed cell lines, and the like. In a particular embodiment, the senescent cell is isolated from biological sample obtained from a host or subject who has a senescent cell associated disease or disorder. In other embodiments, non-senescent cells, which may be obtained from a subject or may be a culture adapted line may be used and senescence induced by methods described herein and in the art, such as by exposure to irradiation or a chemotherapeutic agent (e.g., doxorubicin). The biological sample may be a blood sample, biopsy specimen, body fluids (e.g., lung lavage, ascites, mucosal washings, synovial fluid), bone marrow, lymph nodes, tissue explant, organ culture, or any other tissue or cell preparation from a subject. The sample may be a tissue or cell preparation in which the morphological integrity or physical state has been disrupted, for example, by dissection, dissociation, solubilization, fractionation, homogenization, biochemical or chemical extraction, pulverization, lyophilization, sonication, or any other means for processing a sample derived from a subject or biological source. The subject may be a human or non-human animal.

Transgenic animal models as described herein and in the art may be used to determine killing or removal of senescent cells (see, e.g., Baker et al., supra; *Nature*, 479:232-36 (2011); Int'l Patent Application Publication No. WO/2012/177927; Intl Patent Application Publication No. WO 2013/090645). Exemplary transgenic animal models contain a transgene that includes a nucleic acid that allows for controlled clearance of senescence cells (e.g., p $16^{ink4a}$ positive senescent cells) as a positive control. The presence and level of senescent cells in the transgenic animals can be determined by measuring the level of a detectable label or labels that are expressed in senescent cells of the animal. The transgene nucleotide sequence includes a detectable label, for example, one or more of a red fluorescent protein; a green fluorescent protein; and one or more luciferases to detect clearance of senescent cells.

Animal models that are described herein or in the art includes art-accepted models for determining the effectiveness of a senolytic combination to treat or prevent (i.e., reduce the likelihood of occurrence of) a particular senescence associated disease or disorder, such as atherosclerosis models, osteoarthritis models, COPD models, and IPF models. As described herein, pulmonary disease murine models, such as a bleomycin pulmonary fibrosis model, and a chronic cigarette smoking model are applicable for diseases such as COPD and may be routinely practiced by a person skilled in the art. Animal models for determining the effectiveness of a senolytic combination to treat and/or prevent (i.e., reduce the likelihood of occurrence of) chemotherapy and radiotherapy side effect models or to treat or prevent metastasis are described in International Patent Application Publication Nos. WO 2013/090645 and WO 2014/205244, which are incorporated herein by reference in their entirety. Animal models for determining the effectiveness of combinations for treating eye diseases, particularly age-related macular degeneration are also routinely used in the art (see, e.g., Pennesi et al., *Mol. Aspects Med.* 33:487-509 (2012); Zeiss et al., *Vet. Pathol.* 47:396-413 (2010); Chavala et al., *J. Clin. Invest.* 123:4170-81 (2013)).

By way of non-limiting example and as described herein, ostcoarthritis animal models have been developed. Osteoarthritis may be induced in the animal, for example, by inducing damage to a joint, for example, in the knee by surgical severing, incomplete or total, of the anterior cruciate ligament. By way of another non-limiting example and as described herein, atherosclerosis animal models have been developed. Atherosclerosis may be induced in the animal, for example, by feeding animals a high fat diet or by using transgenic animals highly susceptible to developing atherosclerosis. In still another example, and as described herein, mouse models in which animals arc treated with bleomycin has been described (see, e.g., Peng et al., i PLoS One 2013; 8(4):e59348. doi: 10.1371/journal.pone.0059348. Epub 2013 Apr. 2; Mouratis et al., *Curr. Opin. Pubn. Med.* 17:355-61 (2011)) for determining the effectiveness of an agent for treating IPF.

In pulmonary disease animals models (e.g., a bleomycin animal model, smoke-exposure animal model, or the like), respiratory measurements may be taken to evaluate the usefulness of the senolytic combination. For all the disease models described herein, immunohistology; assays for determining the level of inflammatory molecules (e.g., IL-6) (e.g., immunochemistry, molecular biology techniques); and assays (e.g., immunochemistry, molecular biology techniques) for determining the level of senescence markers as noted above may all be performed according to methods described herein and that may be routinely practiced by the skilled artisan.

Determining the effectiveness of a senolytic combination to selectively kill senescent cells as described herein in an animal model may be performed using one or more statistical analyses with which a skilled person will be familiar. By way of example, statistical analyses such as two-way analysis of variance (ANOVA) may be used for determining the statistical significance of differences between animal groups treated with an agent and those that are not treated with the agent (i.e., negative control group, which may include vehicle only). Statistical packages such as SPSS, MINITAB, SAS, Statistika, Graphpad, GLIM, Genstat, and BMDP are readily available and routinely used by a person skilled in the animal model art.

A person skilled in the art will readily appreciate that characterizing a senolytic combination and determining the level of killing by the combination can be accomplished by comparing the activity of a test agent or combination with appropriate negative controls (e.g., vehicle only and/or a composition, agent, or compound known in the art not to kill senescent cells) and appropriate positive controls. In vitro cell-based assays for characterizing the combination also include controls for determining the effect of the combination on non-senescent cells (e.g., quiescent cells or proliferating cells). A senolytic combination that is useful reduces (i.e., decreases) percent survival of senescent cells (i.e., in some manner reduces the quantity of viable senescent cells in the animal or in the cell-based assay) compared with one or more negative controls. Accordingly, a senolytic combination selectively kills senescent cells compared with killing of non-senescent cells (which may be referred to herein as selectively killing senescent cells over non-senescent cells). In certain embodiments (either in an in vitro assay or in vivo (in a human or non-human animal)), the senolytic combination kills at least 20% of the senescent cells and kills no more than 5% of non-senescent cells. In other particular embodiments (either in an in vitro assay or in vivo (in a human or non-human animal)), the senolytic combination kills at least about 25%, 30%, 35%, 40%, 45%, 50%, 55%, 60%, or 65% of the senescent cells and kills no more than about 5% or 10% of non-senescent cells. In other particular embodiments (either in an in vitro assay or in vivo (in a human or non-human animal)), the senolytic combination kills at least about 30%, 35%, 40%, 45%, 50%, 55%, 60%, or 65% of the senescent cells and kills no more than about 5%, 10%, or 15% of non-senescent cells. In other particular embodiments (either in an in vitro assay or in vivo (in a human or non-human animal)), the senolytic combination kills at least about 40%, 45%, 50%, 55%, 60%, or 65% of the senescent cells and kills no more than about 5%, 10%, 15%, 20%, or 25% of non-senescent cells. In other particular embodiments (either in an in vitro assay or in vivo (in a human or non-human animal)), the senolytic combination kills at least about 50%, 55%, 60%, or 65% of the senescent cells and kills no more than about 5%, 10%, 15%, 20%, 25%, or 30% of non-senescent cells. Stated another way, a senolytic combination has at least 5-25, 10-50 or 10-100 times (5×-25×, 10×-50× or 10×-100×) greater selectively for killing senescent cells than for non-senescent cells (e.g., at least 5×, 10×, 20×, 25×, 30×, 40×, 50×, 60×, 75×, 80×, 90×, or 100×). With respect to specific embodiments of the methods described herein for treating a senescence-associated disease or disorder, the percent senescent cells killed may refer to the percent senescent cells killed in a tissue or organ that comprises senescent cells that contribute to onset, progression, and/or exacerbation of the disease or disorder. By way of non-limiting example, tissues of the brain, tissues and parts of the eye, pulmonary tissue, cardiac tissue, arteries, joints, skin, and muscles may comprise senescent cells that may be reduced in percent as described above by the senolytic combinations described herein and thereby provide a therapeutic effect. Moreover, selectively removing at least 20% or at least 25% of senescent cells from an affected tissue or organ can have a clinically significant therapeutic effect. In certain particular embodiments, in the methods for treating the cardiovascular disease, such as atherosclerosis, as described herein, the scnolytic combination kills at least 20% of the senescent cells and kills no more than 5% of non-senescent cells in the artery. In other particular embodiments, the senolytic combination selectively kills at least 25% of the senescent cells in the arteriosclerotic artery. In another embodiment, with respect to the methods described herein for treating osteoarthritis by administering a senolytic combination, the percent senescent cells killed may refer to the percent senescent cells killed in an osteoarthritic joint versus non-senescent cells killed in the osteoarthritic joint. In certain particular embodiments, in the methods for treating ostcoarthritis as described herein, the at least one senolytic combination kills at least 20% of the senescent cells and kills no more than 5% of non-senescent cells in the osteoarthritic joint. In other particular embodiments, the senolytic combination selectively kills at least 25% of the senescent cells in the osteoarthritic joint. In still another embodiment, with respect to the methods described herein for treating senescence associated pulmonary disease or disorder (e.g., COPD, IPF) by administering a senolytic combination, the percent senescent cells killed may refer to the percent senescent cells killed in affected pulmonary tissue versus non-senescent cells killed in the affected pulmonary tissue of the lung. In certain particular embodiments, in the methods for treating senescence associated pulmonary diseases and disorders as described herein, a senolytic combination kills at least 20% of the senescent cells and kills no more than 5% of non-senescent cells in the affected pulmonary tissue. In other particular embodiments, the senolytic combination selectively kills at least 25% of the senescent cells in the affected pulmonary tissue.

In certain embodiments, methods are provided for identifying (i.e., screening for) combinations that are useful for treating or preventing (i.e., reducing the likelihood of occurrence of) a senescence associated disease or disorder. In one embodiment, a method for identifying a senolytic combination for treating such diseases and disorders, comprises inducing cells to senesce to provide established senescent cells. Methods for inducing cells to senesce are described herein and in the art and include, for example, exposure to radiation (e.g., 10 Gy is typically sufficient) or a chemotherapeutic agent (e.g., doxorubicin or other anthracycline). After exposure to the agent, the cells are cultured for an appropriate time and under appropriate conditions (e.g., media, temperature, $CO_2/O_2$ level appropriate for a given cell type or cell line) to allow senescence to be established. As discussed herein, senescence of cells may be determined by determining any number of characteristics, such as changes in morphology (as viewed by microscopy, for example); production of, for example, senescence-associated 13-galactosidase (SA-(3-gal), p16INK4a, p21, or any one or more SASP factors (e.g., IL-6, MMP3). A sample of the senescent cells is then contacted with a candidate combination (i.e., mixed with, combined, or in some manner permitting the cells and the agent to interact). Persons skilled in the art will appreciate that the assay will include the appropriate controls, negative and positive, either historical or performed concurrently. For example, a sample of control non-senescent cells that have been cultured similarly as the senescent cells but not exposed to a senescence inducing combination are contacted with the candidate agent. The level of survival of the senescent cells is determined and compared with the level of survival of the non-senescent cells. A senolytic combination is identified when the level of survival of the senescent cells is less than the level of survival of the non-senescent cells.

Determining the effectiveness of an agent to kill senescent cells as described herein in an animal model may be performed using one or more statistical analyses with which a skilled person will be familiar. By way of example, statistical analyses such as two-way analysis of variance (ANOVA) may be used for determining the statistical significance of differences between animal groups treated with an agent and those that are not treated with the agent (i.e., negative control group). Statistical packages such as SPSS, MINITAB, SAS, Statistika, Graphpad, GLIM, Genstat, and BMDP are readily available and routinely used by a person skilled in the animal art.

Animal models for these methods and purposes may include non-human primate models, dog models, rodent models, or other animal models appropriate for determining the safety and efficacy of a senolytic agent.

Cell Survival Signaling Pathway and Inflammatory Pathway

The senolytic combinations described herein alter (i.e., interfere with, affect) one or more cellular pathways that are activated during the senescence process of a cell. As described herein, senolytic combinations alter either a cell survival signaling pathway or an inflammatory pathway or alter both a cell survival signaling pathway and an inflammatory pathway in a senescent cell. Without wishing to be bound by theory, activation of certain cellular pathways during senescence decreases or inhibits the cell's capability to induce and ultimately undergo apoptosis. A senolytic combination may alter one or more signaling pathways (e.g., a cell survival pathway and an inflammatory pathway) by interacting with one, two, or more target proteins in the one or more pathways, which results in removing or reducing suppression of a cell death pathway, such as an apoptotic pathway. Contacting or exposing a senescent cell to a senolytic combination to alter one, two, or more cellular pathways in the senescent cell, restores the cell's mechanisms and pathways for initiating apoptosis.

The senolytic combinations described herein alter either a cell survival signaling pathway or an inflammatory pathway or alter both the cell survival signaling pathway and the inflammatory pathway that induces (i.e., initiates, triggers, stimulates or in some manner removes or inhibits suppression of) a cell death pathway, such as an apoptotic pathway, in the senescent cell. Cell survival signaling pathways and inflammatory pathways that are activated during senescence include PI3K/Akt, Src signaling pathway, p38/MAPK, ERK/MAPK pathway, NF-KB signaling, insulin/IGF-1 signaling pathway, TGF-I3 signaling, mTOR pathway, PI3K/Akt/mTor pathway, mTOR/protein translation pathways, among others. A cell survival signaling pathway may include any one or more of a Src kinase signaling pathway, a PI3K/Akt pathway, PI3K/Akt/mTor pathway, p38/MAPK pathway, ERK/MAPK pathway, mTOR pathway, insulin/IGF-1 signaling pathway, or a TGF-I3 signaling pathway, for example. Inflammatory pathways include, by way of non-limiting example, a p38/MAPK signaling pathway, ERK/MAPK pathway, a Src kinase signaling pathway, or an NF-KB pathway.

A cell survival pathway includes the Src signaling pathway, which is involved in regulation of cell proliferation, differentiation, apoptosis, cell adhesion, and stress responses (see, e.g., Wang, *Oncogene* 19:5643-50 (2000); Thomas et al., *Annu. Rev. Cell Dev. Biol.* 13:513-609 (1997)). The Src pathway is also involved in inflammatory responses, including macrophage mediated immune responses (see, e.g., Byeon et al., *Mediators of Inflammation Vol.* 2012, Article ID 512926, doi:10.1155/2012/512926 (2012)) and acute inflammatory responses (see, e.g., Okutani et al., *Am. J. Physiol. Lung Cell Mol. Physiol.* 291:L129-L141 (2006)). Accordingly, a senolytic combination that alters a cell survival pathway that includes altering a Src signaling pathway may also alter an inflammatory pathway.

Figure 2A:
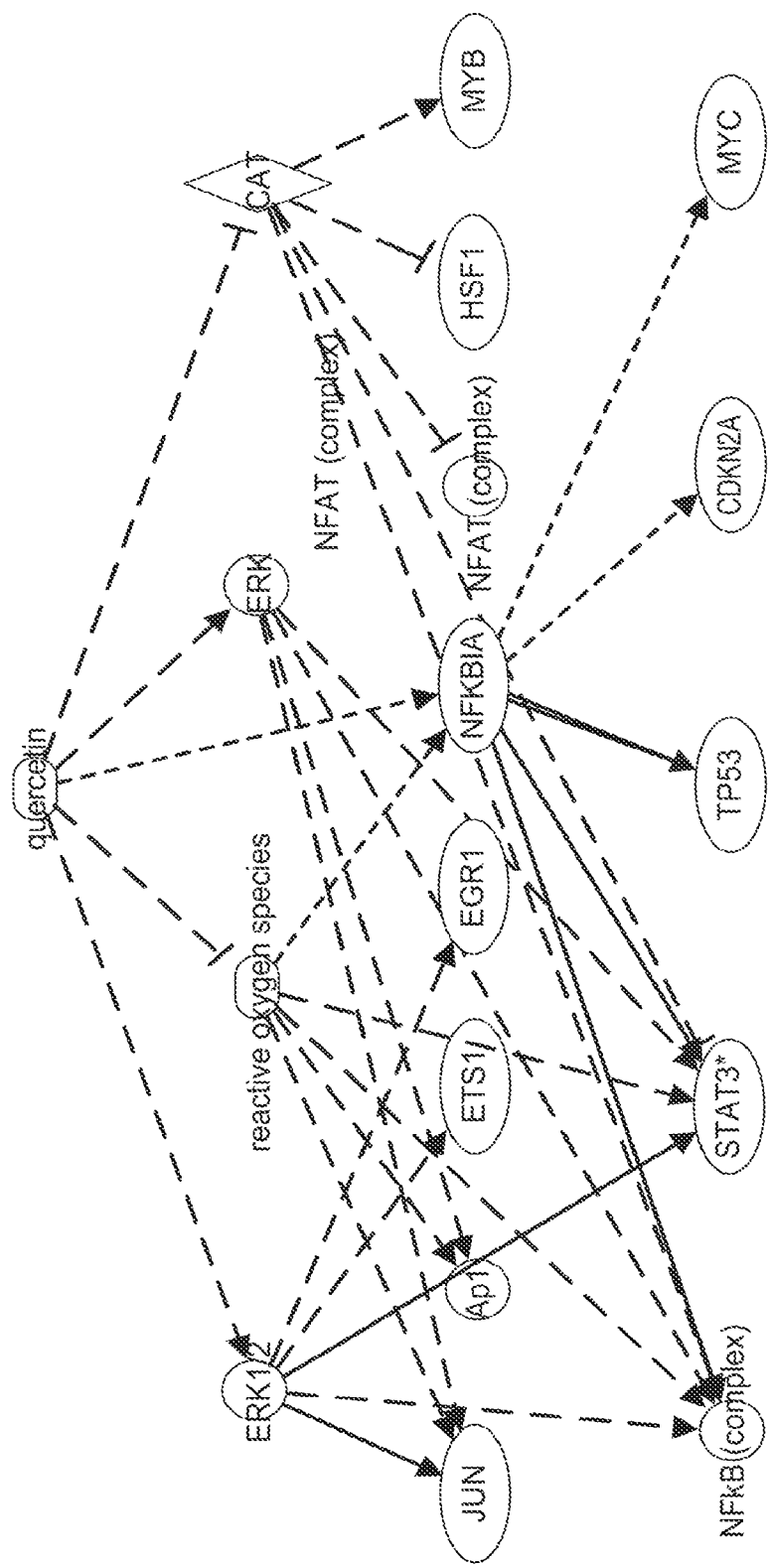
FIGS. 2A-2D illustrate pathways affected by the agents described herein.
Figure 2B:
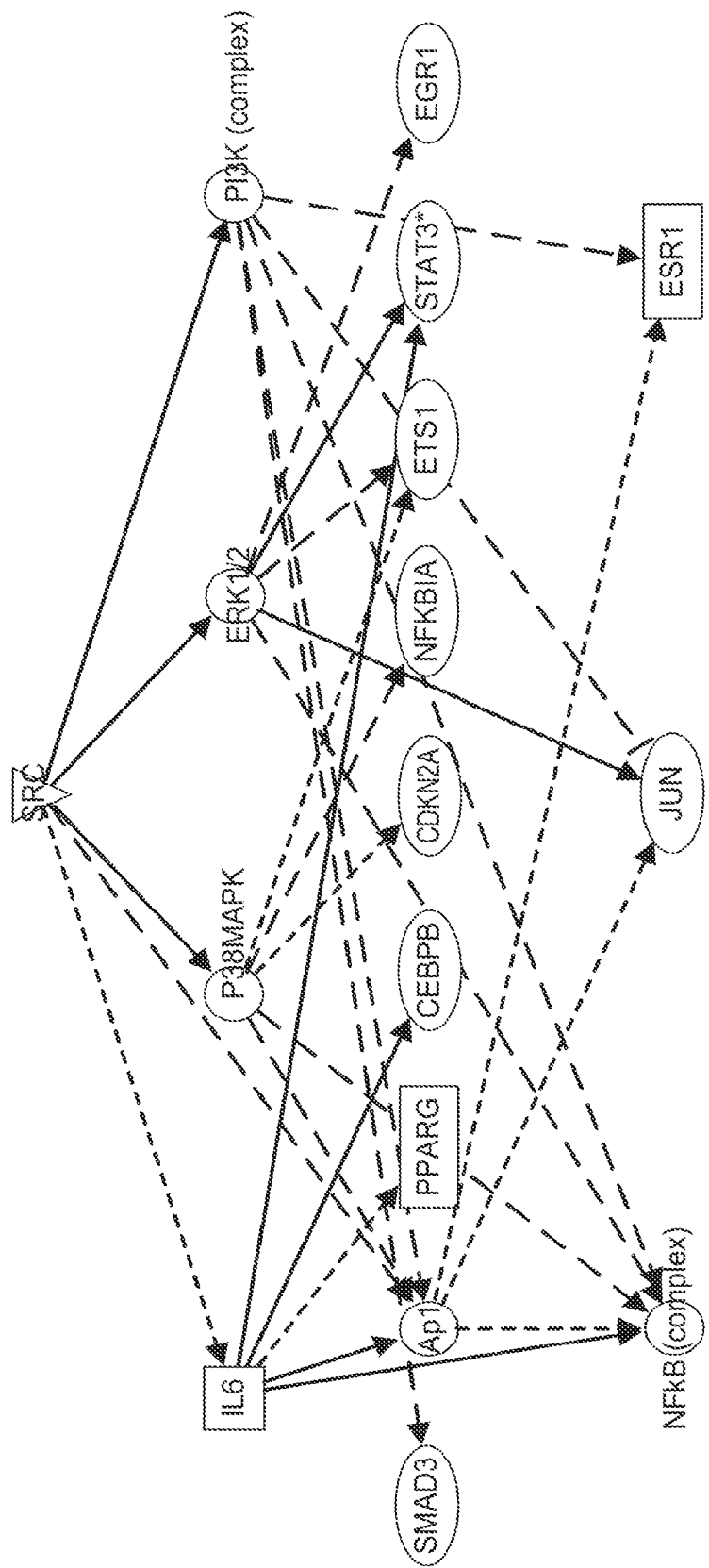
Figure 2C:
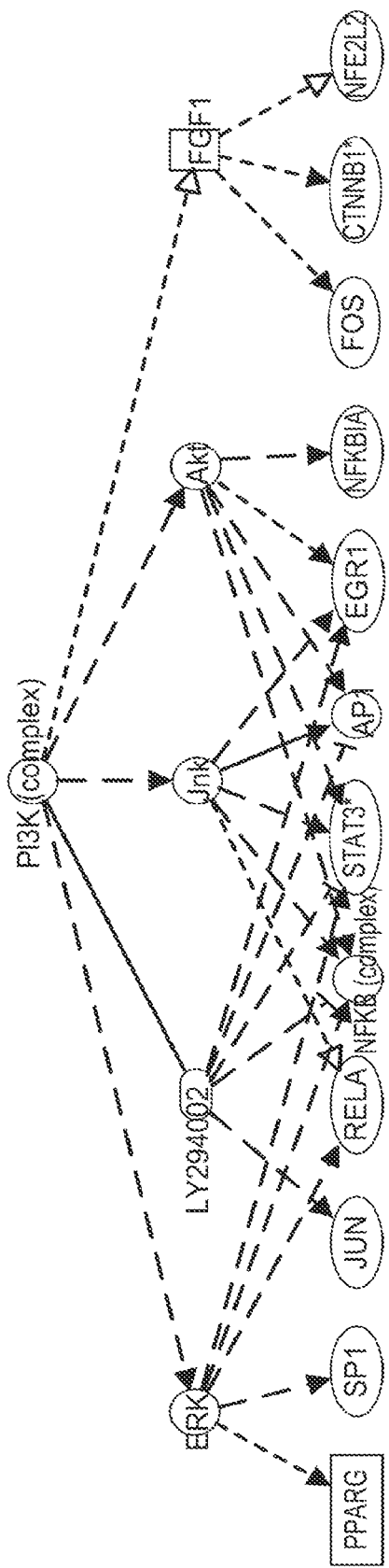
Figure 2D:
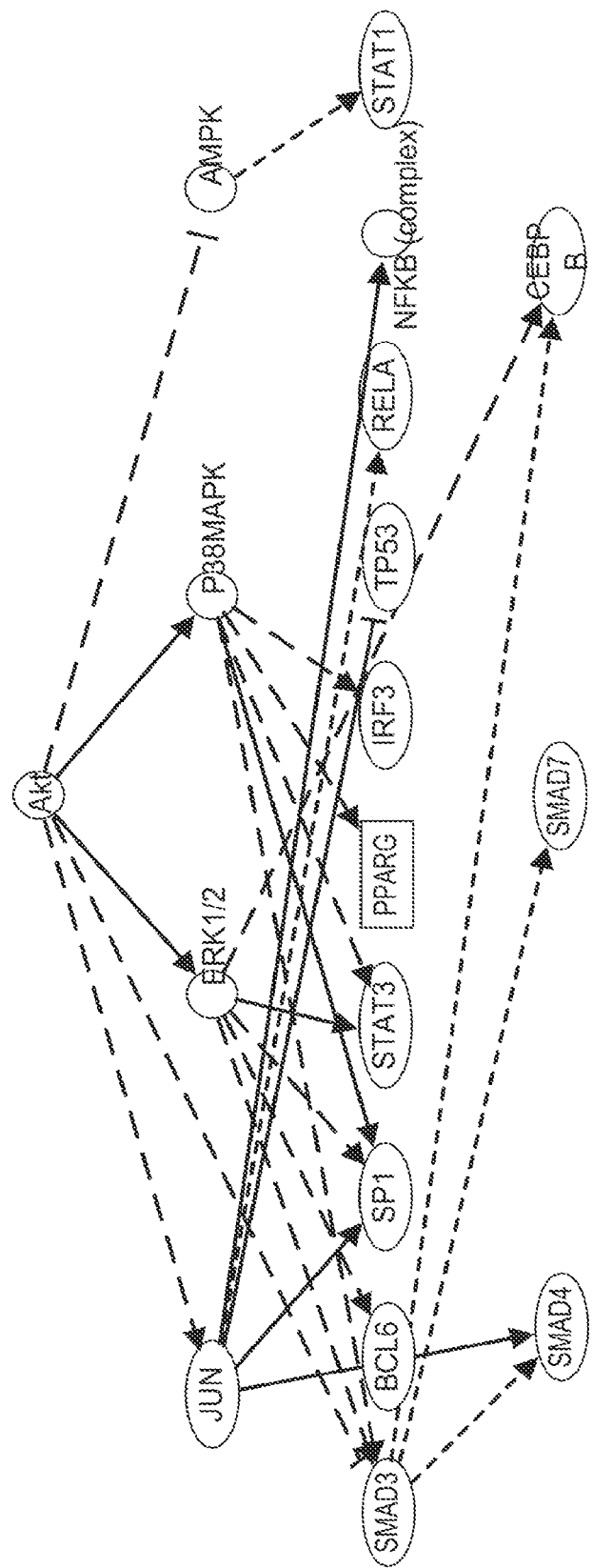

Altering a cell signaling pathway or altering an inflammatory pathway may alter or affect a function of one or more downstream target proteins or may affect the interaction of the one or more downstream target proteins with another component of the respective cell signaling or inflammatory pathway. For example, a senolytic combination that alters a Src kinase pathway or a PI3K/Akt pathway may alter a function of one or more downstream target proteins in the respective pathway or may affect the interaction of the one or more downstream target proteins with another component of the respective pathway (see, e.g., Example 1; FIGS. 2B-2D). Exemplary target proteins that are upregulated in senescent cells include P38/MAPK, ERK1/2, and PI3K (complex). In certain embodiments, the PI3K/Akt pathway, which is a cell signaling pathway, is activated during senescence and a senolytic combination described herein inhibits the pathway, which may enhance induction of apoptosis.

Senescence-Associated Disease or Disorder

Methods are provided herein for treating or preventing (i.e., reducing the likelihood of occurrence) conditions, diseases, or disorders related to, associated with, or caused by cellular senescence, including age-related diseases and disorders in a subject in need thereof. In certain embodiments of the methods described herein, the senescent cell associated disease or disorder is not cancer. Senescent cell associated diseases and disorders include, for example, cardiovascular diseases and disorders, inflammatory diseases and disorders, pulmonary diseases and disorders, neurological diseases and disorders, chemotherapeutic side effects, radiotherapy side effects, and metastasis. A prominent feature of aging is a gradual loss of function, or degeneration that occurs at the molecular, cellular, tissue, and organismal levels. Age-related degeneration gives rise to well-recognized pathologies, such as sarcopenia, atherosclerosis and heart failure, osteoporosis, pulmonary insufficiency, renal failure, neurodegeneration (including macular degeneration, Alzheimer's disease, and Parkinson's disease), and many others. Although different mammalian species vary in their susceptibilities to specific age-related pathologies, collectively, age-related pathologies generally rise with approximately exponential kinetics beginning at about the mid-point of the species-specific life span (e.g., 50-60 years of age for humans) (see, e.g., Campisi, *Annu. Rev. Physiol.* 75:685-705 (2013); Naylor et al., *Clin. Pharmacol. Ther.* 93:105-16 (2013)).

Exemplary conditions, disorders, or diseases that may be treated or prevented by administering a senolytic combination described herein include, without limitation, cognitive diseases (e.g., mild cognitive impairment (MCI), Alzheimer's disease and other dementias); cardiovascular disease (including atherosclerosis); metabolic diseases and disorders (e.g., obesity, diabetes, metabolic syndrome); motor function diseases and disorders (e.g., Parkinson's disease, motor neuron dysfunction (MND)); cerebrovascular disease; emphysema; osteoarthritis; peripheral vascular disease; cardiac diastolic dysfunction; benign prostatic hypertrophy; aortic aneurysm; idiopathic pulmonary fibrosis; chronic obstructive pulmonary disease; osteoarthritis; and macular degeneration. In certain embodiments, any one or more of the diseases or disorders described above or herein may be excluded.

Subjects (i.e., patients, individuals (human or non-human animals)) who may benefit from use of the methods described herein that comprise administering a senolytic combination include those who may also have a cancer. The subject treated by these methods may be considered to be in partial or complete remission (also called cancer remission). As discussed in detail herein, the senolytic combinations for use in methods for selective killing of senescent cells are not intended to be used as a treatment for cancer, that is, in a manner that kills or destroys the cancer cells in a statistically significant manner. Therefore, the methods disclosed herein do not encompass use of the senolytic agents in a manner that would be considered a primary therapy for the treatment of a cancer. Even though a senolytic agent, alone or with other chemotherapeutic or radiotherapy agents, are not used in a manner that is sufficient to be considered as a primary cancer therapy, the methods and senolytic agents described herein may be used in a manner (e.g., a short term course of therapy) that is useful for inhibiting metastases. In other certain embodiments, the subject to be treated with the senolytic agent does not have a cancer (i.e., the subject has not been diagnosed as having a cancer by a person skilled in the medical art).

Cardiovascular Diseases and Disorders

In another embodiment, the senescent cell-associated disease or disorder treated or prevented by the methods described herein comprising administering a senolytic combination is cardiovascular disease. The cardiovascular disease may be any one or more of angina, arrhythmia, atherosclerosis, cardiomyopathy, congestive heart failure, coronary artery disease (CAD), carotid artery disease, endocarditis, heart attack (coronary thrombosis, myocardial infarction [MI]), high blood pressure/hypertension, hypercholesterolemia/hyperlipidemia, mitral valve prolapse, peripheral artery disease (PAD), aortic aneurysm, brain aneurysm, cardiac fibrosis, cardiac diastolic dysfunction, cardiac stress resistance, and stroke.

Atherosclerosis is characterized by patchy intimal plaques (atheromas) that encroach on the lumen of medium-sized and large arteries; the plaques contain lipids, inflammatory cells, smooth muscle cells, and connective tissue. Atherosclerosis can affect large and medium-sized arteries, including the coronary, carotid, and cerebral arteries, the aorta and its branches, and major arteries of the extremities.

Atherosclerosis is characterized by patchy intimal plaques (atheromas) that encroach on the lumen of medium-sized and large arteries; the plaques contain lipids, inflammatory cells, smooth muscle cells, and connective tissue.

Subjects suffering from cardiovascular disease can be identified using standard diagnostic methods known in the art for cardiovascular disease. Generally, diagnosis of atherosclerosis and other cardiovascular disease is based on symptoms (e.g., chest pain or pressure (angina), numbness or weakness in arms or legs, difficulty speaking or slurred speech, drooping muscles in face, leg pain, high blood pressure, kidney failure and/or erectile dysfunction), medical history, and/or physical examination of a patient. Subjects at risk of developing cardiovascular disease include those having a family history of cardiovascular disease and those having other risk factors such as high blood pressure, high cholesterol, diabetes, obesity and/or smoking. In a certain embodiment, the cardiovascular disease that is a senescence cell associated disease/disorder is atherosclerosis. In a certain specific embodiment, a cardiovascular disease or disorder treated or prevented according to the methods and uses described herein does not include stenosis and restenosis.

The effectiveness of a senolytic combination for treating or preventing (i.e., reducing or decreasing the likelihood of developing or occurrence of) a cardiovascular disease (e.g., atherosclerosis) can readily be determined by a person skilled in the medical and clinical arts. One or any combination of diagnostic methods, including physical examination, assessment and monitoring of clinical symptoms, and performance of analytical tests and methods described herein and practiced in the art (e.g., angiography, electrocardiography, stress test, non-stress test), may be used for monitoring the health status of the subject. The effects of the treatment of a senolytic combination can be analyzed using techniques known in the art, such as comparing symptoms of patients suffering from or at risk of cardiovascular disease that have received the treatment with those of patients without such a treatment or with placebo treatment.

Inflammatory Diseases and Disorders

In certain embodiments, a senescent cell-associated disease or disorder is an inflammatory disease or disorder, such as by way of non-limiting example, osteoarthritis, that may be treated or prevented (i.e., likelihood of occurrence is reduced) according to the methods described herein that comprise administration of a senolytic combination. Other inflammatory or autoimmune diseases or disorders that may be treated by administering a senolytic combination described herein include osteoporosis, psoriasis, oral mucositis, rheumatoid arthritis, inflammatory bowel disease, eczema, kyphosis, herniated intervertebral disc, and the pulmonary diseases, COPD and idiopathic pulmonary fibrosis.

Osteoarthritis degenerative joint disease is characterized by fibrillation of the cartilage at sites of high mechanical stress, bone sclerosis, and thickening of the synovium and the joint capsule. Fibrillation is a local surface disorganization involving splitting of the superficial layers of the cartilage. The early splitting is tangential with the cartilage surface, following the axes of the predominant collagen bundles. Collagen within the cartilage becomes disorganized, and proteoglycans are lost from the cartilage surface. In the absence of protective and lubricating effects of proteoglycans in a joint, collagen fibers become susceptible to degradation, and mechanical destruction ensues. Predisposing risk factors for developing osteoarthritis include increasing age, obesity, previous joint injury, overuse of the joint, weak thigh muscles, and genetics. It is a common cause of chronic disability in the elderly. Symptoms of osteoarthritis include sore or stiff joints, particularly the hips, knees, and lower back, after inactivity or overuse; stiffness after resting that goes away after movement; and pain that is worse after activity or toward the end of the day. Osteoarthritis may also affect the neck, small finger joints, the base of the thumb, ankle, and big toe.

Chronic inflammation is thought to be the main age-related factor that contributes to osteoarthritis. In combination with aging, joint overuse and obesity appear to promote osteoarthritis.

The effectiveness a senolytic combination described herein for treatment or prophylaxis of osteoporosis and monitoring of a subject who receives the senolytic combination can readily be determined by a person skilled in the medical and clinical arts. One or any combination of diagnostic methods, including physical examination (such as determining tenderness, swelling or redness of the affected joint), assessment and monitoring of clinical symptoms (such as pain, stiffness, mobility), and performance of analytical tests and methods described herein and practiced in the art (e.g., determining the level of inflammatory cytokines or chemokines; X-ray images to determine loss of cartilage as shown by a narrowing of space between the bones in a joint; magnetic resonance imaging (MRI), providing detailed images of bone and soft tissues, including cartilage), may be used for monitoring the health status of the subject. The effects of the treatment of a senolytic combination can be analyzed by comparing symptoms of patients suffering from or at risk of an inflammatory disease or disorder, such as osteoarthritis, who have received the treatment with those of patients without such a treatment or with placebo treatment.

In certain embodiments, senolytic agents may be used for treating and/or preventing (i.e., decreasing or reducing the likelihood of occurrence) rheumatoid arthritis (RA). Dysregulation of innate and adaptive immune responses characterize rheumatoid arthritis (RA), which is an autoimmune disease the incidence of which increases with age. Certain features of senescence of the immune system and immune cells, such as the decrease in T-cell generation and diversity, may contribute to the development of RA. Older adults may therefore be more susceptible to RA. In young adults, premature immunosenescence may contribute to development of the disease. See, for example, Lindstrom et al., *Journal of the American Geriatrics Society*, 19 Jul. 2010 DOI: 10.1111/j.1532-5415.2010.02965.x). In certain embodiments, RA is excluded.

Chronic inflammation may also contribute to other age-related or aging related diseases and disorders, such as kyphosis and osteoporosis. Kyphosis is a severe curvature in the spinal column, and it is frequently seen with normal and premature aging (see, e.g., Katzman et al. (2010)1 *Orthop. Sports Phys. Ther.* 40: 352-360). Age-related kyphosis often occurs after osteoporosis weakens spinal bones to the point that they crack and compress. A few types of kyphosis target infants or teens. Severe kyphosis can affect lungs, nerves, and other tissues and organs, causing pain and other problems. Kyphosis has been associated with cellular senescence. Characterizing the capability of a senolytic combination for treating kyphosis may be determined in pre-clinical animal models used in the art. By way of example, TTD mice develop kyphosis (see, e.g., de Boer et al. (2002) *Science* 296: 1276-1279); other mice that may be used include BubR1$^{H/H}$ mice, which are also known to develop kyphosis (see, e.g., Baker et al. (2011) *Nature* 479: 232-36). Kyphosis formation is visually measured over time. The level of senescent cells decreased by treatment with the senolytic combination can be determined by detecting the presence of one or more senescent cell associated markers such as by SA-($3$-Gal staining Osteoporosis is a progressive bone disease that is characterized by a decrease in bone mass and density that may lead to an increased risk of fracture. Bone mineral density (BMD) is reduced, bone microarchitecture deteriorates, and the amount and variety of proteins in bone are altered. Osteoporosis is typically diagnosed and monitored by a bone mineral density test. Post-menopausal women or women who have reduced estrogen are most at risk. While both men and women over 75 are at risk, women are twice as likely to develop osteoporosis than men. The level of senescent cells decreased by treatment with the senolytic combination can be determined by detecting the presence of one or more senescent cell associated markers such as by SA-$\beta$-Gal staining.

In still other embodiments, an inflammatory/autoimmune disorder that may be treated with the senolytic combinations described herein includes irritable bowel syndrome (IBS) and inflammatory bowel diseases, such as ulcerative colitis and Crohn's disease. Inflammatory bowel disease (IBD) involves chronic inflammation of all or part of the digestive tract. In addition to life-threatening complications arising from IBD, the disease can be painful and debilitating. Ulcerative colitis is an inflammatory bowel disease that causes long-lasting inflammation in part of the digestive tract. Symptoms usually develop over time, rather than suddenly. Ulcerative colitis usually affects only the innermost lining of the large intestine (colon) and rectum. Crohn's disease is an inflammatory bowel disease that causes inflammation anywhere along the lining of your digestive tract, and often extends deep into affected tissues. This can lead to abdominal pain, severe diarrhea, and malnutrition. The inflammation caused by Crohn's disease can involve different areas of the digestive tract. Diagnosis and monitoring of the diseases is performed according to methods and diagnostic tests routinely practiced in the art, including blood tests, colonoscopy, flexible sigmoidoscopy, barium enema, CT scan, MM, endoscopy, and small intestine imaging.

In other embodiments, the methods described herein may be useful for treating a subject who has herniated intervertebral discs. Subjects with these herniated discs exhibit elevated presence of cell senescence in the blood and in vessel walls (see e.g., Roberts et al. (2006) *Eur. Spine J.* 15 Suppl 3: S312-316). Symptoms of a herniated intervertebral disc may include pain, numbness or tingling, or weakness in an arm or leg. Increased levels of proinflammatory molecules and matrix metalloproteases are also found in aging and degenerating discs tissues, suggesting a role for senescence cells (see e.g., Chang-Qing et al. (2007) *Ageing Res. Rev.* 6: 247-61). Animal models may be used to characterize the effectiveness of a senolytic combination in treating herniated intervertebral discs; degeneration of the intervertebral disc is induced in mice by compression and disc strength evaluated (see e.g., Lotz et al. (1998) *Spine* (Philadelphia Pa. 1976). 23:2493-506).

Other inflammatory or autoimmune diseases that may be treated or prevented (i.e., likelihood of occurrence is reduced) by using a senolytic combination include eczema, psoriasis, osteoporosis, and pulmonary diseases (e.g., chronic obstructive pulmonary disease (COPD), idiopathic pulmonary fibrosis (IPF), asthma), inflammatory bowel disease, and mucositis (including oral mucositis, which in some instances is induced by radiation). Certain fibrosis or fibrotic conditions of organs such as renal fibrosis, liver fibrosis, pancreatic fibrosis, cardiac fibrosis, skin wound healing, and oral submucous fibrosis may be treated with using the senolytic combination.

In certain embodiments, the senescent cell associated disorder is an inflammatory disorder of the skin, such as by way of a non-limiting examples, psoriasis and eczema that may be treated or prevented according to the methods described herein that comprise administration of a senolytic combination. Psoriasis is characterized by abnormally excessive and rapid growth of the epidermal layer of the skin. A diagnosis of psoriasis is usually based on the appearance of the skin. Skin characteristics typical for psoriasis are scaly red plaques, papules, or patches of skin that may be painful and itch. In psoriasis, cutaneous and systemic overexpression of various proinflammatory cytokines is observed such as IL-6, a key component of the SASP. Eczema is an inflammation of the skin that is characterized by redness, skin swelling, itching and dryness, crusting, flaking, blistering, cracking, oozing, or bleeding. The effectiveness of senolytic combinations for treatment of psoriasis and eczema and monitoring of a subject who receives such a senolytic combination can be readily determined by a person skilled in the medical or clinical arts. One or any combination of diagnostic methods, including physical examination (such as skin appearance), assessment of monitoring of clinical symptoms (such as itching, swelling, and pain), and performance of analytical tests and methods described herein and practiced in the art (i.e., determining the level of pro-inflammatory cytokines).

Other immune disorders or conditions that may be treated with a senolytic combination include conditions resulting from a host immune response to an organ transplant (e.g., kidney, bone marrow, liver, lung, or heart transplant), such as rejection of the transplanted organ. The senolytic combination may be used for treating or reducing the likelihood of occurrence of graft-vs-host disease.

Pulmonary Diseases and Disorders

In one embodiment, methods are provided for treating or preventing (i.e., reducing the likelihood of occurrence) a senescence-associated disease or disorder that is a pulmonary disease or disorder by killing senescent cells (i.e., established senescent cells) associated with the disease or disorder in a subject who has the disease or disorder by administering a senolytic combination. Senescence associated pulmonary diseases and disorders include, for example, idiopathic pulmonary fibrosis (IPF), chronic obstructive pulmonary disease (COPD), asthma, cystic fibrosis, bronchiectasis, and emphysema.

COPD is a lung disease defined by persistently poor airflow resulting from the breakdown of lung tissue (emphysema) and the dysfunction of the small airways (obstructive bronchiolitis). Primary symptoms of COPD include shortness of breath, wheezing, chest tightness, chronic cough, and excess sputum production. Elastase from cigarette smoke-activated neutrophils and macrophages disintegrates the extracellular matrix of alveolar structures, resulting in enlarged air spaces and loss of respiratory capacity (see, e.g., Shapiro et al., *Am. J. Respir. Cell MOL Biol.* 32, 367-372 (2005)). COPD is most commonly caused by tobacco smoke (including cigarette smoke, cigar smoke, secondhand smoke, pipe smoke), occupational exposure (e.g., exposure to dust, smoke or fumes), and pollution, occurring over decades thereby implicating aging as a risk factor for developing COPD.

The processes involved in causing lung damage include, for example, oxidative stress produced by the high concentrations of free radicals in tobacco smoke; cytokine release due to inflammatory response to irritants in the airway; and impairment of anti-protease enzymes by tobacco smoke and free radicals, allowing proteases to damage the lungs. Genetic susceptibility likely contributes to the disease because only about 20% of smokers develop COPD. In about 1% percent of people with COPD, the disease results from a genetic disorder that causes low level production of alpha-1-antitrypsin in the liver. The enzyme is normally secreted into the bloodstream to help protect the lungs.

Pulmonary fibrosis is a chronic and progressive lung disease characterized by stiffening and scarring of the lung, which may lead to respiratory failure, lung cancer, and heart failure. Fibrosis is associated with repair of epithelium. Fibroblasts are activated, production of extracellular matrix proteins is increased, and transdifferentiation to contractile myofibroblasts contribute to wound contraction. A provisional matrix plugs the injured epithelium and provides a scaffold for epithelial cell migration, involving an epithelial-mesenchymal transition (EMT). Blood loss associated with epithelial injury induces platelet activation, production of growth factors, and an acute inflammatory response. Normally, the epithelial barrier heals and the inflammatory response resolves. However, in fibrotic disease the fibroblast response continues, resulting in unresolved wound healing. Formation of fibroblastic foci is a feature of the disease, reflecting locations of ongoing fibrogenesis. As the name connotes, the etiology of IPF is unknown. The involvement of cellular senescence in IPF is suggested by the observations that the incidence of the disease increases with age and that lung tissue in IPF patients is enriched for SA-β-Gal-positive cells and contains elevated levels of the senescence marker p21 (see, e.g., Minagawa et al., *Am. J. Physiol. Lung Cell. Mol. Physiol.* 300:L391-L401 (2011); see also, e.g., Naylor et al., supra). Short telomeres are a risk factor common to both IPF and cellular senescence (see, e.g., Alder et al., *Proc. Natl. Acad. Sci. USA* 105:13051-56 (2008)). Without wishing to be bound by theory, the contribution of cellular senescence to IPF is suggested by the report that SASP components of senescent cells, such as IL-6, IL-8, and IL-1β, promote fibroblast-to-myofibroblast differentiation and epithelial—mesenchymal transition, resulting in extensive remodeling of the extracellular matrix of the alveolar and interstitial spaces (see, e.g., Minagawa et al., supra).

Subjects at risk of developing pulmonary fibrosis include those exposed to environmental or occupational pollutants, such as asbestosis and silicosis; who smoke cigarettes; having some typical connective tissue diseases such as rheumatoid arthritis, SLE and scleroderma; having other diseases that involve connective tissue, such as sarcoidosis and Wegener's granulomatosis; having infections; taking certain medications (e.g., amiodarone, bleomycin, busufan, methotrexate, and nitrofurantoin); those subject to radiation therapy to the chest; and those whose family member has pulmonary fibrosis.

Symptoms of COPD may include any one of shortness of breath, especially during physical activities; wheezing; chest tightness; having to clear your throat first thing in the morning because of excess mucus in the lungs; a chronic cough that produces sputum that may be clear, white, yellow or greenish; blueness of the lips or fingernail beds (cyanosis); frequent respiratory infections; lack of energy; unintended weight loss (observed in later stages of disease). Subjects with COPD may also experience exacerbations, during which symptoms worsen and persist for days or longer. Symptoms of pulmonary fibrosis are known in the art and include shortness of breath, particularly during exercise; dry, hacking cough; fast, shallow breathing; gradual unintended weight loss; tiredness; aching joints and muscles; and clubbing (widening and rounding of the tips of the fingers or toes).

Subjects suffering from COPD or pulmonary fibrosis can be identified using standard diagnostic methods routinely practiced in the art. Monitoring the effect of a senolytic combination administered to a subject who has or who is at risk of developing a pulmonary disease may be performed using the methods typically used for diagnosis. Generally, one or more of the following exams or tests may be performed: physical exam, patient's medical history, patient's family's medical history, chest X-ray, lung function tests (such as spirometry), blood test (e.g., arterial blood gas analysis), bronchoalveolar lavage, lung biopsy, CT scan, and exercise testing.

Other pulmonary diseases or disorders that may be treated by using a senolytic combination include, for example, emphysema, asthma, bronchiectasis, and cystic fibrosis (see, e.g., Fischer et al., *Am J Physiol Lung Cell Mol Physiol.* 304(6):L394-400 (2013)). These diseases may also be exacerbated by tobacco smoke (including cigarette smoke, cigar smoke, secondhand smoke, pipe smoke), occupational exposure (e.g., exposure to dust, smoke or fumes), infection, and/or pollutants that induce cells into senescence and thereby contribute to inflammation. Emphysema is sometimes considered as a subgroup of COPD.

Bronchiectasis is results from damage to the airways that causes them to widen and become flabby and scarred. Bronchiectasis usually is caused by a medical condition that injures the airway walls or inhibits the airways from clearing mucus. Examples of such conditions include cystic fibrosis and primary ciliary dyskinesia (PCD). When only one part of the lung is affected, the disorder may be caused by a blockage rather than a medical condition.

The methods described herein for treating a senescence associate pulmonary disease or disorder may also be used for treating a subject who is aging and has loss (or degeneration) of pulmonary function (i.e., declining or impaired pulmonary function compared with a younger subject) and/ or degeneration of pulmonary tissue. The respiratory system undergoes various anatomical, physiological and immunological changes with age. The structural changes include chest wall and thoracic spine deformities that can impair the total respiratory system compliance resulting in increased effort to breathe. The respiratory system undergoes structural, physiological, and immunological changes with age. An increased proportion of neutrophils and lower percentage of macrophages can be found in bronchoalveolar lavage (BAL) of older adults compared with younger adults. Persistent low grade inflammation in the lower respiratory tract can cause proteolytic and oxidant-mediated injury to the lung matrix resulting in loss of alveolar unit and impaired gas exchange across the alveolar membrane seen with aging. Sustained inflammation of the lower respiratory tract may predispose older adults to increased susceptibility to toxic environmental exposure and accelerated lung function decline. (See, for example, Sharma et al., *Clinical Interventions in Aging* 1:253-60 (2006)). Oxidative stress exacerbates inflammation during aging (see, e.g., Brod, *Inflamm Res* 2000; 49:561-570; Hendel et al., *Cell Death and Differentiation* (2010) 17:596-606). Alterations in redox balance and increased oxidative stress during aging precipitate the expression of cytokines, chemokines, and adhesion molecules, and enzymes (see, e.g., Chung et al., *Ageing Res Rev* 2009; 8:18-30). Constitutive activation and recruitment of macrophages, T cells, and mast cells foster release of proteases leading to extracellular matrix degradation, cell death, remodeling, and other events that can cause tissue and organ damage during chronic inflammation (see, e.g., Demedts et al., *Respir Res* 2006; 7: 53-63). By administering a senolytic combination to an aging subject (which includes a middle-aged adult who is asymptomatic), the decline in pulmonary function may be decelerated or inhibited by killing and removing senescent cells from the respiratory tract.

The effectiveness of a senolytic combination can readily be determined by a person skilled in the medical and clinical arts. One or any combination of diagnostic methods, including physical examination, assessment and monitoring of clinical symptoms, and performance of analytical tests and methods described herein, may be used for monitoring the health status of the subject. The effects of the treatment of a therapeutic agent or pharmaceutical composition can be analyzed using techniques known in the art, such as comparing symptoms of patients suffering from or at risk of pulmonary fibrosis that have received the treatment with those of patients without such a treatment or with placebo treatment. In addition, methods and techniques that evaluate mechanical functioning of the lung, for example, techniques that measure lung capacitance, elastance, and airway hypersensitivity may be performed. To determine lung function and to monitor lung function throughout treatment, any one of numerous measurements may be obtained, expiratory reserve volume (ERV), forced vital capacity (FVC), forced expiratory volume (FEV) (e.g., FEV in one second, FEV1), FEV1/FEV ratio, forced expiratory flow 25% to 75%, and maximum voluntary ventilation (MVV), peak expiratory flow (PEF), slow vital capacity (SVC). Total lung volumes include total lung capacity (TLC), vital capacity (VC), residual volume (RV), and functional residual capacity (FRC). Gas exchange across alveolar capillary membrane can be measured using diffusion capacity for carbon monoxide (DLCO). Peripheral capillary oxygen saturation (SpO2) can also be measured; normal oxygen levels are typically between 95% and 100%. An SpO2 level below 90% suggests the subject has hypoxemia. Values below 80% are considered critical and requiring intervention to maintain brain and cardiac function and avoid cardiac or respiratory arrest.

Neurological Diseases and Disorders

Senescent cell-associated diseases or disorders treatable by administering a senolytic combination described herein include neurological diseases or disorders. Such senescent cell associated diseases and disorders include Parkinson's disease, Alzheimer's disease (and other dementias), motor neuron dysfunction (MND), mild cognitive impairment (MCI), Huntington's disease, and diseases and disorders of the eyes, such as the neurodegenerative disease/disorder, macular degeneration. Other diseases of the eye that are associated with increasing age are glaucoma, vision loss, and cataracts.

Parkinson's disease is the second most common neurodegenerative disease. It is a disabling condition of the brain characterized by slowness of movement (bradykinesia), shaking, stiffness, and in the later stages, loss of balance. Many of these symptoms are due to the loss of certain nerves in the brain, which results in the lack of dopamine. This disease is characterized by neurodegeneration, such as the loss of about 50% to 70% of the dopaminergic neurons in the substantia nigra pars compacta, a profound loss of dopamine in the striatum, and/or the presence of intracytoplasmic inclusions (Lewy bodies), which are composed mainly of alpha-synuclein and ubiquitin. Parkinson's disease also features locomotor deficits, such as tremor, rigidity, bradykinesia, and/or postural instability. These motor manifestations can also be accompanied by nonmotor symptoms such as olfactory deficits, sleep impairment, and neuropsychiatric disorders. Generally, diagnosis of Parkinson's disease is based on symptoms, medical history, and neurological and/ or physical examination of a patient. Subjects at risk of developing Parkinson's disease include those having a family history of Parkinson's disease and those exposed to pesticides (e.g., rotenone or paraquat), herbicides (e.g., agent orange), or heavy metals. Senescence of dopamine-producing neurons is thought to contribute to the observed cell death in PD through the production of reactive oxygen species (see, e.g., Cohen et al., J. *Neural Transm. Suppl.* 19:89-103 (1983)); therefore, the methods and senolytic combinations described herein are useful for treatment and prophylaxis of Parkinson's disease.

Methods for detecting, monitoring or quantifying neurodegenerative deficiencies and/or locomotor deficits associated with Parkinson's diseases are known in the art, such as histological studies, biochemical studies, and behavioral assessment (see, e.g., U.S. Application Publication No. 2012/0005765). Symptoms of Parkinson's disease are known in the art and include, but are not limited to, difficulty starting or finishing voluntary movements, jerky, stiff movements, muscle atrophy, shaking (tremors), and changes in heart rate, but normal reflexes, bradykinesia, and postural instability. There is a growing recognition that people diagnosed with Parkinson's disease may have cognitive impairment, including mild cognitive impairment, in addition to their physical symptoms.

Alzheimer's disease (AD) is a neurodegenerative disease that shows a slowly progressive mental deterioration with failure of memory, disorientation, and confusion, leading to profound dementia. Age is the single greatest predisposing risk factor for developing AD, which is the leading cause of dementia in the elderly (see, e.g., Hebert, et al., *Arch. Neural.* 60:1119-1122 (2003)). Early clinical symptoms show remarkable similarity to mild cognitive impairment (see below), which is characterized by difficulty in remembering recent life experiences or people's names. As the disease progresses, impaired judgment, confusion, behavioral changes, disorientation, and difficulty in walking and swallowing occur.

Alzheimer's disease is characterized by the presence of neurofibrillary tangles and amyloid (senile) plaques in histological specimens. The disease predominantly involves the limbic and cortical regions of the brain. The argyrophilic plaques containing the amyloidogenic fragment of amyloid precursor protein (APP) are scattered throughout the cerebral cortex and hippocampus. Neuro fibrillary tangles are found in pyramidal neurons predominantly located in the neocortex, hippocampus, and nucleus basalis of Meynert. Other changes, such as granulovacuolar degeneration in the pyramidal cells of the hippocampus, and neuron loss and gliosis in the cortex and hippocampus, are observed. The vast majority of Alzheimer's disease cases are sporadic; however, a small percentage of patients have an autosomal dominant form of the disease called early onset familial Alzheimer's disease that may be a predisposing factor for developing the disease. Most autosomal dominant familial AD can be attributed to mutations in APP, presenilin 1, or presenilin 2. Subjects at risk of developing Alzheimer's disease include those of advanced age, those with a family history of Alzheimer's disease, those with genetic risk genes (e.g., ApoE4) or deterministic gene mutations (e.g., APP, PS1, or PS2), and those with history of head trauma or heart/vascular conditions (e.g., high blood pressure, heart disease, stroke, diabetes, high cholesterol).

A number of behavioral and histopathological assays are known in the art for evaluating Alzheimer's disease phenotype, for characterizing therapeutic agents, and assessing treatment. Histological analyses are typically performed postmortem. Histological analysis of Aβ levels may be performed using Thioflavin-S. Congo red, or anti-A(3 staining (e.g., 4G8, 10D5, or 6E10 antibodies) to visualize Aβ deposition on sectioned brain tissues (see, e.g., Holcomb et al., 1998, *Nat. Med.* 4:97-100; Borchelt et al., 1997, *Neuron* 19:939-945; Dickson et al., 1988, *Am. J. Path.* 132:86-101). In vivo methods of visualizing Aβ deposition in transgenic mice have been also described. BSB ((trans, trans)-1-bromo-2,5-bis-(3-hydroxycarbonyl-4-hydroxy)styrylbenzene) and PET tracer $^{11}$C-labelled Pittsburgh Compound-B (PIB) bind to AP plaques (see, e.g., Skovronsky et al., 2000, *Proc. Natl. Acad. Sci. USA* 97:7609-7614; Klunk et al., 2004, Ann. Neurol. 55:306-319). $^{19}$F-containing amyloidophilic Congo red-type compound FSB ((E,E)-1-fluoro-2,5-bis-(3-hydroxycarbonyl-4-hydroxy)styrylbenzene) allows visualization of Aβ plaques by MRI (see, e.g., Higuchi et al., 2005, *Nature Neurosci.* 8:527-533). Radiolabeled, putrescine-modified amyloid-beta peptide labels amyloid deposits in vivo in a mouse model of Alzheimer's disease (see, e.g., Wengenack et al., 2000, *Nat. Biotechnol.* 18:868-872).

Increased glial fibrillary acidic protein (GFAP) by astrocytes is a marker for astroglial activation and gliosis during neurodegeneration. Aβ plaques are associated with GFAP-positive activated astrocytes, and may be visualized via GFAP staining (see, e.g., Nagele et al. 2004, *Neurobiol. Aging* 25:663-674; Mandybur et al., 1990, *Neurology* 40:635-639; Liang et al., 2010, *J. Biol. Chem.* 285:27737-27744). Neurofibrillary tangles may be identified by immunohistochemistry using thioflavin-S fluorescent microscopy and Gallyas silver stains (see, e.g., Gotz et al., 2001, *J. Biol. Chem.* 276:529-534; U.S. Pat. No. 6,664,443). Axon staining with electron microscopy and axonal transport studies may be used to neuronal degeneration (see, e.g., Ishihara et al., 1999, *Neuron* 24:751-762).

Subjects suffering from Alzheimer's disease can be identified using standard diagnostic methods known in the art for Alzheimer's disease. Generally, diagnosis of Alzheimer's disease is based on symptoms (e.g., progressive decline in memory function, gradual retreat from and frustration with normal activities, apathy, agitation or irritability, aggression, anxiety, sleep disturbance, dysphoria, aberrant motor behavior, disinhibition, social withdrawal, decreased appetite, hallucinations, dementia), medical history, neuropsychological tests, neurological and/or physical examination of a patient. Cerebrospinal fluid may also be for tested for various proteins that have been associated with Alzheimer pathology, including tau, amyloid beta peptide, and AD7C-NTP. Genetic testing is also available for early-onset familial Alzheimer disease (eFAD), an autosomal-dominant genetic disease. Clinical genetic testing is available for individuals with AD symptoms or at-risk family members of patients with early-onset disease. In the U.S., mutations for PS2, and APP may be tested in a clinical or federally approved laboratory under the Clinical Laboratory Improvement Amendments. A commercial test for PS1 mutations is also available (Elan Pharmaceuticals).

The effectiveness of a senolytic combination described herein and monitoring of a subject who receives the senolytic combination can readily be determined by a person skilled in the medical and clinical arts. One or any combination of diagnostic methods, including physical examination, assessment and monitoring of clinical symptoms, and performance of analytical tests and methods described herein, may be used for monitoring the health status of the subject. The effects of administering a senolytic combination can be analyzed using techniques known in the art, such as comparing symptoms of patients suffering from or at risk of Alzheimer's disease that have received the treatment with those of patients without such a treatment or with placebo treatment.

Mild Cognitive Impairment (MCI). MCI is a brain-function syndrome involving the onset and evolution of cognitive impairments beyond those expected based on age and education of the individual, but which are not significant enough to interfere with this individual's daily activities. MCI is an aspect of cognitive aging that is considered to be a transitional state between normal aging and the dementia into which it may convert (see, Pepeu, *Dialogues in Clinical Neuroscience* 6:369-377, 2004). It is characterized by subtle memory impairment, mild neuropathological changes (e.g., astogliosis, few deposit of beta-amyloid, diffuse amyloid in the neocortex, neurofibrillary tangles in the medial temporal lobe), and changes in the cholinergic system (e.g., loss of cholinergic neurons, decrease in acetyl choline release).

MCI that primarily affects memory is known as "amnestic MCI." A person with amnestic MCI may start to forget important information that he or she would previously have recalled easily, such as recent events. Amnestic MCI is frequently seen as prodromal stage of Alzheimer's disease. MCI that affects thinking skills other than memory is known as "nonamnestic MCI." This type of MCI affect thinking skills such as the ability to make sound decisions, judge the time or sequence of steps needed to complete a complex task, or visual perception. Individuals with nonamnestic MCI are believed to be more likely to convert to other types of dementias (e.g., dementia with Lewy bodies).

Persons in the medical art have a growing recognition that people diagnosed with Parkinson's disease may have MCI in addition to their physical symptoms. Recent studies show 20-30% of people with Parkinson's disease have MCI, and that their MCI tends to be non-amnestic. Parkinson's disease patients with MCI sometimes go on to develop full blown dementia (Parkinson's disease with dementia).

Methods for detecting, monitoring, quantifying or assessing neuropathological deficiencies associated with MCI are known in the art, including astrocyte morphological analyses, release of acetylcholine, silver staining for assessing neurodegeneration, and PiB PET imaging to detect beta amyloid deposits (see, e.g., U.S. Application Publication No. 2012/0071468; Pepeu, 2004, supra). Methods for detecting, monitoring, quantifying or assessing behavioral deficiencies associated with MCI are also known in the art, including eight-arm radial maze paradigm, non-matching-to-sample task, allocentric place determination task in a water maze, Morris maze test, visuospatial tasks, and delayed response spatial memory task, olfactory novelty test (see, id.).

Motor Neuron Dyslimction (MND). MND is a group of progressive neurological disorders that destroy motor neurons, the cells that control essential voluntary muscle activity such as speaking, walking, breathing and swallowing. It is classified according to whether degeneration affects upper motor neurons, lower motor neurons, or both. Examples of MNDs include, but are not limited to Amyotrophic Lateral Sclerosis (ALS), also known as Lou Gehrig's Disease, progressive bulbar palsy, pseudobulbar palsy, primary lateral sclerosis, progressive muscular atrophy, lower motor neuron disease, and spinal muscular atrophy (SMA) (e.g., SMA1 also called Werdnig-Hoffmann Disease, SMA2, SMA3 also called Kugelberg-Welander Disease, and Kennedy's disease), post-polio syndrome, and hereditary spastic paraplegia. In adults, the most common MND is amyotrophic lateral sclerosis (ALS), which affects both upper and lower motor neurons. It can affect the arms, legs, or facial muscles. Primary lateral sclerosis is a disease of the upper motor neurons, while progressive muscular atrophy affects only lower motor neurons in the spinal cord. In progressive bulbar palsy, the lowest motor neurons of the brain stem are most affected, causing slurred speech and difficulty chewing and swallowing. There are almost always mildly abnormal signs in the arms and legs. Patients with MND exhibit a phenotype of Parkinson's disease (e.g., having tremor, rigidity, bradykinesia, and/or postural instability). Methods for detecting, monitoring or quantifying locomotor and/or other deficits associated with Parkinson's diseases, such as MND, are known in the art (see, e.g., U.S. Application Publication No. 20120005765).

Methods for detecting, monitoring, quantifying or assessing motor deficits and histopathological deficiencies associated with MND are known in the art, including histopathological, biochemical, and electrophysiological studies and motor activity analysis (see, e.g., Rich et al., *J Neurophysiol* 88:3293-3304, 2002; Appel et al., *Proc. Natl. Acad. Sci. USA* 88:647-51, 1991). Histopathologically, MNDs are characterized by death of motor neurons, progressive accumulation of detergent-resistant aggregates containing SOD1 and ubiquitin and aberrant neurofilament accumulations in degenerating motor neurons. In addition, reactive astroglia and microglia are often detected in diseased tissue. Patients with an MND show one or more motor deficits, including muscle weakness and wasting, uncontrollable twitching, spasticity, slow and effortful movements, and overactive tendon reflexes.

Macular degeneration is a neurodegenerative disease that causes the loss of photoreceptor cells in the central part of retina, called the macula. Macular degeneration generally is classified into two types: dry type and wet type. The dry form is more common than the wet, with about 90% of age-related macular degeneration (ARMD) patients diagnosed with the dry form. The wet form of the disease usually leads to more serious vision loss. While the exact causes of age-related macular degeneration are still unknown, the number of senescent retinal pigmented epithelial (RPE) cells increases with age. Age and certain genetic factors and environmental factors (see, e.g., Lyengar et al., *Am. J. Hum. Genet.* 74:20-39 (2004) (Epub 2003 Dec. 19); Kenealy et al., *Mol. Vis.* 10:57-61 (2004); Gorin et al., *Mol. Vis.* 5:29 (1999)) are risk factors for developing ARMD. Environment predisposing factors include omega-3 fatty acids intake (see, e.g., Christen et al., *Arch Ophthalmol.* 129:921-29 (2011)); estrogen exposure (see, e.g., Feshanich et al., *Arch Ophthalmol* 126(4):519-24) (2008)); and increased scrum levels of vitamin D (see, e.g., Millen, et al., *Arch Ophthalmol.* 129 (4):481-89 (2011)). Genetic predisposing risk factors include reduced levels Dicer1 (enzyme involved in maturation of micro RNA) in eyes of patients with dry AMD, and decreased micro RNAs contributes to a senescent cell profile; and DICER1 ablation induces premature senescence (see, e.g., Mudhasani *J. Cell. Biol.* (2008)).

Dry ARMD is associated with atrophy of RPE layer causes loss of photoreceptor cells. The dry form of ARMD may result from the aging and thinning of macular tissues, and deposition of pigment in the macula. Senescence appears to inhibit both replication and migration of RPE, resulting in permanent RPE depletion in the macula of dry AMD patients (see, e.g., Iriyama et al., *J. Biol. Chem.* 283:11947-953 (2008)). With wet ARMD, new blood vessels grow beneath the retina and leak blood and fluid. This abnormal leaky choroidal neovascularization causes the retinal cells to die, creating blind spots in central vision. Different forms of macular degeneration may also occur in younger patients. Non-age related etiology may be linked to heredity, diabetes, nutritional deficits, head injury, infection, or other factors.

Declining vision noticed by the patient or by an ophthalmologist during a routine eye exam may be the first indicator of macular degeneration. The formation of exudates, or "drusen," underneath the Bruch's membrane of the macula is often the first physical sign that macular degeneration may develop. Symptoms include perceived distortion of straight lines and, in some cases, the center of vision appears more distorted than the rest of a scene; a dark, blurry area or "white-out" appears in the center of vision; and/or color perception changes or diminishes. Diagnosing and monitoring of a subject with macular degeneration may be accomplished by a person skilled in the ophthalmic art according to art-accepted periodic eye examination procedures and report of symptoms by the subject.

Glaucoma. In certain embodiments, the senescence associated disease or disorder is glaucoma. Glaucoma is a broad term used to describe a group of diseases that causes visual field loss, often without any other prevailing symptoms. The lack of symptoms often leads to a delayed diagnosis of glaucoma until the terminal stages of the disease. Even if subjects afflicted with glaucoma do not become blind, their vision is often severely impaired. Normally, clear fluid flows into and out of the front part of the eye, known as the anterior chamber. In individuals who have open/wide-angle glaucoma, this fluid drains too slowly, leading to increased pressure within the eye. If left untreated, this high pressure subsequently damages the optic nerve and can lead to complete blindness. The loss of peripheral vision is caused by the death of ganglion cells in the retina. Ganglion cells are a specific type of projection neuron that connects the eye to the brain. When the cellular network required for the outflow of fluid was subjected to SA-β-Gal staining, a fourfold increase in senescence has been observed in glaucoma patients (see, e.g., Liton et al., *Exp. Gerontol.* 40:745-748 (2005)).

For monitoring the effect of a therapy on inhibiting progression of glaucoma, standard automated perimetry (visual field test) is the most widely used technique. In addition, several algorithms for progression detection have been developed (see, e.g., Wesselink et al., *Arch Ophthalmol.* 127(3):270-274 (2009), and references therein). Additional methods include gonioscopy (examines the trabecular meshwork and the angle where fluid drains out of the eye); imaging technology, for example scanning laser tomography (e.g., HRT3), laser polarimetry (e.g., GDX), and ocular coherence tomography); ophthalmoscopy; and pachymeter measurements that determine central corneal thickness.

Cataracts. Cataracts are a clouding of the lens of an eye, causing blurred vision, and if left untreated can result in blindness. Surgery is effective and routinely performed to remove cataracts. Administration of a senolytic combination described herein may result in decreasing the likelihood of occurrence of a cataract or may slow or inhibit progression of a cataract. The presence and severity of a cataract can be monitored by eye exams using methods routinely performed by a person skilled in the ophthalmology art.

Metabolic Disease or Disorder

Senescent cell-associated diseases or disorders treatable by administering a senolytic combination described herein include metabolic diseases or disorders. Such senescent cell associated diseases and disorders include diabetes, metabolic syndrome, diabetic ulcers, and obesity.

Diabetes is characterized by high levels of blood glucose caused by defects in insulin production, insulin action, or both. The great majority (90 to 95%) of all diagnosed cases of diabetes in adults are type 2 diabetes, characterized by the gradual loss of insulin production by the pancreas. Diabetes is the leading cause of kidney failure, nontraumatic lower-limb amputations, and new cases of blindness among adults in the U.S. Diabetes is a major cause of heart disease and stroke and is the seventh leading cause of death in the U.S. (see, e.g., Centers for Disease Control and Prevention, National diabetes fact sheet: national estimates and general information on diabetes and prediabetes in the United States, 2011 ("Diabetes fact sheet")). A senolytic combination described herein may be used for treating and/or preventing type 2 diabetes, particularly age-, diet- and obesity-associated type 2 diabetes.

Involvement of senescent cells in metabolic disease, such as obesity and type 2 diabetes, has been suggested as a response to injury or metabolic dysfunction (see, e.g., Tchkonia et al., *Aging Cell* 9:667-684 (2010)). Fat tissue from obese mice showed induction of the senescence markers SA-13-Gal, p53, and p21 (see, e.g., Tchkonia et al., supra; Minamino et al., *Nat. Med.* 15:1082-1087 (2009)). A concomitant upregulation of proinflammatory cytokines, such as tumor necrosis factor-a and Cc12/MCP1, was observed in the same fat tissue (see, e.g., Minamino et al., supra). Induction of senescent cells in obesity potentially has clinical implications because proinflammatory SASP components are also suggested to contribute to type 2 diabetes (see, e.g., Tchkonia et al., supra). A similar pattern of upregulation of senescence markers and SASP components are associated with diabetes, both in mice and in humans (see, e.g., Minamino et al., supra). Accordingly, the methods described herein that comprise administering a senolytic combination may be useful for treatment or prophylaxis of type 2 diabetes, as well as obesity and metabolic syndrome. Without wishing to be bound by theory, contact of senescent preadipocytes with a senolytic combination described herein thereby killing the senescent preadipocytes may provide clinical and health benefit to a person who has any one of diabetes, obesity, or metabolic syndrome.

Subjects suffering from type 2 diabetes can be identified using standard diagnostic methods known in the art for type 2 diabetes. Generally, diagnosis of type 2 diabetes is based on symptoms (e.g., increased thirst and frequent urination, increased hunger, weight loss, fatigue, blurred vision, slow-healing sores or frequent infections, and/or areas of darkened skin), medical history, and/or physical examination of a patient. Subjects at risk of developing type 2 diabetes include those who have a family history of type 2 diabetes and those who have other risk factors such as excess weight, fat distribution, inactivity, race, age, prediabetes, and/or gestational diabetes.

The effectiveness of a senolytic combination can readily be determined by a person skilled in the medical and clinical arts. One or any combination of diagnostic methods, including physical examination, assessment and monitoring of clinical symptoms, and performance of analytical tests and methods, such as those described herein, may be used for monitoring the health status of the subject. A subject who is receiving a senolytic combination described herein for treatment or prophylaxis of diabetes can be monitored, for example, by assaying glucose and insulin tolerance, energy expenditure, body composition, fat tissue, skeletal muscle, and liver inflammation, and/or lipotoxicity (muscle and liver lipid by imaging in vivo and muscle, liver, bone marrow, and pancreatic 13-cell lipid accumulation and inflammation by histology). Other characteristic features or phenotypes of type 2 diabetes are known and can be assayed as described herein and by using other methods and techniques known and routinely practiced in the art.

Subjects who have type 2 diabetes or who are at risk of developing type 2 diabetes may have metabolic syndrome. Metabolic syndrome in humans is typically associated with obesity and characterized by one or more of cardiovascular disease, liver steatosis, hyperlipidemia, diabetes, and insulin resistance. A patient with metabolic syndrome may present with a cluster of metabolic disorders or abnormalities which may include, for example, one or more of hypertension, type-2 diabetes, hyperlipidemia, dyslipidemia (e.g., hypertriglyceridemia, hypercholesterolemia), insulin resistance, liver steatosis (steatohepatitis), hypertension, atherosclerosis, and other metabolic disorders.

Obesity and obesity-related are used to refer to conditions of subjects who have a body mass that is measurably greater than ideal for their height and frame. Body Mass Index (BMI) is a measurement tool used to determine excess body weight, and is calculated from the height and weight of a subject. A human is considered overweight when the person has a BMI of 25-29; a person is considered obese when the person has a BMI of 30-39, and a person is considered severely obese when the person has a BMI of >40. Accordingly, the terms obesity and obesity-related refer to human subjects with body mass index values of greater than 30, greater than 35, or greater than 40. A category of obesity not captured by BMI is called "abdominal obesity" in the art, which relates to the extra fat found around a subject's middle, which is an important factor in health, even independent of BMI. The simplest and most often used measure of abdominal obesity is waist size. Generally abdominal obesity in women is defined as a waist size 35 inches or higher, and in men as a waist size of 40 inches or higher. More complex methods for determining obesity require specialized equipment, such as magnetic resonance imaging or dual energy X-ray absorptiometry machines.

A condition or disorder associated with diabetes and senescence is a diabetic ulcer (i.e., diabetic wound). An ulcer is a breakdown in the skin, which may extend to involve the subcutaneous tissue or even muscle or bone. These lesions occur, particularly, on the lower extremities. Patients with diabetic venous ulcer exhibit elevated presence of cellular senescence at sites of chronic wounds (see, e.g., Stanley et al. (2001) *J. Vas. Surg.* 33: 1206-1211). Chronic inflammation is also observed at sites of chronic wounds, such as diabetic ulcers (see, e.g., Goren et al. (2006) *Am. J. Pathol.* 7 168: 65-77; Seitz et al. (2010) *Exp. Diabetes Res.* 2010: 476969), suggesting that the proinflammatory cytokine phenotype of senescent cells has a role in the pathology.

Renal Dysfunction: Nephrological pathologies, such as glomerular disease, arise in the elderly. Glomerulonephritis is characterized by inflammation of the kidney and by the expression of two proteins, IL1α and IL1β (see, e.g., Niemir et al. (1997) *Kidney Int.* 52:393-403). IL1α and IL1β are considered master regulators of SASP (see, e.g., Coppe et al. (2008) *PLoS. Biol.* 6: 2853-68). Glomerular disease is associated with elevated presence of senescent cells, especially in fibrotic kidneys (see, e.g., Sis et al. (2007) *Kidney Int.* 71:218-226).

Dermatological Disease or Disorder. Senescence-associated diseases or disorders treatable by administering a senolytic combination described herein include dermatological diseases or disorders. Such senescent cell associated diseases and disorders include psoriasis and eczema, which are also inflammatory diseases and are discussed in greater detail above. Other dermatological diseases and disorders that are associated with senescence include rhytides (wrinkles due to aging); pruritus (linked to diabetes and aging); dysesthesia (chemotherapy side effect that is linked to diabetes and multiple sclerosis); psoriasis (as noted) and other papulosquamous disorders, for example, erythroderma, lichen planus, and lichenoid dermatosis; atopic dermatitis (a form of eczema and associated with inflammation); eczematous eruptions (often observed in aging patients and linked to side effects of certain drugs). Other dermatological diseases and disorders associated with senescence include eosinophilic dermatosis (linked to certain kinds of hemotologic cancers); reactive neutrophilic dermatosis (associated with underlying diseases such as inflammatory bowel syndrome); pemphigus (an autoimmune disease in which autoantibodies form against desmoglein); pemphigoid and other immunobullous dermatosis (autoimmune blistering of skin); fibrohistocytic proliferations of skin, which is linked to aging; and cutaneous lymphomas that are more common in older populations. Another dermatological disease that may be treatable according to the methods described herein includes cutaneous lupus, which is a symptom of lupus erythematosus. Late onset lupus may be linked to decreased (i.e., reduced) function of T-cell and B-cells and cytokines (immunosenescence) associated with aging.

Metastasis. In a particular embodiment, methods are provided for treating or preventing (i.e., reducing the likelihood of occurrence or development of) a senescence cell associated disease (or disorder or condition), which is metastasis. The senolytic agents described herein may also be used according to the methods described herein for treating or preventing (i.e., reducing the likelihood of occurrence of) metastasis (i.e., the spreading and dissemination of cancer or tumor cells) from one organ or tissue to another organ or tissue in the body. Even though an agent as used in the combinations and methods described herein is not used in a manner that is sufficient to be considered as a primary cancer therapy, the methods and senolytic combinations described herein may be used in a manner (e.g., a short term course of therapy) that is useful for inhibiting metastases.

By way of explanation and example, one of the agents described herein for use in a senolytic combination is dasatinib, which is a compound used for treating chronic myelogenous leukemia (chronic Philadelphia chromosome+ CIVIL (CP-CML)) and acute lymphoblastic leukemia (ALL, Philadelphia chromosome positive). To treat these leukemias, dasatinib is administered to the patient daily at a dose between 100 and 140 mg/kg per day depending on the leukemia to be treated (see, e.g., SPRYCEL product label). In contrast, as an agent included in a senolytic combination, and as described in greater detail herein, dasatinib is administered significantly less often, such as for example, once every week or any number of days between 1-7 days every week; or once every two weeks or any number of days between 1-7 days every two weeks at minimum (e.g., once per 0.5-12 months) together with a second agent. In addition, dasatinib may be administered for treating the senescence associated diseases and disorders described herein at a lower dose per day, lower cumulative dose per treatment course, lower cumulative dose per treatment cycle, and a lower cumulative dose over 2 or more treatment cycles.

In one embodiment, methods are provided for preventing (i.e., reducing the likelihood of occurrence of), inhibiting, or retarding metastasis in a subject who has a cancer by administering a senolytic combination as described herein. In a particular embodiment, the senolytic combination is administered on one or more days within a treatment window (i.e., treatment course) of no longer than 1 day, 7 days, or 14 days. In other embodiments, the treatment course is no longer than 2, 3, 4, 5, 6, 7, 8, 9, 10, 11, 12, 13, 14, 15, 16, 17, 18, 19, 20, or no longer than 21 days. In other embodiments, the treatment course is a single day. In certain embodiments, the senolytic combination is administered on two or more days within a treatment window of no longer than 7 or 14 days, on 3 or more days within a treatment window of no longer than 7 or 14 days; on 4 or more days within a treatment window of no longer than 7 or 14 days; on 5 or more days within a treatment window of no longer than 7 or 14 days; on 6, 7, 8, 9, 10, 11, 12, 13, or 14 days within treatment window of no longer than 14 days. In certain embodiments, when the treatment window is 3 days or more, the treatment may be administered every 2"d day (i.e., every other day). In other certain embodiments when the treatment window is 4 days or more, the treatment may be administered every 3rd day (i.e., every other third day).

Because cells may be induced to senesce by cancer therapies, such as radiation and certain chemotherapy drugs (e.g., doxorubicin; paclitaxel; gemcitabine; pomalidomide; lenalidomide), a senolytic combination described herein may be administered after the chemotherapy or radiotherapy to kill (or facilitate killing) of these senescent cells. As discussed herein and understood in the art, establishment of senescence, such as shown by the presence of a senescence-associated secretory phenotype (SASP), occurs over several days (see, e.g., Laberge et al., *Aging Cell* 11:569-78 (2012); Coppe et al., *PLoS Biol* 6: 2853-68 (2008); Coppe et al. *PLoS One* 5:39188 (2010); Rodier et al., *Nat. Cell Biol.* 11:973-979; Freund et al., *EMBO J.* 30:1536-1548 (2011)). Therefore, administering a senolytic combination to kill senescent cells, and thereby reduce the likelihood of occurrence or reduce the extent of metastasis, is initiated when senescence has been established. As discussed herein, the following treatment courses for administration of the senolytic combination may be used in methods described herein for treating or preventing (i.e., reducing the likelihood of occurrence, or reducing the severity) a chemotherapy or radiotherapy side effect.

In certain embodiments, when chemotherapy or radiotherapy is administered in a treatment cycle of at least one day on-therapy (i.e., chemotherapy or radiotherapy)) followed by at least 3, 4, 5, 6, 7, 8, 9, 10, 11, 12, 13, 14 (or about 2 weeks), 15, 16, 17, 18, 19, 20, 21 (or about 3 weeks) days, or about 4 weeks (about one month) off-therapy (ie., off chemo- or radio-therapy), the senolytic combination is administered on one or more days during the off-therapy time interval (time period) beginning on or after the second day of the off-therapy time interval and ending on or before the last day of the off-therapy time interval. By way of illustrative example, if n is the number of days off-therapy, then the senolytic combination is administered on at least one day and no more than n–1 days of the off-therapy time interval. In a certain particular embodiment when chemotherapy or radiotherapy is administered in a treatment cycle of at least one day on-therapy (i.e., chemotherapy or radiotherapy)) followed by at least one week off-therapy, the senolytic combination is administered on one or more days during the off-therapy time interval beginning on or after the second day of the off-therapy time interval and ending on or before the last day of the off-therapy time interval. In a more specific embodiment, when chemotherapy or radiotherapy is administered in a treatment cycle of at least one day on-therapy (i.e., chemotherapy or radiotherapy)) followed by at least one week off-therapy, the senolytic combination is administered on one day that is the sixth day of the off-therapy time interval. In other specific embodiments, when chemotherapy or radiotherapy is administered in a treatment cycle of at least one day on-therapy (i.e., chemotherapy or radiotherapy)) followed by at least two weeks off-therapy, the senolytic combination is administered beginning on the sixth day of the off-chemo- or radio-therapy time interval and ending at least one day or at least two days prior to the first day of a subsequent chemotherapy or radiation therapy treatment course. By way of example, if the off-chemo- or radio-therapy time interval is two weeks, a senolytic combination may be administered on at least one and on no more than 7 days (i.e., 1, 2, 3, 4, 5, 6, or 7 days) of the off-therapy time interval beginning on the sixth day after the chemotherapy or radiotherapy course ends (i.e., the sixth day of the off chemo-radio-therapy interval). When the off-chemo- or radio-therapy time interval is at least three weeks, a senolytic combination may be administered on at least one day and on no more than 14 days (i.e., 1-14 days: 1, 2, 3, 4, 5, 6, 7, 8, 9, 10, 11, 12, 13, or 14 days) of the off-therapy time interval beginning on the sixth day after the chemotherapy or radiotherapy course ends. In other embodiments, depending on the off-chemo-radio-therapy interval, the senolytic combination treatment course is at least one day and no longer than 2, 3, 4, 5, 6, 7, 8, 9, 10, 11, 12, 13, 14, 15, 16, 17, 18, 19, 20, or no more than 21 days (i.e., 1-21 days), provided that administration of the senolytic combination is not concurrent with the chemotherapy or radiotherapy. In certain embodiments, the senolytic combination treatment course is a single day. In certain embodiments, the senolytic combination is administered on two or more days within a treatment window of no longer than 14 days, on 3 or more days within a treatment window of no longer than 14 days; on 4 or more days within a treatment window of no longer than 14 days; on 5 or more days within a treatment window of no longer than 14 days; on 6, 7, 8, 9, 10, 11, 12, 13, or 14 days within treatment window of no longer than 14 days. In certain embodiments, when the senolytic combination is administered to a subject during a treatment course of 3 days or more, the combination may be administered every $2^{nd}$ day (i.e., every other day). In other certain embodiments when the senolytic combination is administered to a subject during a treatment course of 4 days or more, the combination may be administered every 3rd day (i.e., every other third day).

Many chemotherapy and radiotherapy treatment regimens comprise a finite number of cycles of on-drug therapy followed by off-drug therapy or comprise a finite timeframe in which the chemotherapy or radiotherapy is administered. Such cancer treatment regimens may also be called treatment protocols. The protocols are determined by clinical trials, drug labels, and clinical staff in conjunction with the subject to be treated. The number of cycles of a chemotherapy or radiotherapy or the total length of time of a chemotherapy or radiotherapy regimen can vary depending on the patient's response to the cancer therapy. The timeframe for such treatment regimens is readily determined by a person skilled in the oncology art. In another embodiment for treating metastasis, a senolytic combination may be administered after the treatment regimen of chemotherapy or radiotherapy has been completed. In a particular embodiment, the senolytic combination is administered after the chemotherapy or radiotherapy has been completed on one or more days within treatment window (i.e., senolytic combination treatment course) of no longer than 14 days. In other embodiments, the senolytic combination treatment course is no longer than 2, 3, 4, 5, 6, 7, 8, 9, 10, 11, 12, 13, 14, 15, 16, 17, 18, 19, 20, or no more than 21 days. In other embodiments, the treatment course is a single day. In certain embodiments, the senolytic combination is administered on two or more days within a treatment window of no longer than 14 days, on 3 or more days within a treatment window of no longer than 14 days; on 4 or more days within a treatment window of no longer than 14 days; on 5 or more days within a treatment window of no longer than 14 days; on 6, 7, 8, 9, 10, 11, 12, 13, or 14 days within treatment window of no longer than 14 days. In certain embodiments, when the senolytic combination is administered to a subject after chemotherapy or radiotherapy for a treatment window of 3 days or more, the combination may be administered every $2^{nd}$ day (i.e., every other day). In other certain embodiments when the senolytic combination is administered to a subject for a treatment window of 4 days or more, the combination may be administered every 3rd day (i.e., every other third day). In one embodiment, the treatment with the senolytic combination may be initiated at least 1, 2, 3, 4, 5, 6, 7, 8, 9, 10, 11, 12, 13, or 14 days or later after the cancer treatment regimen has been completed. In a more particular embodiment, the treatment with the senolytic combination may be initiated at least 6, 7, 8, 9, 10, 11, 12, 13, or 14 days or later after the cancer treatment regimen has been completed. Any of the additional treatment courses and treatment cycles for administration of a senolytic combination described herein may be followed for inhibiting metastasis in a subject after a chemotherapy or radiotherapy protocol has been completed.

A chemotherapy may be referred to as a chemotherapy, chemotherapeutic, or chemotherapeutic drug. Many chemotherapeutics are compounds referred to as small organic molecules. Chemotherapy is a term that is also used to describe a combination chemotherapeutic drugs that are administered to treat a particular cancer. As understood by a person skilled in the art, a chemotherapy may also refer to a combination of two or more chemotherapeutic molecules that are administered coordinately and which may be referred to as combination chemotherapy. Numerous chemotherapeutic drugs are used in the oncology art and include, without limitation, alkylating agents; antimetabolites; anthracyclines, plant alkaloids; and topoisomerase inhibitors.

Metastasis of a cancer occurs when the cancer cells (i.e., tumor cells) spread beyond the anatomical site of origin and initial colonization to other areas throughout the body of the subject. A cancer that may metastasize may be a solid tumor or may be a liquid tumor (e.g., a leukemia). Cancers that are liquid tumors are classified in the art as those that occur in blood, bone marrow, and lymph nodes and include generally, leukemias (myeloid and lymphocytic), lymphomas (e.g., Hodgkin lymphoma), and melanoma (including multiple mycloma). Leukemias include for example, acute lymphoblastic leukemia (ALL), acute myeloid leukemia (AML), chronic lymphocytic leukemia (CLL), chronic myelogenous leukemia (CML), and hairy cell leukemia. Cancers that are solid tumors and occur in greater frequency in humans include, for example, prostate cancer, testicular cancer, breast cancer, brain cancer, pancreatic cancer, colon cancer, thyroid cancer, stomach cancer, lung cancer, ovarian cancer, Kaposi's sarcoma, skin cancer (including squamous cell skin cancer), renal cancer, head and neck cancers, throat cancer, squamous carcinomas that form on the moist mucosal linings of the nose, mouth, throat, etc.), bladder cancer, osteosarcoma (bone cancer), cervical cancer, endometrial cancer, esophageal cancer, liver cancer, and kidney cancer. In certain specific embodiments, the senescent cell-associated disease or disorder treated or prevented (i.e., likelihood of occurrence or development is reduced) by the methods described herein is metastasis of melanoma cells, prostate cancer cells, testicular cancer cells, breast cancer cells, brain cancer cells, pancreatic cancer cells, colon cancer cells, thyroid cancer cells, stomach cancer cells, lung cancer cells, ovarian cancer cells, Kaposi's sarcoma cells, skin cancer cells, renal cancer cells, head or neck cancer cells, throat cancer cells, squamous carcinoma cells, bladder cancer cells, osteosarcoma cells, cervical cancer cells, endometrial cancer cells, esophageal cancer cells, liver cancer cells, or kidney cancer cells.

The methods described herein are also useful for inhibiting, retarding or slowing progression of metastatic cancer of any one of the types of tumors described in the medical art. Types of cancers (tumors) include the following: adrenocortical carcinoma, childhood adrenocortical carcinoma, aids-related cancers, anal cancer, appendix cancer, basal cell carcinoma, childhood basal cell carcinoma, bladder cancer, childhood bladder cancer, bone cancer, brain tumor, childhood astrocytomas, childhood brain stem glioma, childhood central nervous system atypical teratoid/rhabdoid tumor, childhood central nervous system embryonal tumors, childhood central nervous system germ cell tumors, childhood craniopharyngioma brain tumor, childhood ependymoma brain tumor, breast cancer, childhood bronchial tumors, carcinoid tumor, childhood carcinoid tumor, gastrointestinal carcinoid tumor, carcinoma of unknown primary, childhood carcinoma of unknown primary, childhood cardiac (heart) tumors, cervical cancer, childhood cervical cancer, childhood chordoma, chronic myeloproliferative disorders, colon cancer, colorectal cancer, childhood colorectal cancer, extrahepatic bile duct cancer, ductal carcinoma in situ (dcis), endometrial cancer, esophageal cancer, childhood esophageal cancer, childhood esthesioneuroblastoma, eye cancer, malignant fibrous histiocytoma of bone, gallbladder cancer, gastric (stomach) cancer, childhood gastric (stomach) cancer, gastrointestinal stromal tumors (gist), childhood gastrointestinal stromal tumors (gist), childhood extracranial germ cell tumor, extragonadal germ cell tumor, gestational trophoblastic tumor, glioma, head and neck cancer, childhood head and neck cancer, hepatocellular (liver) cancer, hypopharyngeal cancer, kidney cancer, renal cell kidney cancer, Wilms tumor, childhood kidney tumors, Langerhans cell histiocytosis, laryngeal cancer, childhood laryngeal cancer, leukemia, acute lymphoblastic leukemia (all), acute myeloid leukemia (aml), chronic lymphocytic leukemia (ell), chronic myelogenous leukemia (cml), hairy cell leukemia, lip cancer, liver cancer (primary), childhood liver cancer (primary), lobular carcinoma in situ (lcis), lung cancer, non-small cell lung cancer, small cell lung cancer, lymphoma, aids-related lymphoma, burkitt lymphoma, cutaneous t-cell lymphoma, Hodgkin lymphoma, non-Hodgkin lymphoma, primary central nervous system lymphoma (cns), melanoma, childhood melanoma, intraocular (eye) melanoma, Merkel cell carcinoma, malignant mesothelioma, childhood malignant mesothelioma, metastatic squamous neck cancer with occult primary, midline tract carcinoma involving NUT gene, mouth cancer, childhood multiple endocrine neoplasia syndromes, mycosis fungoides, myelodysplastic syndromes, myelodysplastic neoplasms, myeloproliferative neoplasms, multiple myeloma, nasal cavity cancer, nasopharyngeal cancer, childhood nasopharyngeal cancer, neuroblastoma, oral cancer, childhood oral cancer, oropharyngeal cancer, ovarian cancer, childhood ovarian cancer, epithelial ovarian cancer, low malignant potential tumor ovarian cancer, pancreatic cancer, childhood pancreatic cancer, pancreatic neuroendocrine tumors (islet cell tumors), childhood papillomatosis, paraganglioma, paranasal sinus cancer, parathyroid cancer, penile cancer, pharyngeal cancer, pheochromocytoma, pituitary tumor, plasma cell neoplasm, childhood pleuropulmonary blastoma, prostate cancer, rectal cancer, renal pelvis transitional cell cancer, retinoblastoma, salivary gland cancer, childhood salivary gland cancer, ewing sarcoma family of tumors, Kaposi Sarcoma, osteosarcoma, rhabdomyosarcoma, childhood rhabdomyosarcoma, soft tissue sarcoma, uterine sarcoma, sezary syndrome, childhood skin cancer, nonmelanoma skin cancer, small intestine cancer, squamous cell carcinoma, childhood squamous cell carcinoma, testicular cancer, childhood testicular cancer, throat cancer, thymoma and thymic carcinoma, childhood thymoma and thymic carcinoma, thyroid cancer, childhood thyroid cancer, ureter transitional cell cancer, urethral cancer, endometrial uterine cancer, vaginal cancer, vulvar cancer, Waldenstrom Macroglobulinemia.

Chemotherapeutic and Radiotherapy Side Effects

In another embodiment, the senescence cell associated disorder or condition is a chemotherapeutic side effect or a radiotherapy side effect. A scnolytic combination administered as described herein may be used for treating and/or preventing (i.e., reducing the likelihood of occurrence of) a chemotherapeutic side effect or a radiotherapy side effect. Removal or destruction of senescent cells may ameliorate acute toxicity, including acute toxicity comprising energy imbalance, of a chemotherapy or radiotherapy. Acute toxic side effects include but are not limited to gastrointestinal toxicity (e.g., nausea, vomiting, constipation, anorexia, diarrhea), peripheral neuropathy, fatigue, malaise, low physical activity, hematological toxicity (e.g., anemia), hepatotoxicity, alopecia (hair loss), pain, infection, mucositis, fluid retention, dermatological toxicity (e.g., rashes, dermatitis, hyperpigmentation, urticaria, photosensitivity, nail changes), mouth, gum or throat problems, or any toxic side effect caused by a chemotherapy or radiotherapy. For example, toxic side effects caused by radiotherapy or chemotherapy (see, e.g., National Cancer Institute web site) may be ameliorated by the methods described herein. Accordingly, in certain embodiments, methods are provided herein for ameliorating (reducing, inhibiting, or preventing occurrence (i.e., reducing the likelihood of occurrence)) acute toxicity or reducing severity of a toxic side effect (i.e., deleterious side effect) of a chemotherapy or radiotherapy or both in a subject who receives the therapy, wherein the method comprises administering to the subject an agent that selectively kills, removes, or destroys or facilitates selective destruction of senescent cells. Administration of a senolytic combination for treating or reducing the likelihood of occurrence, or reducing the severity of a chemotherapy or radiotherapy side effect may be accomplished by the same treatment courses described above for treatment/prevention of metastasis. As described for treating or preventing (i.e., reducing the likelihood of occurrence of) metastasis, the senolytic combination is administered during the off-chemotherapy or off-radiotherapy time interval or after the chemotherapy or radiotherapy treatment regimen has been completed.

In a more specific embodiment, the acute toxicity is an acute toxicity comprising energy imbalance and may comprise one or more of weight loss, endocrine change(s) (e.g., hormone imbalance, change in hormone signaling), and change(s) in body composition. In certain embodiments, an acute toxicity comprising energy imbalance relates to decreased or reduced ability of the subject to be physically active, as indicated by decreased or diminished expenditure of energy than would be observed in a subject who did not receive the medical therapy. By way of non-limiting example, such an acute toxic effect that comprises energy imbalance includes low physical activity. In other particular embodiments, energy imbalance comprises fatigue or malaise.

In one embodiment, a chemotherapy side effect to be treated or prevented (i.e., likelihood of occurrence is reduced) by a senolytic combination described herein is cardiotoxicity. In one embodiment, the cardiotoxicity results from administration of doxorubicin. Doxorubicin is an anthracycline topoisomerase is approved for treating patients who have ovarian cancer after failure of a platinum based therapy; Kaposi's sarcoma after failure of primary systemic chemotherapy or intolerance to the therapy; or multiple myeloma in combination with bortezomib in patients who have not previously received bortezomib or who have received at least one prior therapy. Doxorubicin may cause myocardial damage that could lead to congestive heart failure if the total lifetime dose to a patient exceeds 550 mg/m$^2$. Cardiotoxicity may occur at even lower doses if the patient also receives mediastinal irradiation or another cardiotoxic drug. See drug product inserts (e.g., DOXIL, ADRIAMYCIN).

In other embodiments, a senolytic combination may be used in the methods as provided herein for ameliorating chronic or long term side effects. Chronic toxic side effects typically result from multiple exposures to or administrations of a chemotherapy or radiotherapy over a longer period of time. Certain toxic effects appear long after treatment (also called late toxic effects) and result from damage to an organ or system by the therapy. Organ dysfunction (e.g., neurological, pulmonary, cardiovascular, and endocrine dysfunction) has been observed in patients who were treated for cancers during childhood (see, e.g., Hudson et al., *JAMA* 309:2371-81 (2013)). Without wishing to be bound by any particular theory, by destroying senescent cells, particular normal cells that have been induced to senescence by chemotherapy or radiotherapy, the likelihood of occurrence of a chronic side effect may be reduced, or the severity of a chronic side effect may be reduced or diminished, or the time of onset of a chronic side effect may be delayed. Chronic and/or late toxic side effects that occur in subjects who received chemotherapy or radiation therapy include by way of non-limiting example, cardiomyopathy, congestive heart disease, inflammation, early menopause, osteoporosis, infertility, impaired cognitive function, peripheral neuropathy, secondary cancers, cataracts and other vision problems, hearing loss, chronic fatigue, reduced lung capacity, and lung disease.

Administration of a senolytic combination for treating or reducing the likelihood of occurrence, or reducing the severity of a chemotherapy or radiotherapy side effect may be accomplished by the same treatment courses described above for treatment/prevention of metastasis. As with treating or preventing metastasis, the senolytic combination is administered during the off-chemotherapy or off-radiotherapy time interval or after the chemotherapy or radiotherapy treatment regimen has been completed.

Age Related Diseases and Disorders. A senolytic combination may also be useful for treating or preventing (i.e., reducing the likelihood of occurrence) of an age-related disease or disorder that occurs as part of the natural aging process or that occurs when the subject is exposed to a senescence inducing agent or factor (e.g., irradiation, chemotherapy, smoking tobacco, high-fat/high sugar diet, other environmental factors). An age-related disorder or disease or an age-sensitive trait may be associated with a senescence-inducing stimulus. The efficacy of a method of treatment described herein may be manifested by reducing the number of symptoms of an age-related disorder or age-sensitive trait associated with a senescence-inducing stimulus, decreasing the severity of one or more symptoms, or delaying the progression of an age-related disorder or age-sensitive trait associated with a senescence-inducing stimulus. In other particular embodiments, preventing an age-related disorder or age-sensitive trait associated with a senescence-inducing stimulus refers to preventing (i.e., reducing the likelihood of occurrence) or delaying onset of an age-related disorder or age-sensitive trait associated with a senescence-inducing stimulus, or reoccurrence of one or more age-related disorder or age-sensitive trait associated with a senescence-inducing stimulus. Age related diseases or conditions include, for example, renal dysfunction, kyphosis, herniated intervertebral disc, frailty, hair loss, hearing loss, vision loss (blindness or impaired vision), muscle fatigue, skin conditions, skin nevi, diabetes, metabolic syndrome, and sarcopenia. Vision loss refers to the absence of vision when a subject previously had vision. Various scales have been developed to describe the extent of vision and vision loss based on visual acuity. Age-related diseases and conditions also include dermatological conditions, for example without limitation, treating one or more of the following conditions: wrinkles, including superficial fine wrinkles; hyperpigmentation; scars; keloid; dermatitis; psoriasis; eczema (including seborrheic eczema); rosacca; vitiligo; ichthyosis vulgaris; dermatomyositis; and actinic keratosis.

Frailty has been defined as a clinically recognizable state of increased vulnerability resulting from aging-associated decline in reserve and function across multiple physiologic systems that compromise a subject's ability to cope with every day or acute stressors. Frailty has been may be characterized by compromised energetics characteristics such as low grip strength, low energy, slowed waking speed, low physical activity, and/or unintentional weight loss. Studies have suggested that a patient may be diagnosed with frailty when three of five of the foregoing characteristics are observed (see, e.g., Fried et al., *J. Gerontol. A Biol. Sci. Med, Sci.* 2001; 56(3):M146-M156; Xue, *Clin. Geriatr. Med.* 2011; 27(1):1-15). In certain embodiments, aging and diseases and disorders related to aging may be treated or prevented (i.e., the likelihood of occurrence of is reduced) by administering a senolytic combination. The senolytic combination may inhibit senescence of adult stem cells or inhibit accumulation, kill, or facilitate removal of adult stem cells that have become senescent. See, e.g., Park et al., *J. Clin. Invest.* 113:175-79 (2004) and Sousa-Victor, *Nature* 506:316-21 (2014) describing importance of preventing senescence in stem cells to maintain regenerative capacity of tissues.

The effectiveness of a senolytic combination with respect to treating a senescence-associated disease or disorder described herein can readily be determined by a person skilled in the medical and clinical arts. One or any combination of diagnostic methods appropriate for the particular disease or disorder, which methods are well known to a person skilled in the art, including physical examination, patient self-assessment, assessment and monitoring of clinical symptoms, performance of analytical tests and methods, including clinical laboratory tests, physical tests, and exploratory surgery, for example, may be used for monitoring the health status of the subject and the effectiveness of the senolytic combination. The effects of the methods of treatment described herein can be analyzed using techniques known in the art, such as comparing symptoms of patients suffering from or at risk of a particular disease or disorder that have received the pharmaceutical composition comprising a senolytic combination with those of patients who were not treated with the senolytic combination or who received a placebo treatment.

Methods of Use

Provided herein are methods for selectively killing senescent cells that result in treating a senescence-associated disease or disorder and comprises use of a senolytic combination as described herein. As described herein, the senolytic combination is administered in a manner that would be considered ineffective for treating a cancer. Because the method used for treating a senescence associated disease with a senolytic combination described herein comprises one or more of a decreased daily dose or each compound of the combination, decreased cumulative dose over a single therapeutic cycle, or decreased cumulative dose of the senolytic combination over multiple therapeutic cycles compared with the amount of the combination (or each compound alone) required for cancer therapy, the likelihood is decreased that one or more adverse effects (i.e., side effects) will occur, which adverse effects are associated with treating a subject according to a regimen optimized for treating a cancer.

The methods and senolytic combinations for selective killing of senescent cells may be used for treating and/or preventing (i.e., decreasing the likelihood of occurrence) of numerous age-related pathologies and diseases as described herein. As disclosed herein, senescent cell associated diseases and disorders may be treated or prevented (i.e., the likelihood of occurrence of is reduced) by administering a senolytic combination comprising at least two agents, and which agents alter either a cell survival signaling pathway or an inflammatory pathway or alters both the cell survival signaling pathway and the inflammatory pathway. The senolytic combinations described herein, and pharmaceutical compositions comprising the combinations, are useful for treating, reducing the likelihood of occurrence of, or delaying onset of a senescent cell-associated disease or disorder in a subject who has a senescent cell-associated disease or disorder or who has at least one predisposing factor for developing the senescent cell-associated disease or disorder. The combinations that comprise at least two agents (e.g., dasatinib and quercetin or an analog thereof), and at least one agent (for convenience, referred to herein as a first agent) and a second agent are different and each independently alters either one or both of a survival signaling pathway and an inflammatory pathway.

In one embodiment, a method is provided for treating a subject who has a senescent cell associated disease or disorder or for prophylaxis (e.g., for reducing the likelihood of occurrence of or delaying onset) of a senescent cell-associated disease or disorder in a subject who has at least one predisposing factor for developing the senescent cell-associated disease or disorder, which method comprises administering to the subject a senolytic combination that alters either one or both of a cell survival signaling pathway and an inflammatory pathway in the senescent cell. Also provided is a method for killing a senescent cell, comprising contacting a senescent cell and the agents of the combination, which agents alters either one or both of a cell survival signaling pathway and an inflammatory pathway in the senescent cell. In a particular embodiment, the senescent cell is present in a subject who has a senescent cell associated disease or disorder or who has at least one predisposing factor for developing the senescent cell-associated disease or disorder. In certain embodiments, the senescent cell-associated disease or disorder is a cardiovascular disease or disorder (e.g., atherosclerosis), inflammatory disease or disorder (e.g., osteoarthritis), a pulmonary disease or disorder (e.g., idiopathic pulmonary fibrosis; chronic obstructive pulmonary disease), a neurological disease or disorder (e.g., Parkinson's disease, Alzheimer's disease, macular degeneration, MCI, MND), a chemotherapeutic side effect (e.g., an acute or chronic toxic effect; cardiotoxicity), a radiotherapy side effect (e.g., an acute or chronic toxic effect), or metastasis of any tumor type described herein. In certain other embodiments, the senescent cell-associated disease or disorder is a metabolic disease or disorder, including for example, diabetes, obesity, or metabolic syndrome.

In certain embodiments, a senolytic agent or a senolytic combination is administered within a treatment cycle, which treatment cycle comprises a treatment course followed by a non-treatment interval. A treatment course of administration refers herein to a finite time frame over which one or more doses of the senolytic combination on one or more days are administered. The finite time frame may be also called herein a treatment window. In one embodiment, the treatment course is between about 1-7 days (i.e., 1, 2, 3, 4, 5, 6, or 7 days) every 0.5-12 months; provided that if the senescence associated disease or disorder is a senescence associated metabolic disorder, the senolytic combination is administered during a treatment course of about 1-7 days (i.e., 1, 2, 3, 4, 5, 6, or 7 days) every 4-12 months. In certain embodiments, the treatment course is only one day. In other specific embodiments, the senolytic combination may be administered at time intervals as follows: once every 1, 2, 3, 4, 5, or 6 days or every week, every 2 weeks (or once per 0.5 month), every 3 weeks, every 4 weeks (or once per month), every 2 months, every 3 months, every 4 months, every 5 months, every 6 months, every 7 months, every 8 months, every 9 months, every 10 months, every 11 months, or every 12 months (or once a year) or once at longer intervals. The time interval when the senolytic combination is not administered is also called herein a non-treatment interval or off-treatment. In certain embodiments, the senolytic combination is administered once every 0.5 month-12 months (i.e., once every 2 weeks (about 0.5 month), once every 2 months, once every 3 months, once every 4 months, once every 5 months, once every 6 months, every 7 months, once every 8 months, once every 9 months, once every 10 months, once every 11 months, or once every 12 months (or once a year)). In other particular embodiments, the senolytic combination is administered once every 4-12 months (i.e., once every 4 months, once every 5 months, once every 6 months, every 7 months, once every 8 months, once every 9 months, once every 10 months, once every 11 months, or once every 12 months). In other specific embodiments, a senolytic combination may be administered daily for one week, one month, 6 weeks, or 2 months; a next treatment course of daily dosing for one week, one month, 6 weeks, or 2 months may be initiated 2 days, 3 days, 4 days, 5 days, 6 days, one week, two weeks, three weeks, one month, 2 months, 3 months or longer after the treatment course is completed. In other words, the non-treatment interval is at least about 2 days, 3 days, 4 days, 5 days, 6 days, one week, two weeks, three weeks, one month, 2 months, 3 months or longer. In certain embodiments, the non-treatment interval is 4 months, 5 months, 6 months, 7 months, 8 months, 9 months, 10 months, 11 months, or a year. In other embodiments, a senolytic combination may be administered during a treatment course of once or twice daily for 8, 9, 10, 11, 12, 13, or 14 days followed by 1, 2, 3, 4, 5, 6, 7, 8, 9, 10, 11, 12, 13, or 14 days with no administration of the combination (i.e., non-treatment interval) followed by another treatment course of once or twice daily administration of the combination for 8, 9, 10, 11, 12, 13, or 14 days. These cycles of administering a combination, followed by a non-treatment interval may be repeated as needed for treatment or prophylaxis of the particular subject's disease or disorder. The amount of the dose administered according to any of the aforementioned dosing regimens may administered as single total dose on the day of administration, or the total dose for the day's administration may be divided into multiple aliquots, such as 2, 3, 4, or 5 separate doses on the day of administration. The dosing regimens (e.g., the time interval between doses) can be reviewed and modified or adjusted, continued or discontinued, as determined by a person skilled in the art, depending on the responsiveness of the subject to the therapy, the stage of the disease, the general health of the subject, and other factors that are described herein and in the art.

In a more particular embodiment, methods are provided that comprise administering a senolytic agent or a senolytic combination once every 0.5-12 months to a subject who has a senescent cell-associated disease or disorder or who has at least one predisposing risk factor for developing the disease or disorder, which disease or disorder is any one of a cardiovascular disease or disorder, inflammatory disease or disorder, a pulmonary disease or disorder, a neurological disease or disorder, a chemotherapeutic side effect, a radiotherapy side effect, or metastasis. In another particular embodiment, a method is provided for killing a senescent cell by contacting the senescent cell with a senolytic combination, in a subject by administering the senolytic combination once every 0.5-12 months. In other particular embodiments, the combination is administered on 1, 2, 3, 4, 5, 6, or 7 days every 0.5-12 months.

In still another embodiment, a method of treatment or prophylaxis of a senescent cell associated disease or disorder is provided wherein a senolytic agent or a senolytic combination is administered once every 4-12 months to a subject who has a senescent cell-associated disease or disorder or who has at least one predisposing risk factor for developing the disease or disorder, which may be any one of a cardiovascular disease or disorder, inflammatory disease or disorder, a pulmonary disease or disorder, a neurological disease or disorder, a metabolic disease or disorder, a chemotherapeutic side effect, a radiotherapy side effect, or metastasis. In an even more specific embodiment, the senescent cell associated disease or disorder is a metabolic disease such as obesity, metabolic syndrome, or diabetes. In other particular embodiments, the treatment is administered on 1, 2, 3, 4, 5, 6, or 7 days every 4-12 months.

In yet other embodiments, a method is provided for killing a senescent cell by contacting the senescent cell with a senolytic agent or a senolytic combination, in a subject by administered once every 4-12 months to a subject who has a senescent cell-associated disease or disorder or who has at least one predisposing risk factor for developing the disease or disorder, which may be any one of a cardiovascular disease or disorder, inflammatory disease or disorder, a pulmonary disease or disorder, a neurological disease or disorder, a metabolic disease or disorder, a chemotherapeutic side effect, a radiotherapy side effect, or metastasis. In an even more specific embodiment, the senescent cell associated disease or disorder is a metabolic disease such as obesity, metabolic syndrome, or diabetes. In other particular embodiments, the combination is administered on 1, 2, 3, 4, 5, 6, or 7 days every 4-12 months.

The agents of the combination may be administered together at the administered on the same day (i.e., concurrently), at the same time or at different times. For example, one agent of the combination may be administered before meals and the second agent of the combination administered after meals, or one agent may be administered in the morning and the second agent in the evening. The first or second agents, or both, administered according to any of the aforementioned dosing regimens may administered as single total dose on the day of administration, or the total dose for the day's administration may be divided into multiple aliquots, such as 2, 3, 4, or 5 separate doses on the day of administration. Each agent of the combination may be administered via the same administrative route or by different administrative routes.

The treatment cycles of administering the senolytic combination may be repeated as needed for treatment or prophylaxis of the particular subject's disease or disorder. The treatment course and non-treatment interval can be reviewed and modified or adjusted, continued or discontinued, by a person skilled in the art, depending on the responsiveness of the subject to the therapy, the stage of the disease, the general health of the subject, and other factors that are described herein and in the art. Accordingly, in certain embodiments, one cycle of treatment is followed by a subsequent cycle of treatment. Each treatment course of a treatment cycle or each treatment course of two or more treatment cycles are typically the same in duration and dosing of the senolytic agent. In other embodiments, the duration and dosing of the senolytic agent during each treatment course of a treatment cycle may be adjusted as determined by a person skilled in the medical art depending, for example, on the particular disease or disorder being treated, the senolytic agent being administered, the health status of the patient and other relevant factors, which are discussed in greater detail herein. Accordingly, a treatment course of a second or any subsequent treatment cycle may be shortened or lengthened as deemed medically necessary or prudent. In other words, as would be appreciated by a person skilled in the art, each treatment course of two or more treatment cycles and each non-treatment interval may be independent and the same or different.

In other embodiments, when two agents are administered in combination for treatment or prophylaxis of a senescent cell associated disease or disorder or for killing a senescent cell, the dosing regimen of the first agent may be different than the dosing regimen of the second agent, such as sequential administration. For example, sequential administration may include administering a first agent and then 1 or 2 days later the second agent is administered; in such embodiments, the time interval between dosing of each respective agent would be the same so that the time interval between administration of the first and second agents is maintained. Administration of two agents of the combination must be sufficiently close in time so that the two agents act together to selectively kill senescent cells.

In embodiments when a third agent is administered, the third agent may be administered according to the same dosing regimen as the first agent or the second agent.

In particular embodiments, as described herein, such as when the subject has a cancer, the senolytic combination is not intended to be used as a primary therapy or as a component of a primary therapy for the treatment of the cancer. By way of illustration, dasatinib is administered daily for treatment of certain leukemias; however, as described herein, dasatinib in combination with a second agent is not be used in the same manner as when it is a primary therapy for the treatment of the cancer. For example, a subject who has a cancer and is being treated with an anthracycline (such as doxorubicin, daunorubicin) may receive a senolytic combination described herein that reduces, ameliorates, or decreases the cardiotoxicity of the anthracycline. As is well understood in the medical art, because of the cardiotoxicity associated with anthracyclines, the maximum lifetime dose that a subject can receive is limited even if the cancer is responsive to the drug. Administration of a senolytic combination may reduce the cardiotoxicity such that additional amounts of the anthracycline can be administered to the subject, resulting in an improved prognosis related to cancer disease.

Therapeutic and/or prophylactic benefit for subjects to whom the senolytic combination is administered, includes, for example, an improved clinical outcome, wherein the object is to prevent or slow or retard (lessen) an undesired physiological change associated with the disease, or to prevent or slow or retard (lessen) the expansion or severity of such disease. As discussed herein, effectiveness of a senolytic combination may include beneficial or desired clinical results that comprise, but are not limited to, abatement, lessening, or alleviation of symptoms that result from or are associated with the disease to be treated; decreased occurrence of symptoms; improved quality of life; longer disease-free status (i.e., decreasing the likelihood or the propensity that a subject will present symptoms on the basis of which a diagnosis of a disease is made); diminishment of extent of disease; stabilized (i.e., not worsening) state of disease; delay or slowing of disease progression; amelioration or palliation of the disease state; and remission (whether partial or total), whether detectable or undetectable; and/or overall survival. The effectiveness of the senolytic combinations described herein may also mean prolonging survival when compared to expected survival if a subject were not receiving the combination that selectively kills senescent cells.

One or any combination of diagnostic methods appropriate for the particular disease or disorder, which methods are well known to a person skilled in the art and described herein, including physical examination, patient self-assessment, assessment and monitoring of clinical symptoms, performance of analytical tests and methods, including clinical laboratory tests, physical tests, and exploratory surgery, for example, may be used for monitoring the health status of the subject and the effectiveness of the treatment. The effects of the methods of treatment described herein can be analyzed using techniques known in the art, such as comparing symptoms of patients suffering from or at risk of a particular disease or disorder that have received the pharmaceutical composition comprising a senolytic combination, for example, with those of patients who were not treated with the senolytic combination or who received a placebo treatment.

As understood by a person skilled in the medical art, the terms, "treat" and "treatment," refer to medical management of a disease, disorder, or condition of a subject (i.e., patient) (see, e.g., Stedman's Medical Dictionary). In general, an appropriate dose and treatment regimen provide the therapeutic agent (e.g., a senolytic combination) in an amount sufficient to provide therapeutic and/or prophylactic benefit. Therapeutic benefit for subjects to whom the treatments (e.g., senolytic combinations) described herein are administered, includes, for example, an improved clinical outcome, wherein the object is to prevent or slow or retard (lessen) an undesired physiological change associated with the disease, or to prevent or slow or retard (lessen) the expansion or severity of such disease. As discussed herein, effectiveness of the combinations and compositions described herein may include beneficial or desired clinical results that comprise, but are not limited to, abatement, lessening, or alleviation of symptoms that result from or are associated with the disease to be treated; decreased occurrence of symptoms; improved quality of life; longer disease-free status (i.e., decreasing the likelihood or the propensity that a subject will present symptoms on the basis of which a diagnosis of a disease is made); diminishment of extent of disease; stabilized (i.e., not worsening) state of disease;

delay or slowing of disease progression; amelioration or palliation of the disease state; and remission (whether partial or total), whether detectable or undetectable; and/or overall survival. Effectiveness of the treatments described herein may also mean prolonging survival when compared to expected survival if a subject were not receiving the treatment that selectively kills senescent cells.

Administration of a treatment (e.g., a senolytic combination) described herein can prolong survival when compared to expected survival if a subject were not receiving treatment. Subjects in need of treatment include those who already have the disease or disorder as well as subjects prone to have or at risk of developing the disease or disorder, and those in which the disease, condition, or disorder is to be treated prophylactically. A subject may have a genetic predisposition for developing a disease or disorder that would benefit from clearance of senescent cells or may be of a certain age wherein receiving a senolytic combination would provide clinical benefit to delay development or reduce severity of a disease, including an age-related disease or disorder.

A subject, patient, or individual in need of treatment may be a human or may be a non-human primate or other non-human animal (i.e., veterinary use) who has developed symptoms of a senescence cell-associated disease or disorder or who is at risk for developing a senescence cell-associated disease or disorder. Examples of non-human primates and other animals include but are not limited to farm animals, pets, and zoo animals (e.g., horses, cows, buffalo, llamas, goats, rabbits, cats, dogs, chimpanzees, orangutans, gorillas, monkeys, elephants, bears, large cats, etc.).

Pharmaceutical Compositions

Also provided herein are pharmaceutical compositions comprising the senolytic combinations described herein. A pharmaceutical composition may be a sterile aqueous or non-aqueous solution, suspension or emulsion, which additionally comprises a physiologically acceptable excipient (pharmaceutically acceptable or suitable excipient or carrier) (i.e., a non-toxic material that does not interfere with the activity of the active ingredient). The excipients described herein are merely exemplary and are in no way limiting. An effective amount or therapeutically effective amount refers to an amount of an agent or combination of agents or a composition comprising the one or more agents administered to a subject, either as a single dose or as part of a series of doses, which is effective to produce a desired therapeutic effect.

When a senolytic combination is administered to a subject for treatment of a disease or disorder described herein, each of the agents of the combination may be formulated into separate pharmaceutical compositions. A pharmaceutical preparation may be prepared that comprises each of the separate pharmaceutical compositions (which may be referred to for convenience, for example, as a first pharmaceutical composition and a second pharmaceutical composition comprising each of the first and second agents, respectively). Each of the pharmaceutical compositions in the preparation may be administered at the same time and via the same route of administration or may be administered at different times by the same or different administration routes. Alternatively, two or more agents of the combination may be formulated together in a single pharmaceutical composition.

Subjects may generally be monitored for therapeutic effectiveness using assays and methods suitable for the condition being treated or prevented, which assays will be familiar to those having ordinary skill in the art and are described herein. The level of an agent that is administered to a subject may be monitored by determining the level of the agent in a biological fluid, for example, in the blood, blood fraction (e.g., serum), and/or in the urine, and/or other biological sample from the subject. Any method practiced in the art to detect the agent may be used to measure the level of agent during the course of a therapeutic regimen.

The dose of each agent of a combination described herein for treating a senescence cell associated disease or disorder may depend upon the subject's condition, that is, stage of the disease, severity of symptoms caused by the disease, general health status, as well as age, gender, and weight, and other factors apparent to a person skilled in the medical art. Pharmaceutical compositions may be administered in a manner appropriate to the disease to be treated as determined by persons skilled in the medical arts. A suitable duration and frequency of administration may also be determined by such factors as the condition of the patient, the type and severity of the patient's disease, the particular form of the active ingredient, and the method of administration. Optimal doses of each agent of the combination may generally be determined using experimental models and/or clinical trials. The optimal dose may depend upon the body mass, weight, or blood volume of the subject. The use of the minimum dose that is sufficient to provide effective therapy is usually preferred. Design and execution of pre-clinical and clinical studies for a combination (including when administered for prophylactic benefit) described herein are well within the skill of a person skilled in the relevant art. The optimal dose of a senolytic combination may depend upon the body mass, weight, or blood volume of the subject. Each agent of the combination may be of an amount between 0.01 mg/kg and 1000 mg/kg (e.g., about 0.1 to 1 mg/kg, about 1 to 10 mg/kg, about 10-50 mg/kg, about 50-100 mg/kg, about 100-500 mg/kg, or about 500-1000 mg/kg) body weight.

The pharmaceutical compositions may be administered to a subject in need by any one of several routes that effectively deliver an effective amount of the combination. Pharmaceutical compositions comprising a senolytic combination can be formulated in a manner appropriate for the delivery method by using techniques routinely practiced in the art. The composition may be in the foiiii of a solid (e.g., tablet, capsule), semi-solid (e.g., gel), liquid, or gas (aerosol). In other certain specific embodiments, the senolytic combination (or pharmaceutical composition comprising same) is administered as a bolus infusion. In certain embodiments when the senolytic combination is delivered by infusion, the senolytic combination is delivered to an organ or tissue comprising senescent cells to be killed via a blood vessel in accordance with techniques routinely performed by a person skilled in the medical art.

Pharmaceutical acceptable excipients are well known in the pharmaceutical art and described, for example, in Rowe et al., Handbook of Pharmaceutical Excipients: A Comprehensive Guide to Uses, Properties, and Safety, 5$^{th}$ Ed., 2006, and in *Remington: The Science and Practice of Pharmacy* (Gennaro, 21st Ed. Mack Pub. Co., Easton, Pa. (2005)). Exemplary pharmaceutically acceptable excipients include sterile saline and phosphate buffered saline at physiological pH. Preservatives, stabilizers, dyes, buffers, and the like may be provided in the pharmaceutical composition. In addition, antioxidants and suspending agents may also be used. In general, the type of excipient is selected based on the mode of administration, as well as the chemical composition of the active ingredient(s). Alternatively, compositions described herein may be formulated as a lyophilizate, or the agent may be encapsulated within liposomes using technology known in the art. A composition described herein may be lyophilized or otherwise formulated as a lyophilized product using one or more appropriate excipient solutions for solubilizing and/or diluting the agent(s) of the composition upon administration. In other embodiments, the agent may be encapsulated within liposomes using technology known and practiced in the art. Pharmaceutical compositions may be formulated for any appropriate manner of administration described herein and in the art.

A pharmaceutical composition may be delivered to a subject in need thereof by any one of several routes known to a person skilled in the art. By way of non-limiting example, the composition may be delivered orally, intravenously, intraperitoneally, by infusion (e.g., a bolus infusion), subcutaneously, enteral, rectal, intranasal, by inhalation, buccal, sublingual, intramuscular, transdermal, intradermal, topically, intraocular, vaginal, rectal, or by intracranial injection, or any combination thereof. In certain particular embodiments, administration of a dose as described above is via intravenous, intraperitoneal, directly into the target tissue or organ, or subcutaneous route. In certain embodiments, a delivery method includes drug-coated or permeated stents for which the drug is the senolytic agent. Formulations suitable for such delivery methods are described in greater detail herein.

A pharmaceutical composition (e.g., for oral administration or delivery by injection) may be in the form of a liquid. A liquid pharmaceutical composition may include, for example, one or more of the following: a sterile diluent such as water for injection, saline solution, preferably physiological saline, Ringer's solution, isotonic sodium chloride, fixed oils that may serve as the solvent or suspending medium, polyethylene glycols, glycerin, propylene glycol or other solvents; antibacterial agents; antioxidants; chelating agents; buffers and agents for the adjustment of tonicity such as sodium chloride or dextrose. A parenteral preparation can be enclosed in ampoules, disposable syringes or multiple dose vials made of glass or plastic. The use of physiological saline is preferred, and an injectable pharmaceutical composition is preferably sterile.

In certain particular embodiments, a senolytic combination (which may be combined with at least one pharmaceutically acceptable excipient to form a pharmaceutical composition) is administered directly to the target tissue or organ comprising senescent cells that contribute to manifestation of the disease or disorder. In specific embodiments when treating osteoarthritis, the senolytic combination is administered directly to an osteoarthritic joint (i.e., intra-articularly) of a subject in need thereof. In other specific embodiments, a senolytic combination may be administered to the joint via topical, transdermal, intradermal, or subcutaneous route. In other certain embodiments, methods are provided herein for treating a cardiovascular disease or disorder associated with arteriosclerosis, such as atherosclerosis by administering directly into an artery. In another particular embodiment, a senolytic combination (which may be combined with at least one pharmaceutically acceptable excipient to form a pharmaceutical composition) for treating a senescent-associated pulmonary disease or disorder may be administered by inhalation, intranasally, by intubation, or intracheally, for example, to provide the senolytic combination more directly to the affected pulmonary tissue. By way of another non-limiting example, the senolytic combination (or pharmaceutical composition comprising the senolytic combination) may be delivered directly to the eye either by injection (e.g., intraocular or intravitreal) or by conjunctival application underneath an eyelid of a cream, ointment, gel, or eye drops. In more particular embodiments, the senolytic combination or pharmaceutical composition comprising the senolytic combination may be formulated as a timed release (also called sustained release, controlled release) composition or may be administered as a bolus infusion.

A pharmaceutical composition (e.g., for oral administration or for injection, infusion, subcutaneous delivery, intramuscular delivery, intraperitoneal delivery or other method) may be in the form of a liquid. A liquid pharmaceutical composition may include, for example, one or more of the following: a sterile diluent such as water, saline solution, preferably physiological saline, Ringer's solution, isotonic sodium chloride, fixed oils that may serve as the solvent or suspending medium, polyethylene glycols, glycerin, propylene glycol or other solvents; antibacterial agents; antioxidants; chelating agents; buffers and agents for the adjustment of tonicity such as sodium chloride or dextrose. A parenteral composition can be enclosed in ampoules, disposable syringes or multiple dose vials made of glass or plastic. The use of physiological saline is preferred, and an injectable pharmaceutical composition is preferably sterile. In another embodiment, for treatment of an ophthalmological condition or disease, a liquid pharmaceutical composition may be applied to the eye in the form of eye drops. A liquid pharmaceutical composition may be delivered orally.

For oral formulations, the senolytic combinations described herein can be used alone or in combination with appropriate additives to make tablets, powders, granules or capsules, and if desired, with diluents, buffering agents, moistening agents, preservatives, coloring agents, and flavoring agents. The compounds of the combination, each alone or together, may be formulated with a buffering agent to provide for protection of the compound from low pH of the gastric environment and/or an enteric coating. A senolytic combination (or each agent of the combination) included in a pharmaceutical composition may be formulated for oral delivery with a flavoring agent, e.g., in a liquid, solid or semi-solid formulation and/or with an enteric coating.

A pharmaceutical composition comprising the senolytic combinations described herein may be formulated for sustained or slow release (also called timed release or controlled release). Such compositions may generally be prepared using well known technology and administered by, for example, oral, rectal, intradermal, or subcutaneous implantation, or by implantation at the desired target site. Sustained-release formulations may contain the compounds of the combination dispersed in a carrier matrix and/or contained within a reservoir surrounded by a rate controlling membrane. Excipients for use within such formulations are biocompatible, and may also be biodegradable; preferably the formulation provides a relatively constant level of active component release. The amount of active agent contained within a sustained release formulation depends upon the site of implantation, the rate and expected duration of release, and the nature of the condition, disease or disorder to be treated or prevented.

In certain embodiments, the pharmaceutical compositions comprising a senolytic combination are formulated for transdermal, intradermal, or topical administration. The compositions can be administered using a syringe, bandage, transdermal patch, insert, or syringe-like applicator, as a powder/talc or other solid, liquid, spray, aerosol, ointment, foam, cream, gel, paste. This preferably is in the form of a controlled release formulation or sustained release formulation administered topically or injected directly into the skin adjacent to or within the area to be treated (intradermally or subcutaneously). The active compositions can also be delivered via iontophoresis. Preservatives can be used to prevent the growth of fungi and other microorganisms. Suitable preservatives include, but are not limited to, benzoic acid, butylparaben, ethyl paraben, methyl paraben, propylparaben, sodium benzoate, sodium propionate, benzalkonium chloride, benzethonium chloride, benzyl alcohol, cetypyridinium chloride, chlorobutanol, phenol, phenylethyl alcohol, thimerosal, and combinations thereof.

Pharmaceutical compositions comprising a senolytic combination can be formulated as emulsions for topical application. An emulsion contains one liquid distributed the body of a second liquid. The emulsion may be an oil-in-water emulsion or a water-in-oil emulsion. Either or both of the oil phase and the aqueous phase may contain one or more surfactants, emulsifiers, emulsion stabilizers, buffers, and other excipients. The oil phase may contain other oily pharmaceutically approved excipients. Suitable surfactants include, but are not limited to, anionic surfactants, non-ionic surfactants, cationic surfactants, and amphoteric surfactants. Compositions for topical application may also include at least one suitable suspending agent, antioxidant, chelating agent, emollient, or humectant.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. Liquid sprays may be delivered from pressurized packs, for example, via a specially shaped closure. Oil-in-water emulsions can also be used in the compositions, patches, bandages and articles. These systems are semisolid emulsions, micro-emulsions, or foam emulsion systems.

In some embodiments, the senolytic combination can be formulated with oleaginous bases or ointments to form a semisolid composition with a desired shape. In addition to the senolytic combination, these semisolid compositions can contain dissolved and/or suspended bactericidal agents, preservatives and/or a buffer system. A petrolatum component that may be included may be any paraffin ranging in viscosity from mineral oil that incorporates isobutylene, colloidal silica, or stearate salts to paraffin waxes. Absorption bases can be used with an oleaginous system. Additives may include cholesterol, lanolin (lanolin derivatives, beeswax, fatty alcohols, wool wax alcohols, low HLB (hydrophobel-lipophobe balance) emulsifiers, and assorted ionic and non-ionic surfactants, singularly or in combination.

Controlled or sustained release transdermal or topical formulations can be achieved by the addition of time-release additives, such as polymeric structures, matrices, that are available in the art. For example, the compositions may be administered through use of hot-melt extrusion articles, such as bioadhesive hot-melt extruded film. The formulation can comprise a cross-linked polycarboxylic acid polymer formulation. A cross-linking agent may be present in an amount that provides adequate adhesion to allow the system to remain attached to target epithelial or endothelial cell surfaces for a sufficient time to allow the desired release of the compound.

An insert, transdermal patch, bandage or article can comprise a mixture or coating of polymers that provide release of the active agents at a constant rate over a prolonged period of time. In some embodiments, the article, transdermal patch or insert comprises water-soluble pore forming agents, such as polyethylene glycol (PEG) that can be mixed with water insoluble polymers to increase the durability of the insert and to prolong the release of the active ingredients.

Transdermal devices (inserts, patches, bandages) may also comprise a water insoluble polymer. Rate controlling polymers may be useful for administration to sites where pH change can be used to effect release. These rate controlling polymers can be applied using a continuous coating film during the process of spraying and drying with the active compound. In one embodiment, the coating formulation is used to coat pellets comprising the active ingredients that are compressed to form a solid, biodegradable insert.

A polymer formulation can also be utilized to provide controlled or sustained release. Bioadhesive polymers described in the art may be used. By way of example, a sustained-release gel and the combination (or each agent of the combination) may be incorporated in a polymeric matrix, such as a hydrophobic polymer matrix. Examples of a polymeric matrix include a microparticle. The microparticles can be microspheres, and the core may be of a different material than the polymeric shell. Alternatively, the polymer may be cast as a thin slab or film, a powder produced by grinding or other standard techniques, or a gel such as a hydrogel. The polymer can also be in the form of a coating or part of a bandage, stent, catheter, vascular graft, or other device to facilitate delivery of the senolytic combination. The matrices can be formed by solvent evaporation, spray drying, solvent extraction and other methods known to those skilled in the art.

In certain embodiments of a method described herein for treating a cardiovascular disease associated with or caused by arteriosclerosis, a senolytic combination may be delivered directly into a blood vessel (e.g., an artery) via a stent. In a particular embodiment, a stent is used for delivering a senolytic combination to an atherosclerotic blood vessel (an artery). A stent is typically a tubular metallic device, which has thin-metal screen-like scaffold, and which is inserted in a compressed form and then expanded at the target site. Stents are intended to provide long-term support for the expanded vessel. Several methods are described in the art for preparing drug-coated and drug-embedded stents. For example, a senolytic combination may be incorporated into polymeric layers applied to a stent. A single type of polymer may be used, and one or more layers of the senolytic combination permeated polymer may be applied to a bare metal stent to form the senolytic combination-coated stent. The senolytic combination may also be incorporated into pores in the metal stent itself, which may also be referred to herein as a senolytic combination-permeated stent or senolytic combination-embedded stent. In certain particular embodiments, a senolytic combination may be formulated within liposomes and applied to a stent. Placement of stents in an atherosclerotic artery is performed by a person skilled in the medical art.

In one particular embodiment, the senolytic combination administered to a subject who has an ophthalmic senescence associated or disease or disorder may be delivered intraocularly or intravitreally. In other specific embodiments, a senolytic combination may be administered to the eye by a conjunctival route, applying the senolytic combination to the mucous membrane and tissues of the eye lid, either upper, lower, or both. Any of these administrations may be bolus infusions. In other particular embodiments, a pharmaceutical composition comprising a senolytic combination described herein may be formulated for sustained or slow release (which may also be called timed release or controlled release), which formulations are described in greater detail herein. In certain embodiments, methods are provided herein for treating or preventing (i.e., reducing the likelihood of occurrence of; delaying the onset or development of, or inhibiting, retarding, slowing, or impeding progression or severity of) an ocular disease, disorder, or condition (e.g., cataracts, macular degeneration); and for selectively killing senescent cells in an eye of a subject in need thereof by administering a senolytic combination (which may be combined with at least one pharmaceutically acceptable excipient to form a pharmaceutical composition) directly to an eye.

Kits with unit doses of one or more of the agents described herein, usually in oral or injectable doses, are provided. Such kits may include a container containing the unit dose, an informational package insert describing the use and attendant benefits of the drugs in treating the senescent cell associated disease, and optionally an appliance or device for delivery of the composition.

EXAMPLES

Example 1

Identification of Senescence Associated Pathways

Protcomic analyses by nano LC MS/MS were performed on lysates on human abdominal subcutaneous preadipocytes that were senescent or non-senescent. Preadipocytes, one of the most abundant cell types in humans susceptible to senescence, were extracted from fat tissues of nine different healthy kidney transplant donors by collagenase digestion. Prior consent from the donors was obtained. Senescence was induced by 10 Gy radiation or by serial subculturing. Bioinformatics methods were used to identify pathways that were susceptible to existing drugs and that could mediate cell death.

Senescence-associated β-galactosidase (SA-β gal) activity was used to assess the percentage of senescent cells present in the irradiated cell cultures. To be considered a senescent culture, 75% or more of the cells needed to demonstrate SA-β gal activity. Both whole cell lysates and cellular supernatants were collected. Proteins were separated on 1D SDS-PAGE. Sections of the gels were destained, reduced, alkylated, and trypsin-digested. Extracted peptides were analyzed by nano-LC-MS/MS on a THERMO SCIENTIFIC™ Q Exactive mass spectrometer. LC Progenesis software (Nonlinear Dynamics, UK) was used to identify and quantify proteins. The data were then submitted to Ingenuity, Metacore, Cytoscape, and other software for pathway and protein network analysis. Among the pathways identified during senescence were those involved in cell survival signaling and inflammatory pathways. These pathways include at least PI3K/AKT, Src kinase signaling, insulin/IGF-1 signaling, p38/MAPK, NF-KB signaling, TGFβ signaling, and mTOR/protein translation (see FIGS. 2A-2D).

FIG. 1 shows a confirmatory Western immunoblot of proteins involved in these and related pathways at various times (24 hr, 3, 6, 8, 11, 15, 20, and 25 days) after radiation. Phosphorylated polypeptides in the senescent cell samples were detecting using horse-radish peroxidase labeled antibodies (Cell Signaling Technology, Danvers, Mass.) specific for the polypeptides indicated in FIG. 1. Senescence is fully established at day 25 to 30 in these cells.

Approximately 20 compounds were screened for killing senescent human cultured preadipocytes and were detected by phase-contrast microscopy. Dasatinib, enzastaurin, and quercetin were included in the 20 compounds and were chosen for further study. Dasatinib inhibits at least Src kinase activity; quercetin is described in the art as inhibiting Src kinase, histone deacetylase (HDAC), Akt kinase, p38 MAPK, and ROS (reactive oxygen species); and enzastaurin inhibits at least protein kinase C-beta. FIGS. 2A-2D illustrate pathways affected by the agents described herein. FIG. 2A shows possible target proteins affected by quercetin altering a cell survival pathway. Without wishing to be bound by theory, the components shown are likely indirectly affected (indicated by non-solid lines) when quercetin alters either a cell survival signaling pathway or an inflammatory pathway. Downstream components of the Src kinase pathway, the PI3K pathway, and the Akt pathway are illustrated in FIGS. 2B-2D, respectively. A solid arrow between two components indicates that the component at the source of the solid line has a direct role in upregulating the component to which the arrow is pointing. Included in FIG. 2C is LY284992, which is a potent selective phosphatidylinositol 3-kinase (PI3K) inhibitor.

Example 2

Selective Killing of Senescent Fibroblasts

Figure 3:
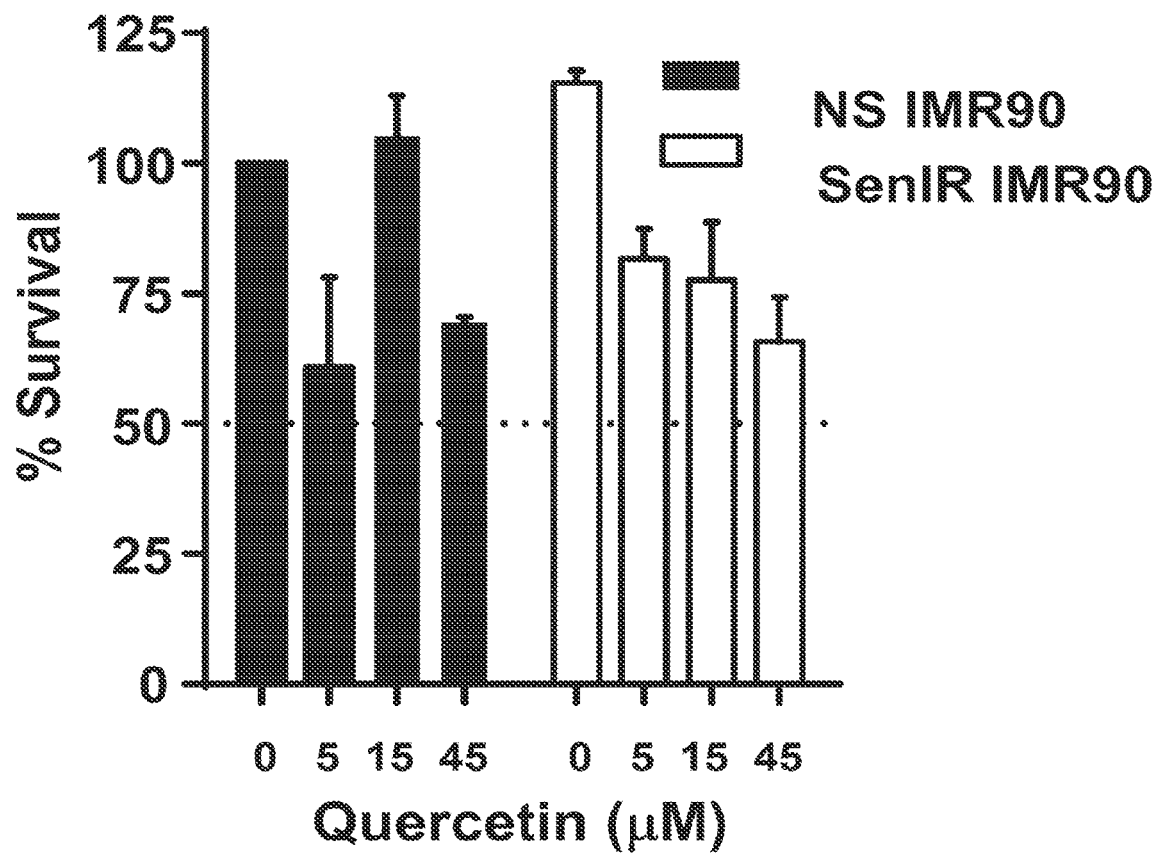
FIG. 3 depicts the percent survival of irradiated IMR90 fibroblast cells after exposure to quercetin. Senescence of IMR90 cells was induced by exposure to radiation. Survival of senescent IMR90 cells (SenIR IMR90, white bars) and non-senescent IMR90 cells (NS IMR90, black bars) is shown after treatment with quercetin.

Senescence of human primary lung fibroblasts (IMR90) (IMR-90 (ATCC® CCL-186TH, Mannassas, Va.) was induced by irradiation. IMR90 cells in culture were subjected to 10 Gy radiation (Day-7). Four days after irradiation (Day-3), the culture media was changed. Three days after the media change (Day 0), the cells were exposed to media containing quercetin. Non-irradiated IMR90 cells were included as controls. Non-irradiated and irradiated IMR90 cells were exposed to quercetin at concentrations of 5, 10, 15, and 45 µM. Percent survival was determined four days after exposure to the drugs (Day 4). The number of viable cells was determined by using ATPLITE (Perkin-Elmer, Waltham, Mass.). The results are presented in FIG. 3.

Figure 4A:
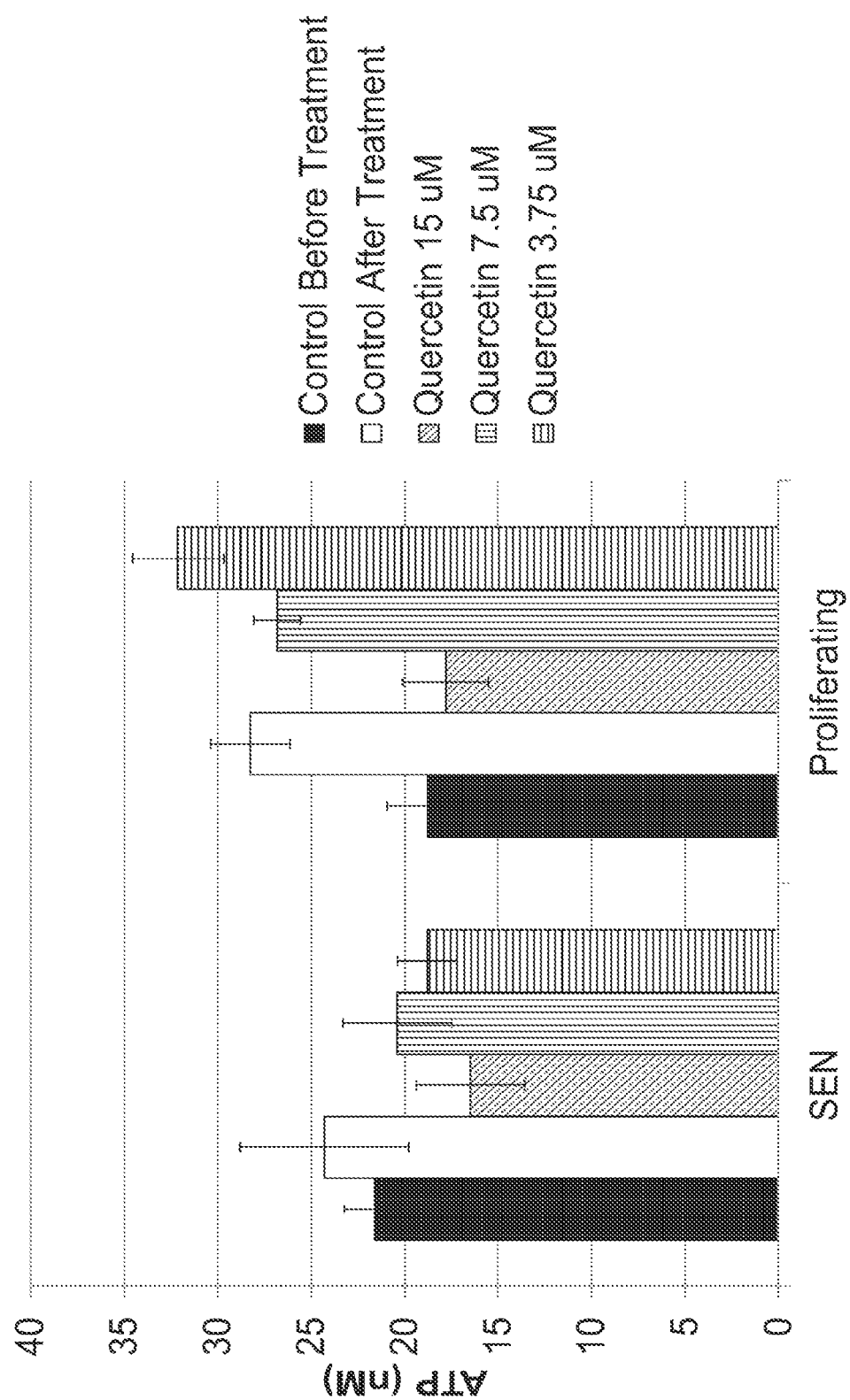
FIGS. 4A-4F illustrates the effect on senescent (SEN) and proliferating endothelial cells (HUVEC) by exposure to quercetin, dasatinib, and dasatinib+quercetin. The HUVEC cells were exposed to radiation to induce senescence. The data are presented as mean viability (ATP ($\mu$M))+SEM of 4.
Figure 4B:
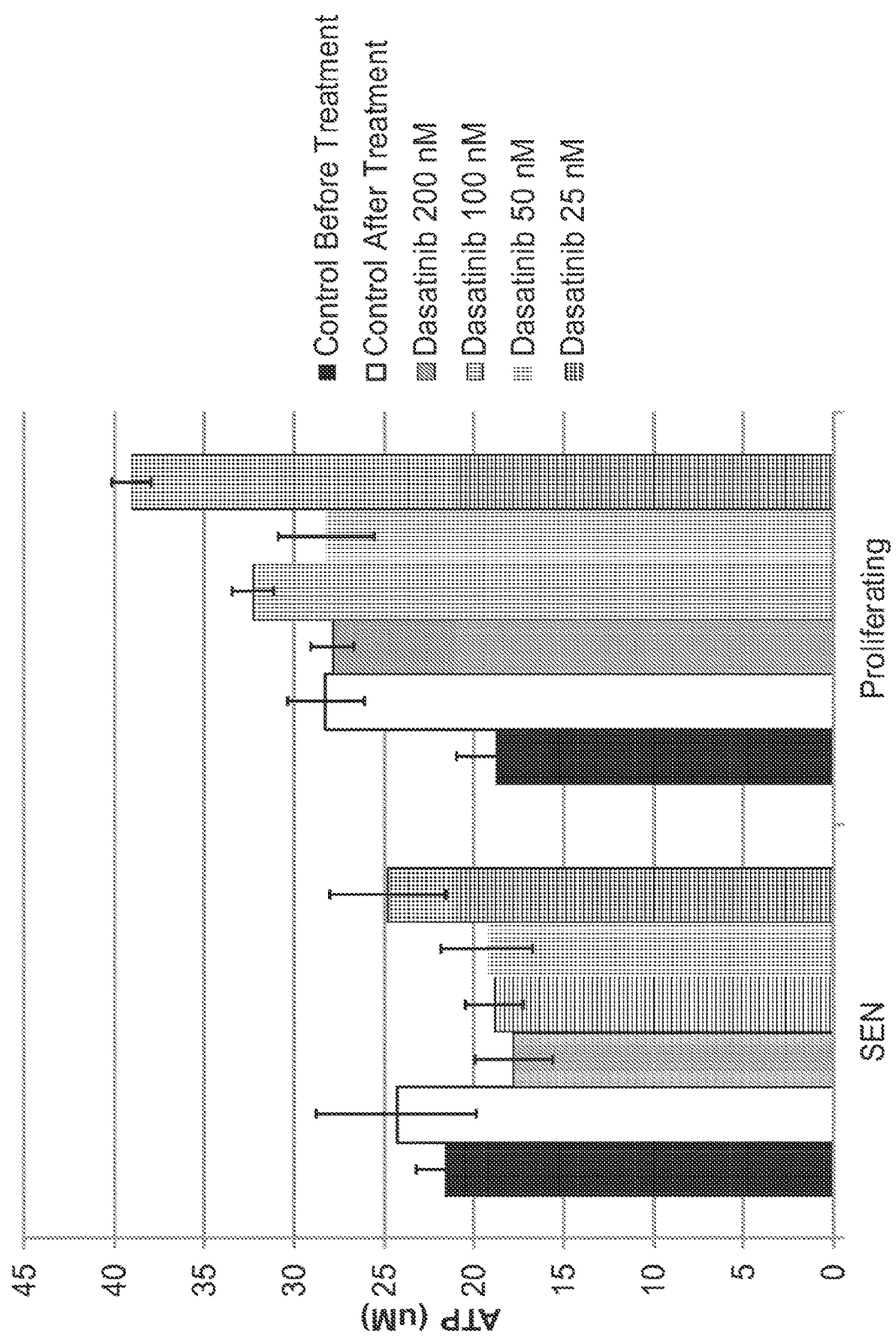
Figure 4C:
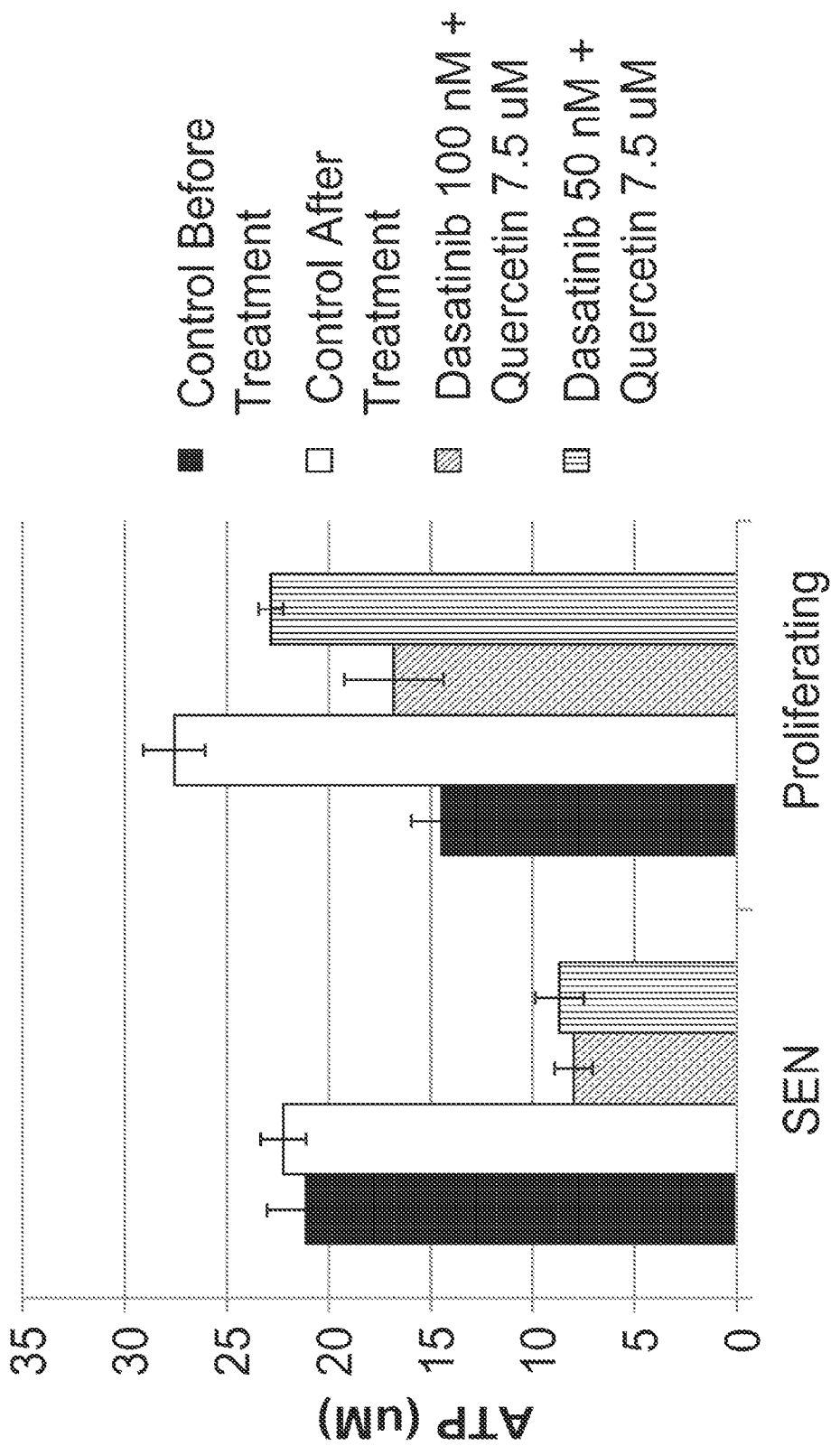
Figure 4D:
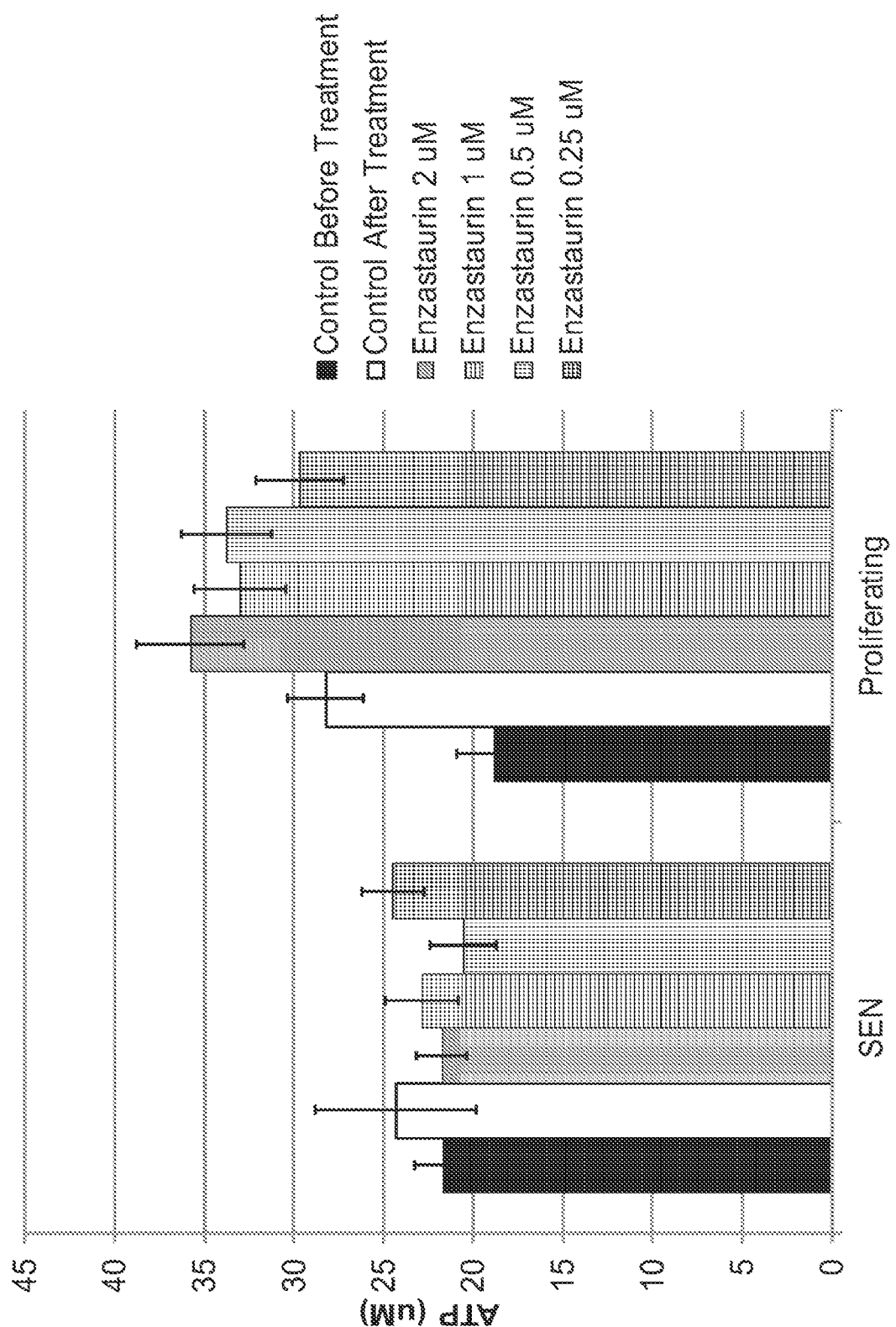
Figure 4E:
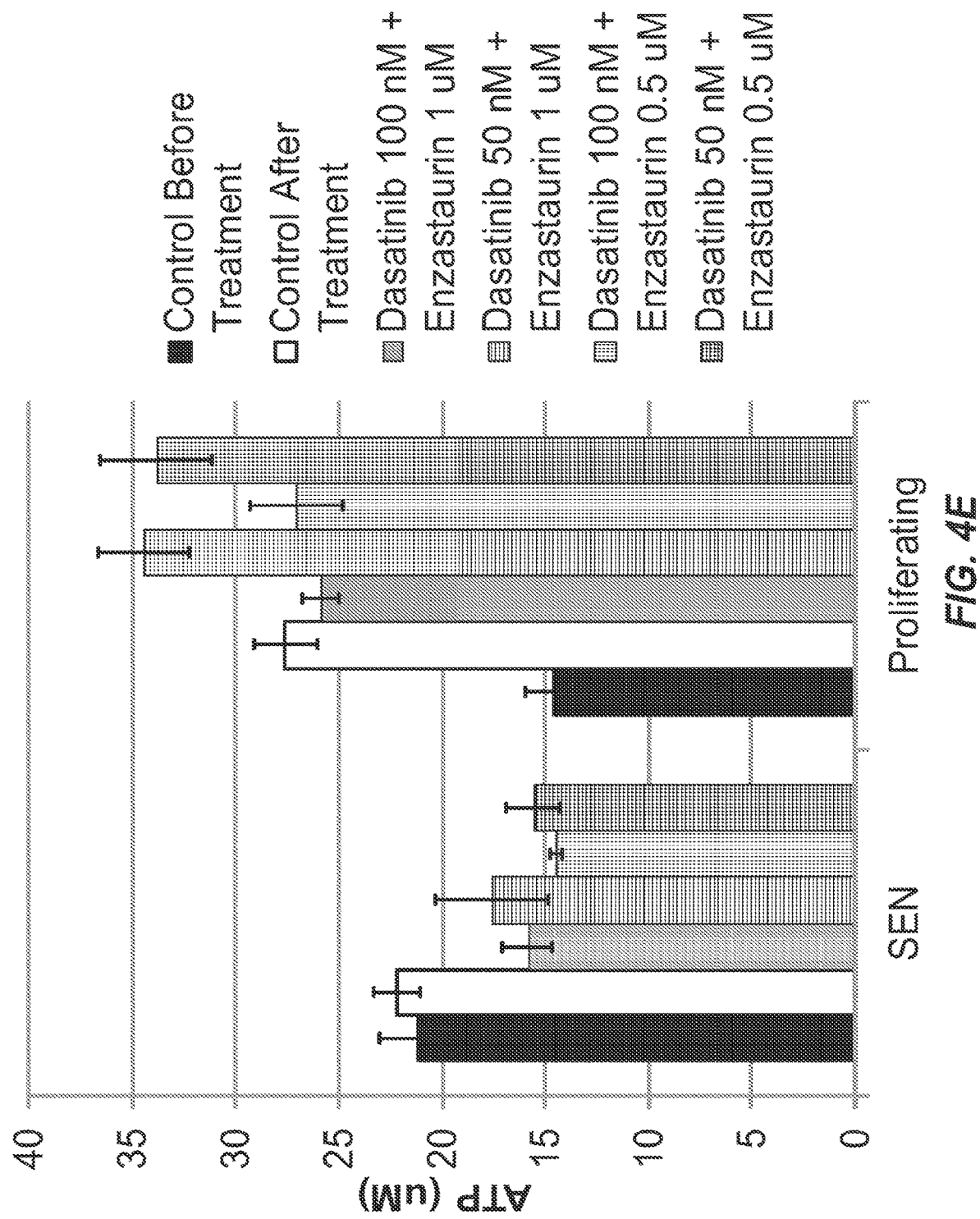
Figure 4F:
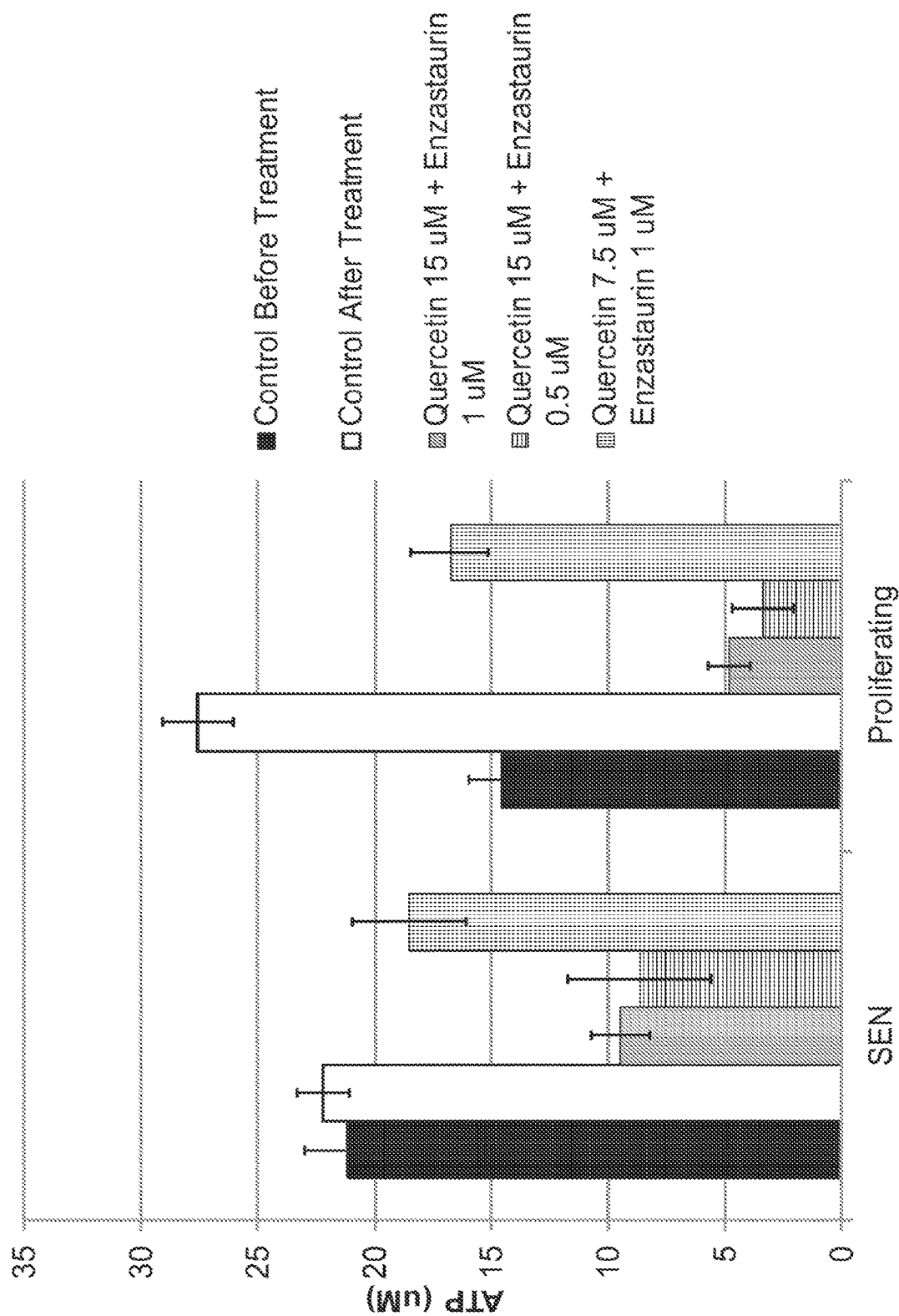

In a separate experiment, IMR90 cells were irradiated as described above to induce senescence. Approximately 20 days after irradiation, the senescent cells and proliferating IMR90 cells were exposed to enzastaurin at concentrations of 0.25 0.5 and 2 µM. Enzastaurin at these concentrations did not selectively kill the senescent cells and did not kill the proliferating cells. Enzastaurin may have a slight potentiating effect of dasatinib (see FIG. 4E). Enzastaurin in combination with quercetin killed senescent cells but also killed the non-senescent proliferating cells (see FIG. 4F).

Imatinib and sorafenib were also tested for the capability to selectively kill senescent cells. Some senolytic effect was observed with imatinib at 50 which is not considered to be a physiologically acceptable concentration of this drug. Microscopic examination of senescent cells and non-senescent cells treated with sorafenib suggested that both senescent cells and non-senescent cells were killed.

Example 3

Selective Killing of Senescent Endothelial Cells

Human umbilical endothelial cells (HUVEC) (Lonza Group, Basel, Switzerland) were induced to senescence by exposure to 10 Gy radiation. Twenty days after irradiation, markers of cellular senescence (SA-β Gal) and growth arrest, determined by incorporation of BR dU, were evident. Non-senescent HUVEC cells used as control were plated at low density in culture media so that the cells were proliferating when exposed to the test drug. Senescent HUVEC cells and non-senescent, proliferating HUVEC cells were treated for 48 hours with quercetin, dasatinib, and enzastaurin as follows: (1) quercetin alone at 3.75, 7.5 and 15µ,M; (2) dasatinib alone at 25, 50, 100, and 200 nM; (3) enzastaurin alone at concentrations of 0.25 0.5 1 and 2 µM; (4) dasatinib at 100 nM plus quercetin at 7.5 µM; (5) with dasatinib at 50 nM plus quercetin at 7.5 µM; (6) dasatinib at 100 nM plus enzastaurin at 1.0 µM; (7) dasatinib at 100 nM plus enzastaurin at 0.5 µM; (8) dasatinib at 50 nM plus enzastaurin at 1.0 µM; (9) dasatinib at 50 nM plus enzastaurin at 0.5 µM; (10) quercetin at 15 µM and enzastaurin at 1.0 µM; (11) quercetin at 15 µM and enzastaurin at 1.0 µM; and (12) quercetin at 7.5 µM and enzastaurin at 1.0 µM. The number of viable cells was determined by ATPLITE (Perkin-Elmer, Waltham, Mass.). The data are presented in FIGS. 4A-4F as mean viability (ATP (µM))+SEM of 4.

Example 4

Selective Killing of Senescent Preadipocyte Cells

Figure 5A:
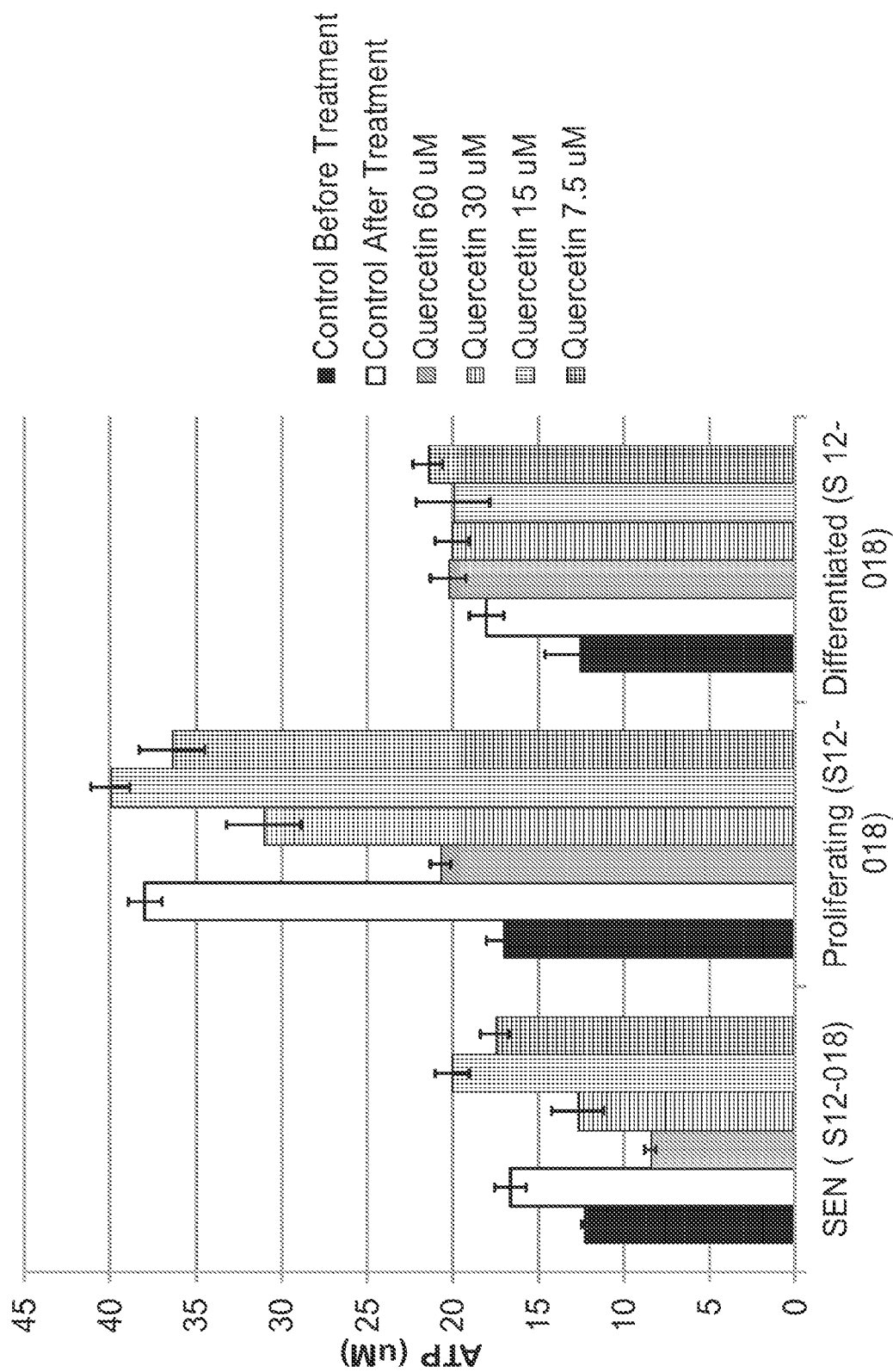
FIGS. 5A-5F illustrates the effect on senescent, proliferating, or differentiated preadipocytes cells by exposure to quercetin, dasatinib, dasatinib+quercetin, enzastaurin, enzastaurin+dasatinib, and enzastaurin+quercetin. Human primary abdominal subcutaneous preadipocytes were obtained with consent from donors. The preadipocytes (sample S12-018) were exposed to radiation to induce senescence. The data are presented as mean viability (ATP ($\mu$M))+SEM of 4.
Figure 5B:
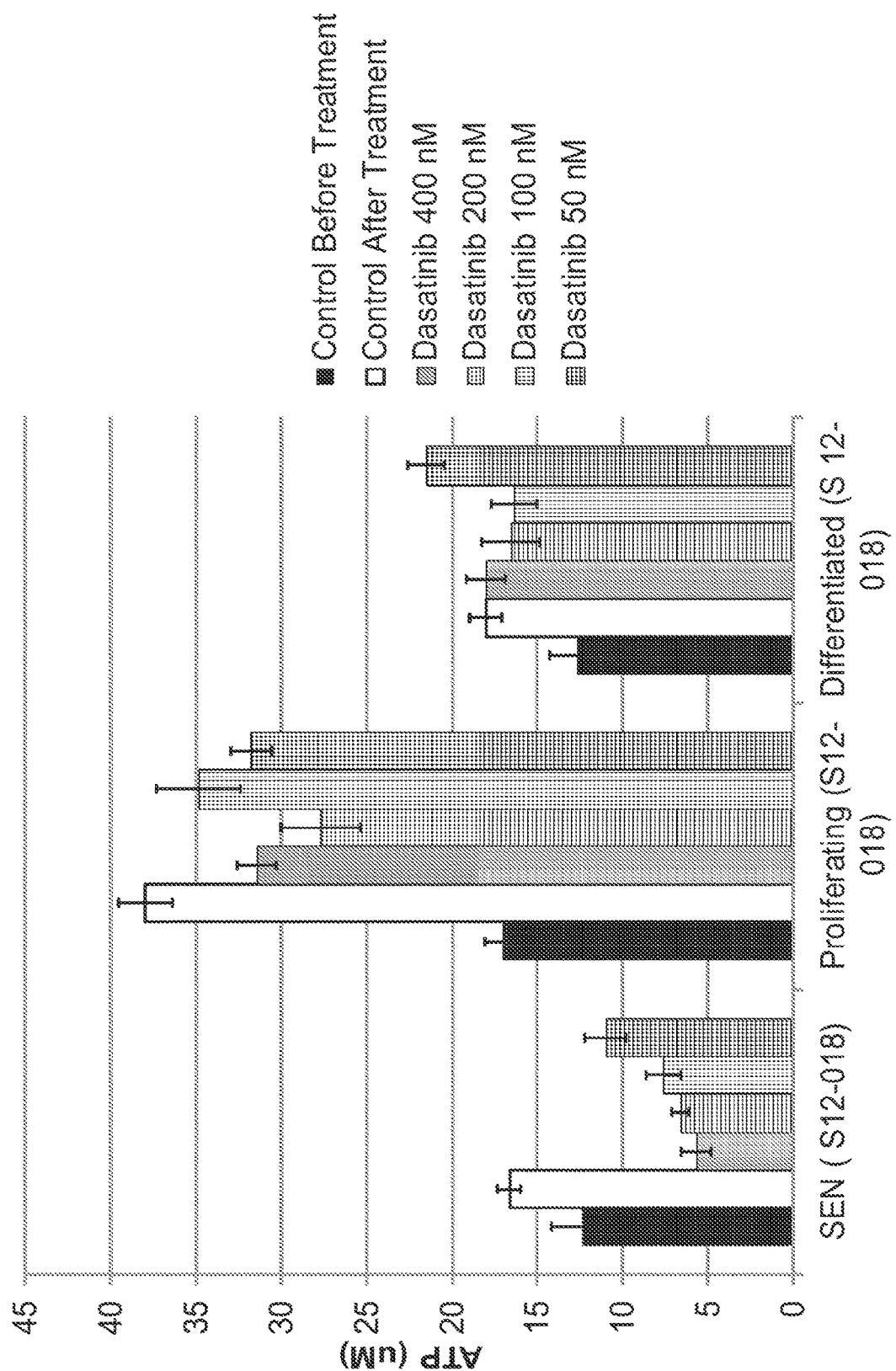
Figure 5C:
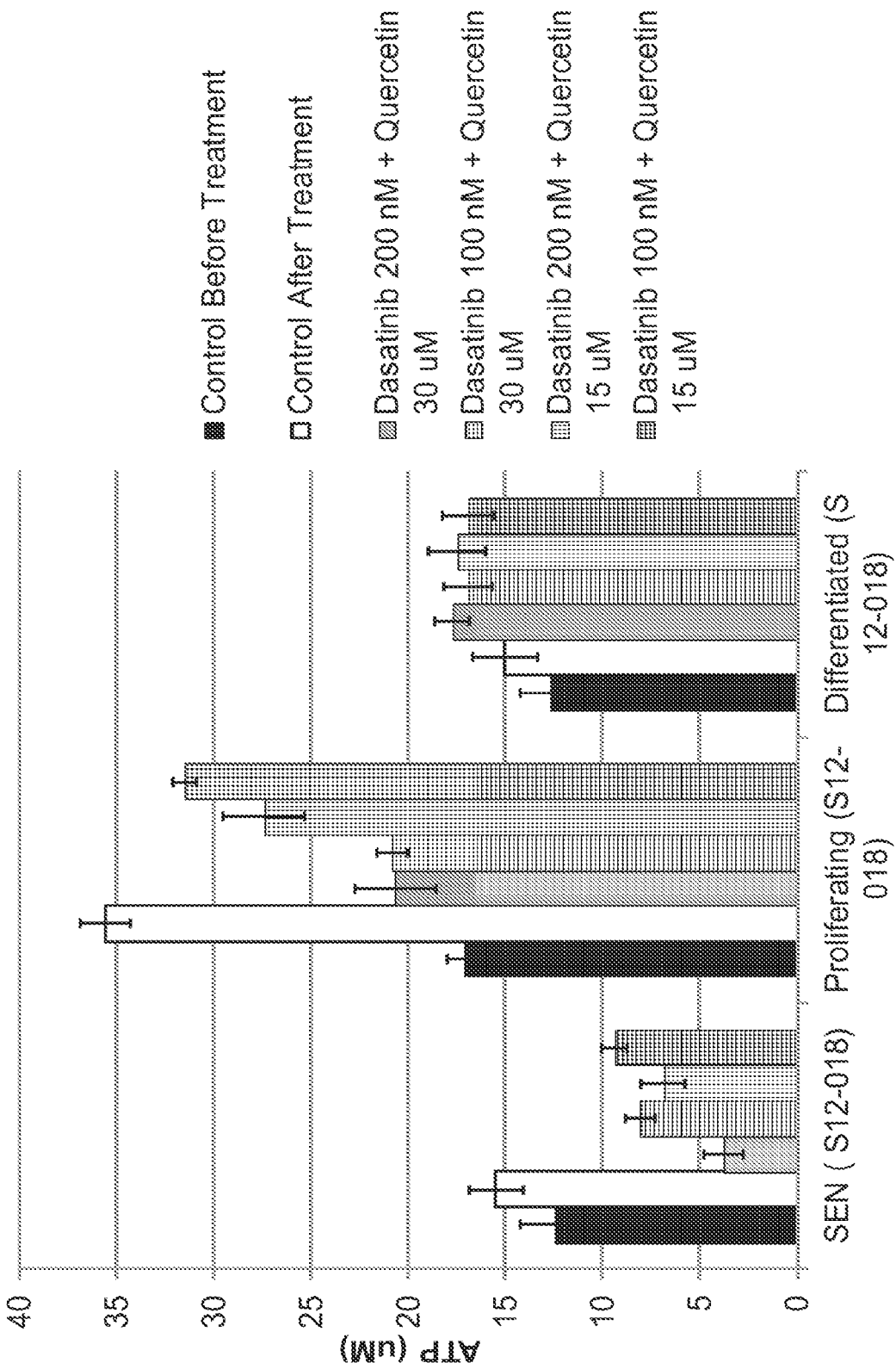
Figure 5D:
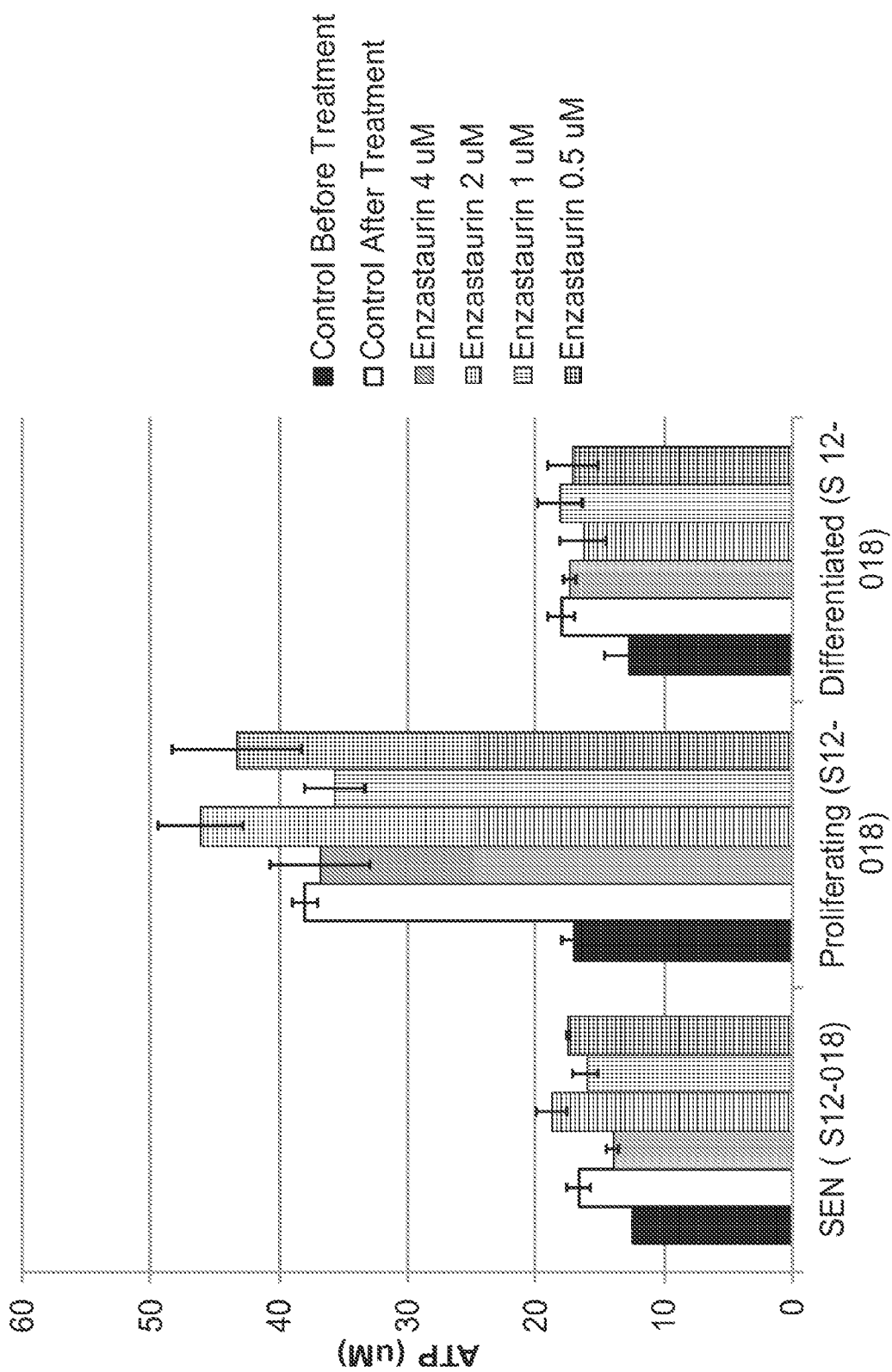
Figure 5E:
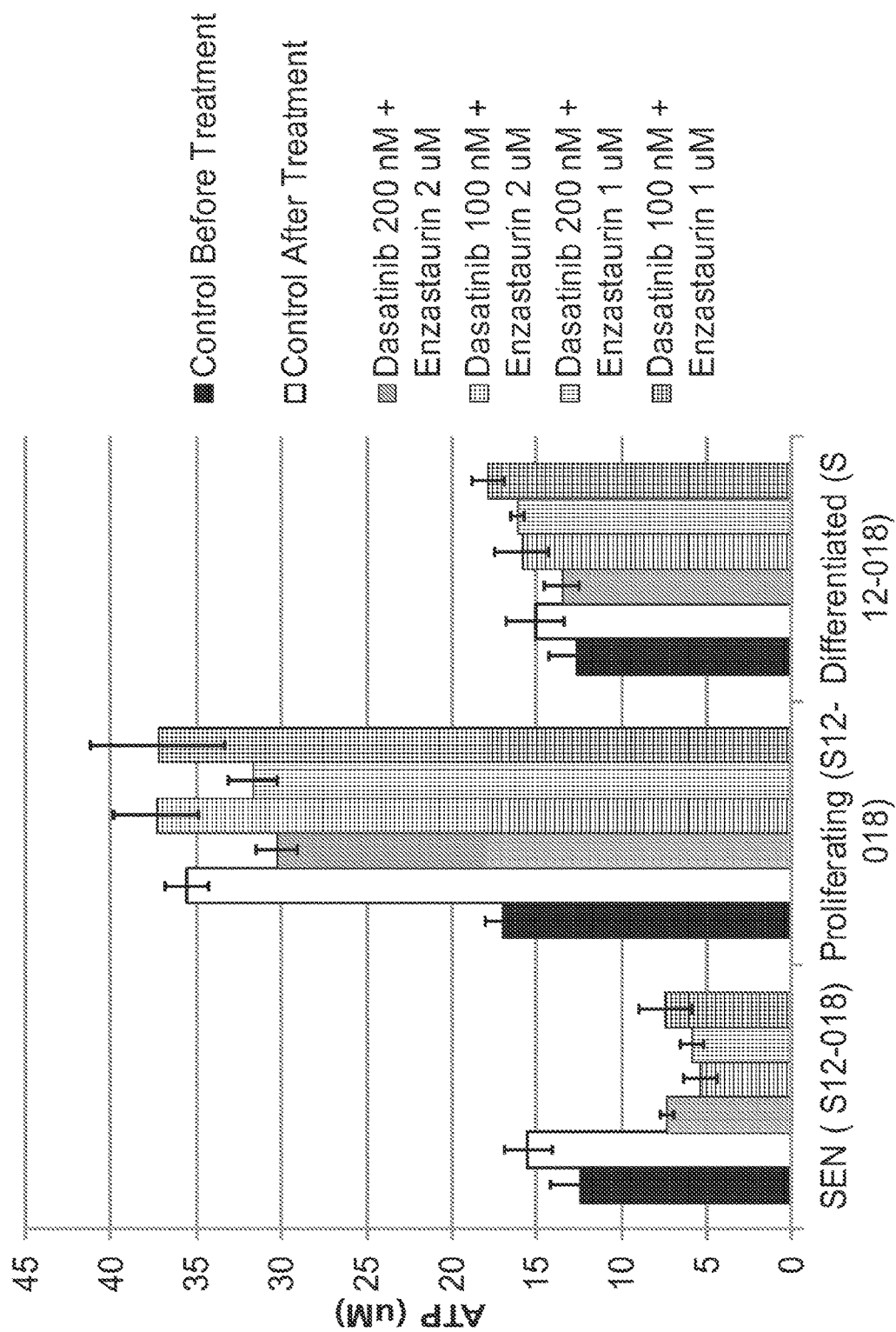
Figure 5F:
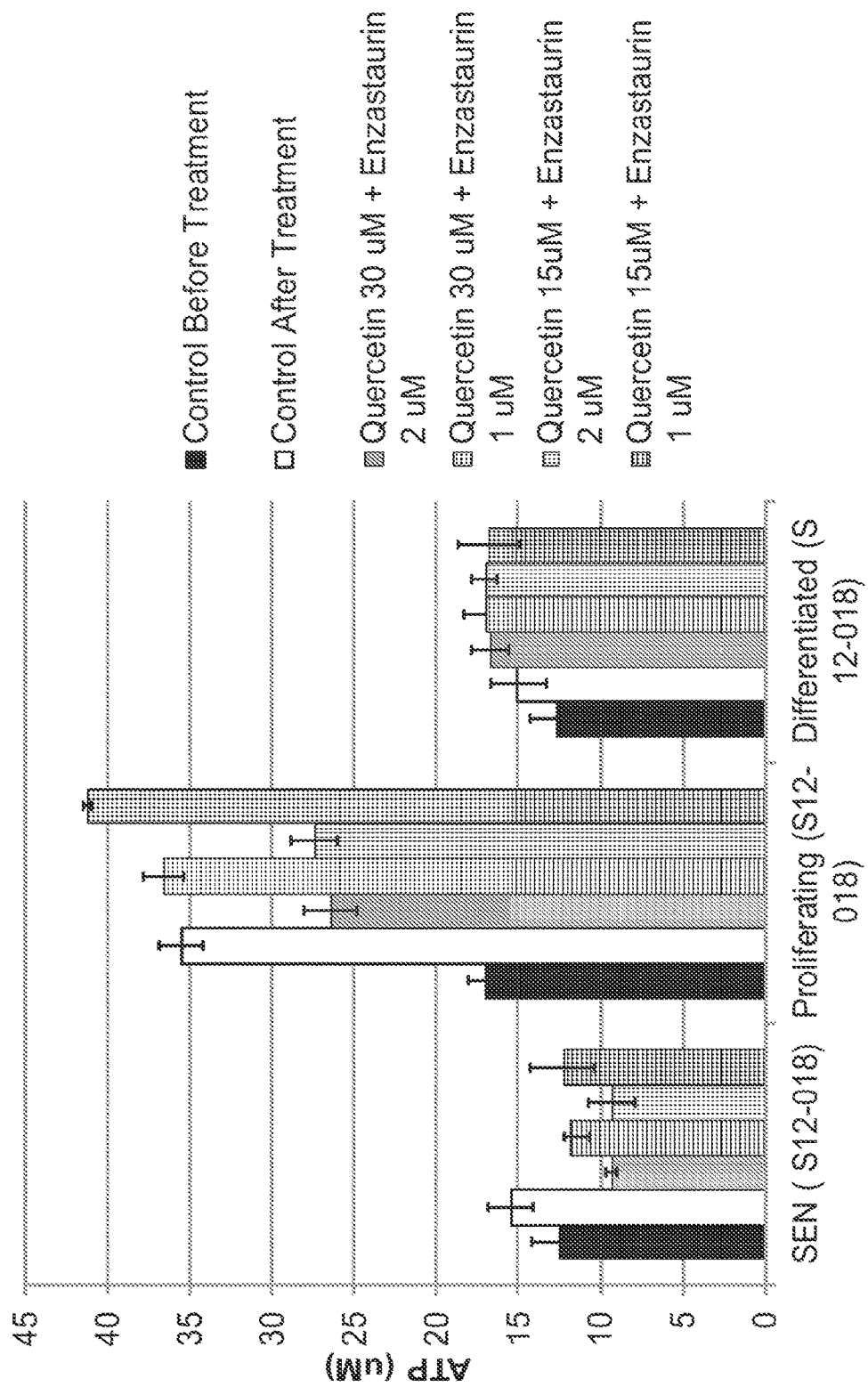

Human primary abdominal subcutaneous preadipocytes were obtained with consent from donors. The preadipocytes were exposed to radiation and senescence determined as described in Example 3. After 20 days in culture, senescent preadipocytes and control proliferating preadipocytes and control differentiated preadipocytes from the same donor were treated for 48 hours with quercetin at 7.5, 15, 30, and 60 µM; with dasatinib at 50, 100, 200 nM, and 400 nM; with enzastaurin at 0.25 µM, 0.5 µM, and 2 µM; with dasatinib at 100 nM plus quercetin at 15 and 30 µM; with dasatinib at 200 nM plus quercetin at 15 and 30 µM; with dasatinib at 200 nM plus enzastaurin at 1 µM and 2 µM; with dasatinib at 100 nM plus enzastaurin at 1 µM and 2 µM; with quercetin at 30 µM plus enzastaurin at 1 µM and 2 µM; and with quercetin at 15 µM plus enzastaurin at 1 µM and 2 µM. The number of viable cells was determined by ATPLITE (Perkin-Elmer, Waltham, Mass.). The data are presented in FIGS. 5A-5F as mean viability (ATP (NI))+SEM of 4. The combination of dasatinib and quercetin exhibited selective killing of senescent cells. An effective combination included dasatinib at 200 nM and quercetin at 30 µM (see FIG. 5C).

Example 5

Removal of Senescent Cells In Vivo by Dasatinib and Quercetin

The capability of dasatinib alone, quercetin alone, and the combination of dasatinib and quercetin to remove senescent cells in vivo was determined in transgenic p16-3MR mice (see International Application Publication No. WO 2013/090645). The transgenic mouse comprises a p16$^{ink4a}$ promoter (see, e.g., operatively linked to a trimodal fusion protein for detecting senescent cells and for selective clearance of senescent cells in these transgenic mice. The promoter, p16$^{inkh4a}$, which is transcriptionally active in senescent cells but not in non-senescent cells (see, e.g., Wang et al., J. Biol. Chem. 276:48655-61 (2001); Baker et al., Nature 479:232-36 (2011)), was engineered into a nucleic acid construct. The p16$^{Ink4a}$ gene promoter (approximately 100 kilobase pairs) was introduced upstream of a nucleotide sequence encoding a trimodal reporter fusion protein. Alternatively, a truncated p16ink4a promoter may be used (see, e.g., Baker et al., Nature, supra; International Application Publication No. WO/2012/177927; Wang et al., supra). The trimodal reporter protein is termed 3MR and consists of renilla luciferase (rLUC), monomeric red fluorescent protein (mRFP) and a truncated herpes simplex virus thymidine kinase (tTK) (see, e.g., Ray et al., Cancer Res. 64:1323-30 (2004)). Thus, the expression of 3MR is driven by the p16$^{ink4a}$ promoter in senescent cells only. The detectable markers, rLUC and mRFP permitted detection of senescent cells by bioluminescence and fluorescence, respectively. The expression of tTK permitted selective killing of senescent cells by exposure to the pro-drug ganciclovir (GCV), which is converted to a cytotoxic moiety by tTK. Transgenic founder animals, which have a C57B16 background, were established and bred using known procedures for introducing transgenes into animals (see, e.g., Baker et al., Nature 479:232-36 (2011)).

Figure 6:
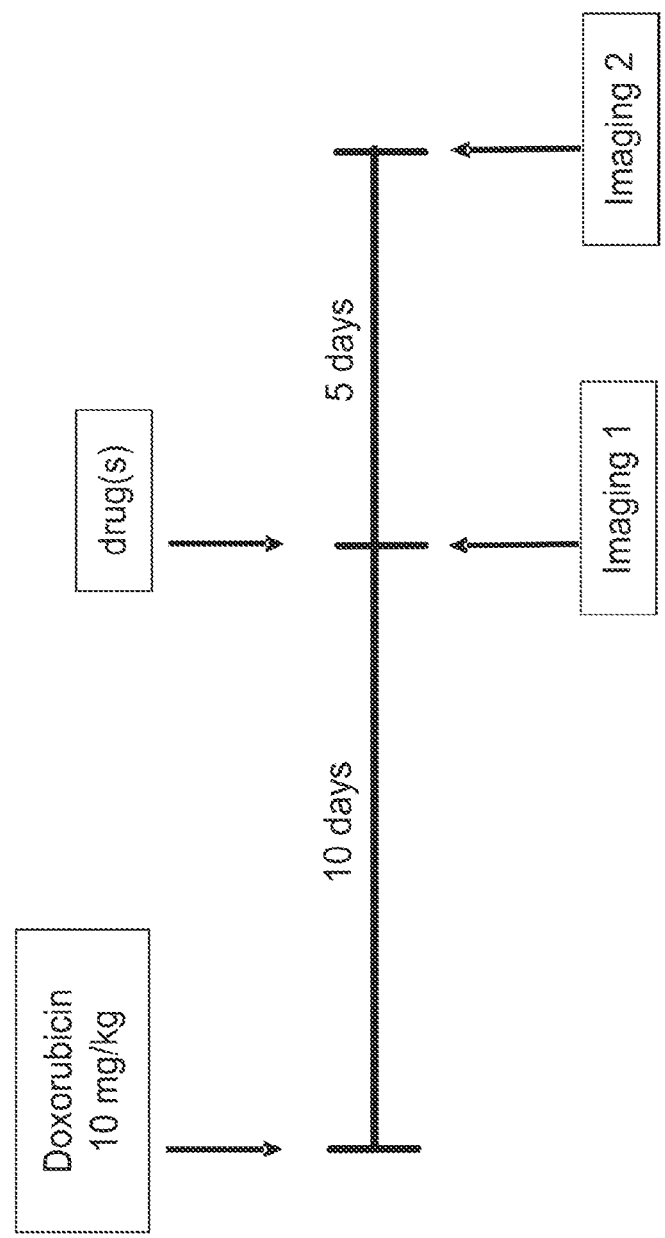
FIG. 6 presents the design of an animal study with transgenic p16-3MR mice. Senescence was induced by administering doxorubicin. Test drugs (dasatinib, quercetin, dasatinib+quercetin) and ganciclovir (control) were administered as described in Example 5 ten days after administration of doxorubicin. Luminescence imaging of the mice was performed on the day the test drugs were administered (Imaging 1) and again at 5 days after administration of the test drugs (Imaging 2).

Two-month old male and five-month old female pl 6-3MR mice were randomized into groups of nine animals per group. Senescence was induced by administering doxorubicin at 10 mg/kg to the mice ten days prior to administration of the test drug(s) (D-10). Quercetin (50 mg/kg), dasatinib (5 mg/kg), or combination of quercetin and dasatinib (50 mg/kg and 5 mg/kg, respectively) were administered once by oral gavage on Day 0. Ganciclovir (GCV) (25 mg/kg) was the positive control and was administered daily beginning at Day 0 for five days by intraperitoneal injection. Luminescence imaging was performed at Day 0 and at Day 5. A schematic of this model is presented in FIG. 6.

Figure 7A:
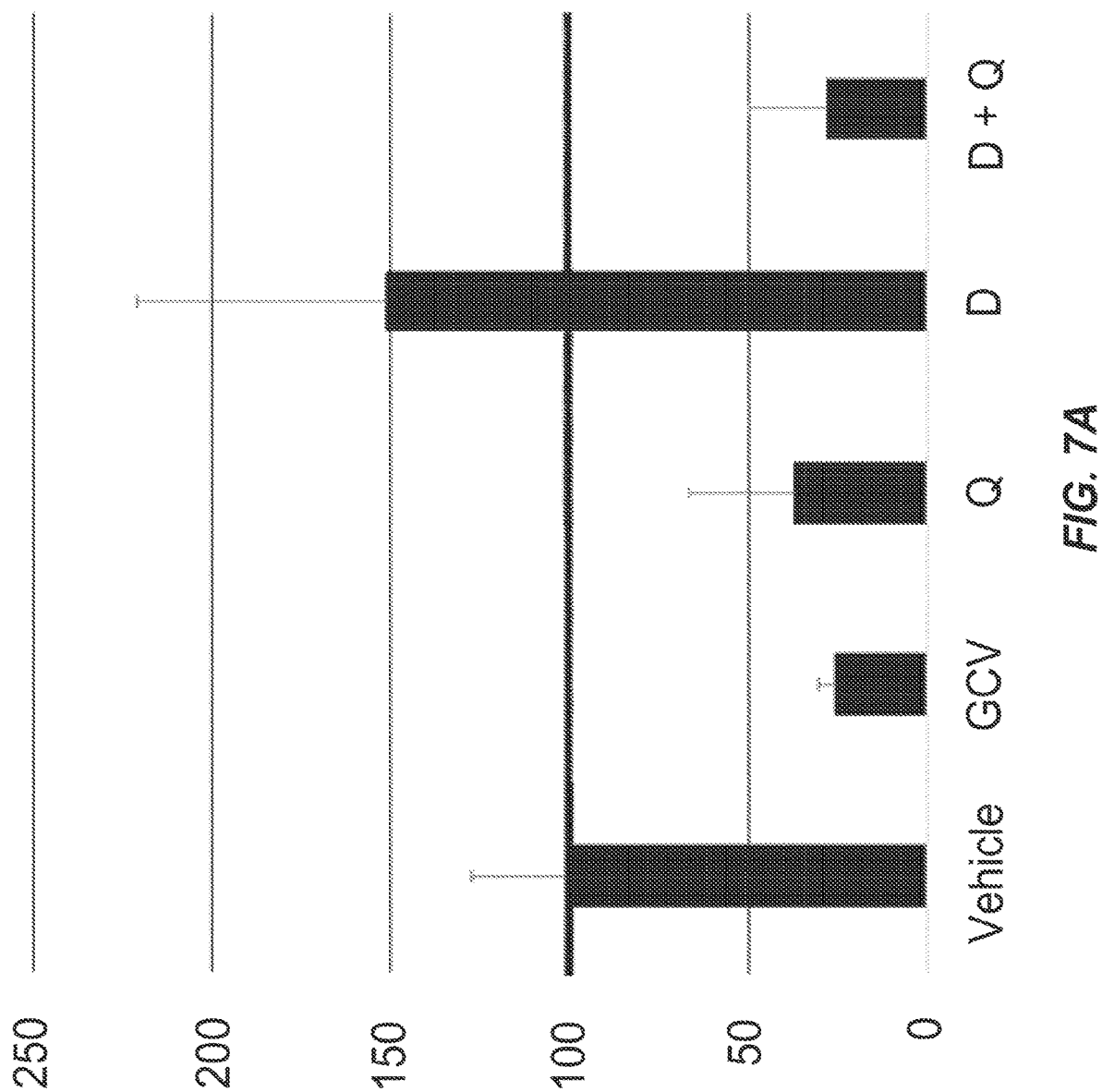
FIGS. 7A-7B present the effects in animal when treated with dasatinib or quercetin according to the design of the animal model presented in FIG. 6. Groups of transgenic p16-3MR mice (9 animals per group) received quercetin (Q), dasatinib (D), quercetin in combination (D+Q) or ganciclovir (GCV) (control) or vehicle.
Figure 7B:
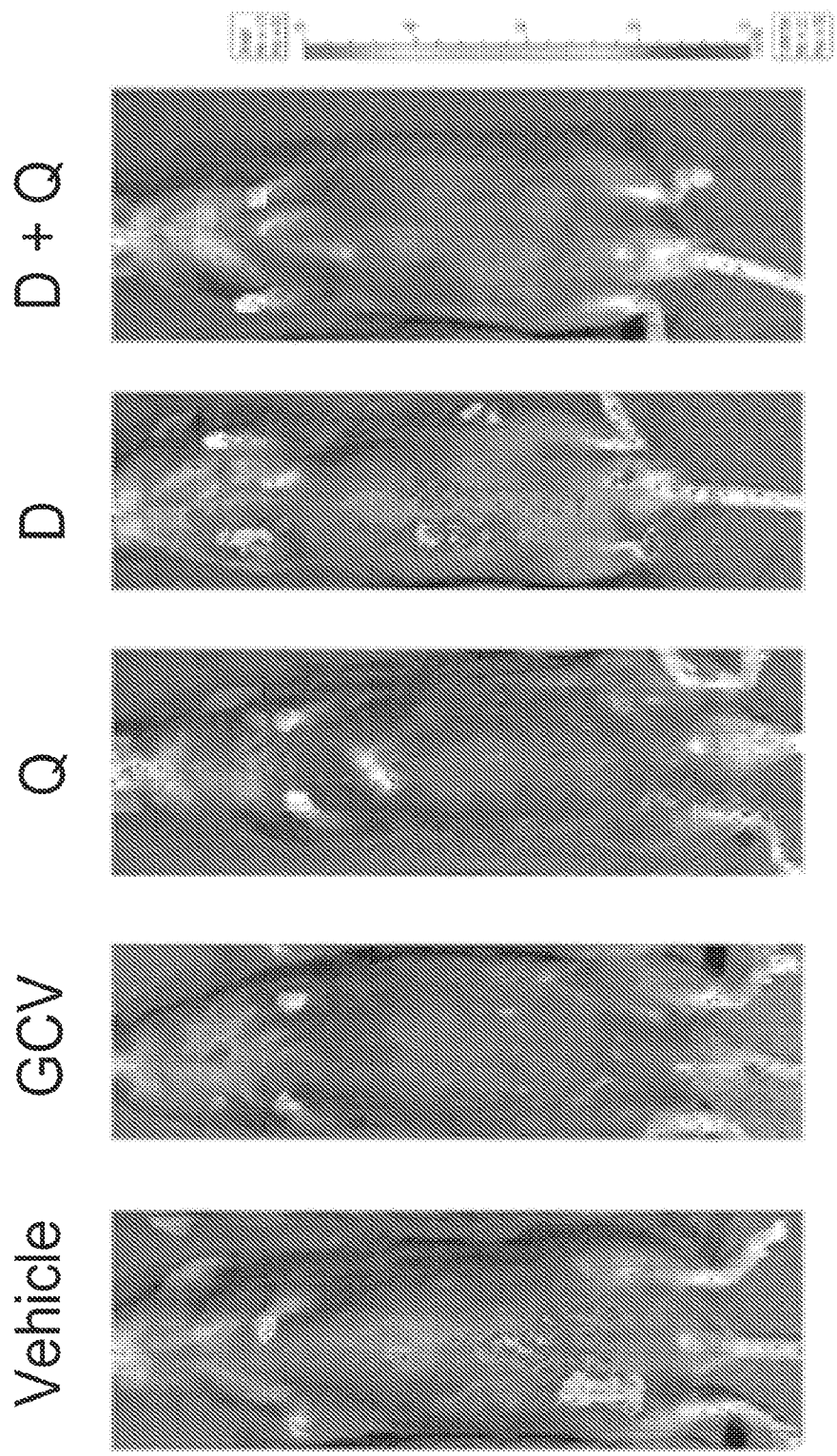

Luminescence imaging of the mice was performed on the day the test drugs were administered (Imaging 1) and again at 5 days after administration of the test drugs (Imaging 2). Reduction of luminescence (L) was calculated as: L=(Imaging 2)/(Imaging 1)%. If L≥100, no reduction in the number of senescent cells. If L<100, reduction in in the number of senescent cells. Every mouse was calculated independently, and background was subtracted from each sample. The results are presented in FIGS. 7A and 7B.

Example 6

The Effect of Dasatinib and Quercetin on Vascular Function

Figure 8:
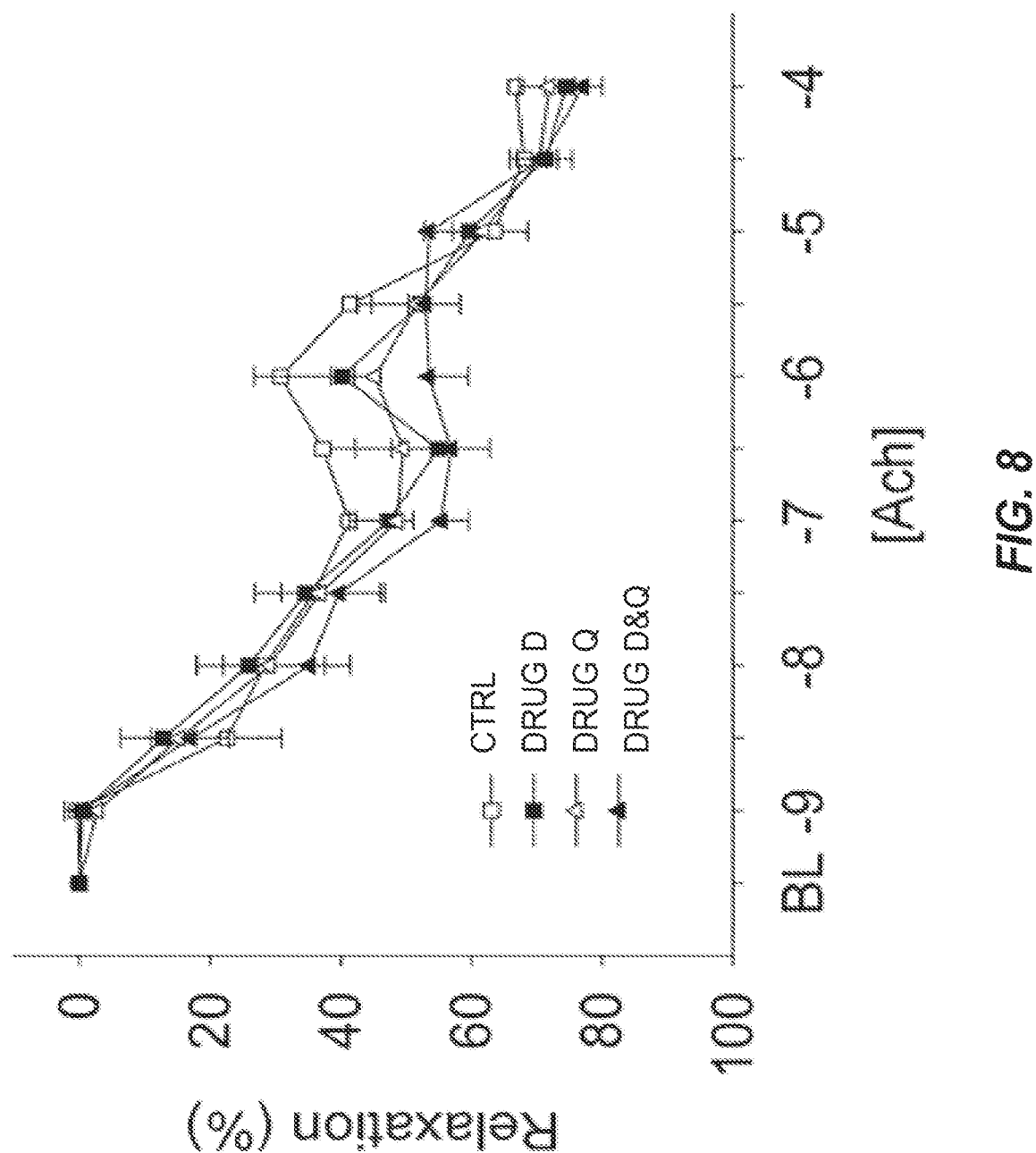
FIG. 8 presents the acetylcholine (ACH) dose response as a determination of endothelial function in the isolated aortas from 24 month old animals treated with quercetin (Drug Q); dasatinib (Drug D); or dasatinib+quercetin (Drug D+Q); or vehicle (CTRL). The concentration of ACH ranged from $10^{-9}$M to $10^{-4}$M (depicted by-9 to-4 on the x-axis). BL=baseline
Figure 9:
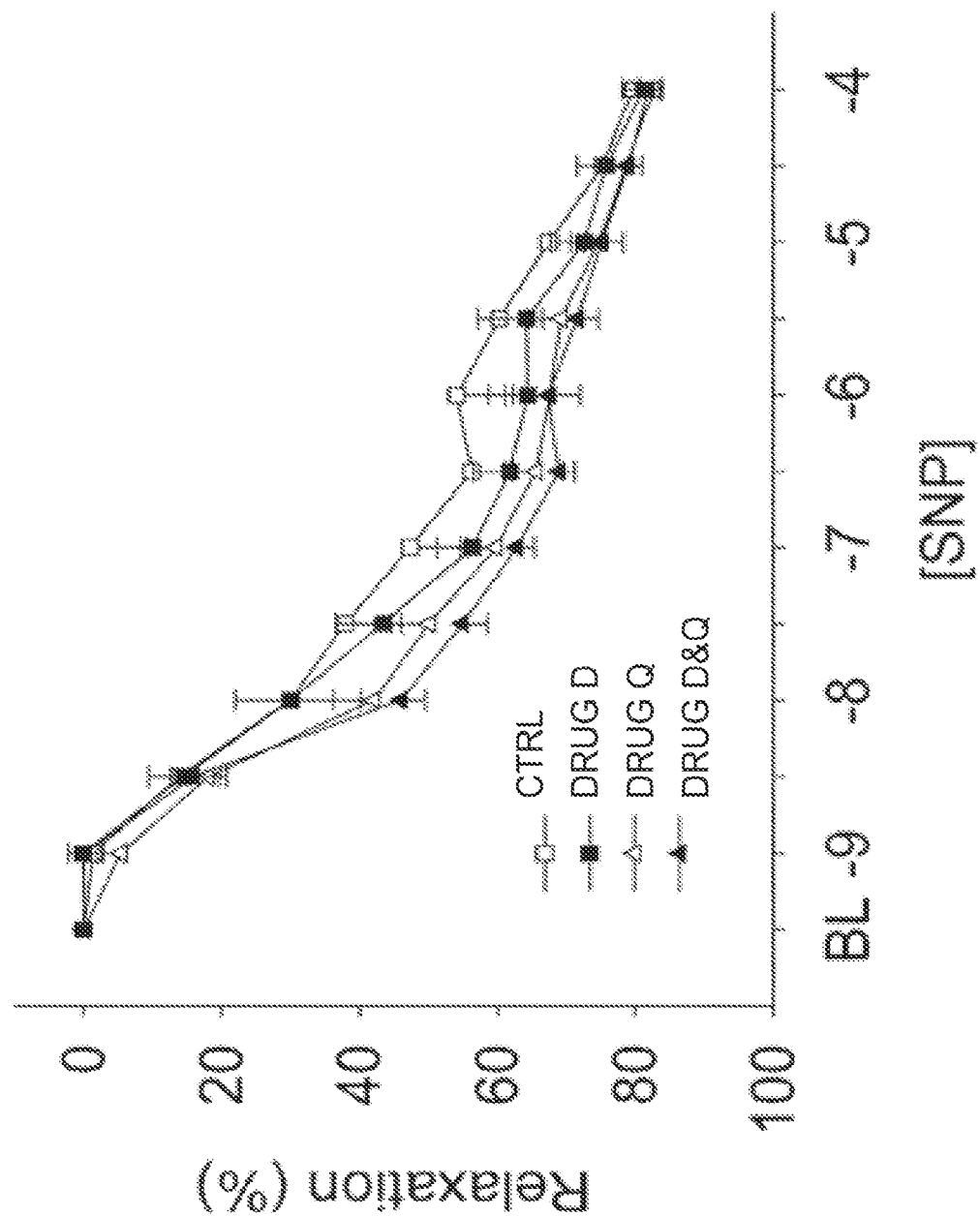
FIG. 9 presents the sodium nitroprusside (SNP) dose response as a determination of smooth muscle function in the isolated aortas from 24 month old animals treated with quercetin (Drug Q); dasatinib (Drug D); or dasatinib+quercetin (Drug D+Q); or vehicle (CTRL). The concentration of SNP ranged from $10^{-9}$M to $10^{-4}$M (depicted by-9 to-4 on the x-axis). BL=baseline

Vasomotor function of aorta was evaluated ex vivo by measurement of isometric tension (see, e.g., Roos et al., Am. J. Physiol. Heart Cir. Physiol. 305:H1428-H1439 (2013)). Twenty-four month old male mice (C57BL/6J) were used in the experiment. Groups of mice (10 animals per group) were treated with a single dose of quercetin, dasatinib, quercetin+dasatinib, or vehicle only (control). After treatment, mice were sacrificed and the aorta was excised. Connective and adipose tissue were removed from the aorta, which was then placed in oxygenated Krebs buffer. The aorta samples were suspended between two triangular hooks in an organ bath, and isometric tension was measured. Responses to acetylcholine (Ach) (endothelium dependent) and sodium nitroprusside (SNP) (endothelium independent) were examined after preconstriction of the vessel to ~50-60% of its maximal force. The concentration of ACH and SNP ranged from $10^{-9}$M to $10^{-4}$M (depicted by −9 to −4 on the x-axis of FIG. 8 and FIG. 9, respectively). The acetylcholine dose response data are shown in FIG. 8, and the nitroprusside dose response is illustrated in FIG. 9.

Example 7

Figure 10A:
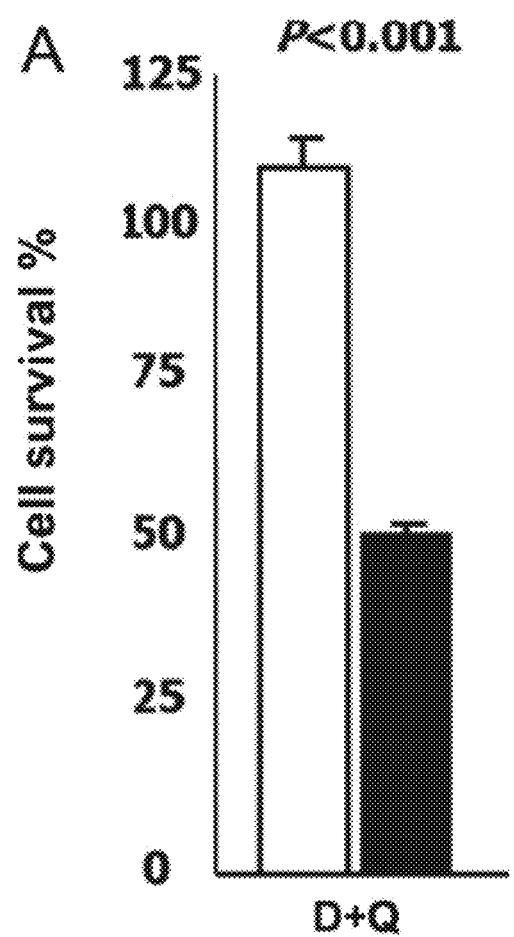
FIGS. 10A-G illustrate the effect on senescent or non-senescent preadipocytes cells by exposure to dasatinib plus quercetin or vehicle. Human primary abdominal subcutaneous preadipocytes were obtained with consent from donors. The preadipocytes from 6 subjects were pooled and exposed to radiation to induce senescence. The data are presented as mean cell survival+SEM of 6.
Figure 10B:
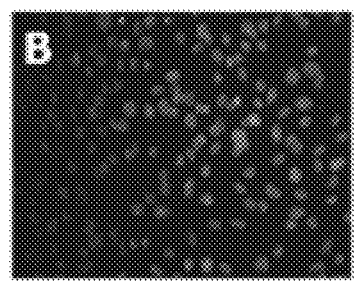
Figure 10C:
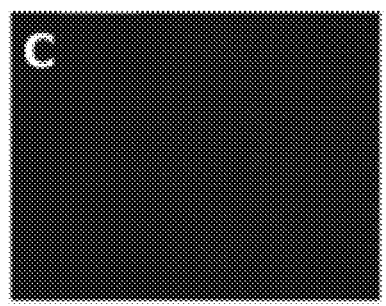
Figure 10D:
Figure 10E:
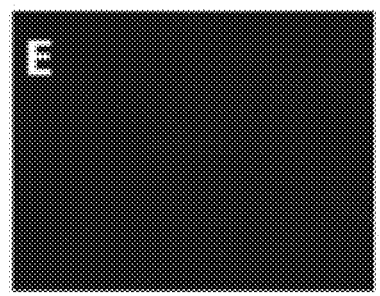
Figure 10F:
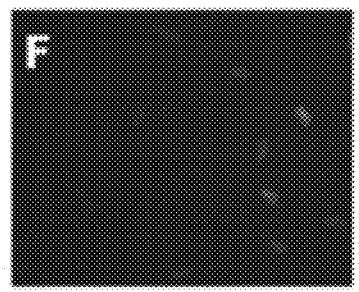
Figure 10G:
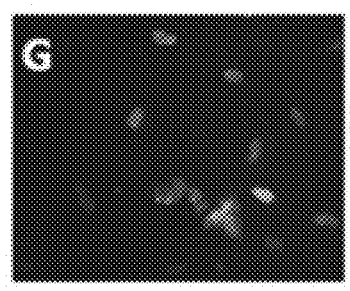

Dasatinib and Quercetin Cause Increased Apoptosis of Senescent than Non-Senescent Primary Human Preadipocytes Human primary abdominal subcutaneous preadipocytes were obtained from six subjects with consent from donors and pooled. The preadipocytes were exposed to radiation and senescence determined as described in Example 3. After 20 days in culture, senescent preadipocytes and control proliferating preadipocytes and control differentiated preadipocytes from the same donor were treated for 24 hours with dasatinib alone (200 nM), quercetin alone (30 µM), or dasatinib (200 nM) plus quercetin (30 µM). The number of viable cells was determined by ATPLITE (Perkin-Elmer, Waltham, Mass.). Experiments were performed in six replicates, and seven separate experiments were performed, which each yielded similar results for the dasatinib plus quercetin treated senescent cells. A two-tailed t-test was used to evaluate the loss of treated senescent cells relative to the loss of control cells. The combination of dasatinib plus quercetin treatment resulted in ~50% fewer senescent cells after 3 days than were plated (solid bar), while numbers of proliferating control cells increased slightly (open bar) as shown in FIG. 10A.

In a second experiment, the human primary abdominal subcutaneous preadipocytes were exposed to radiation and senescence determined as described in Example 3. After 20 days in culture, senescent preadipocytes and control non-senescent preadipocytes from the same donor were treated for 24 hours with dasatinib (200 nM) plus quercetin (30 Senescent cells were exposed to vehicle were a control. Preadipocytes were counterstained with DAPI for nuclear visualization and analyzed by terminal deoxynucleotidyl transferase dUTP nick end labeling (TUNEL) to visualize apoptotic cells. Treatment with dasatinib plus quercetin induced apoptosis in the senescent preadipocyte cells but not the non-senescent preadipocyte cells. The data are presented in FIG. 10B-G.

Example 8

Figure 11:
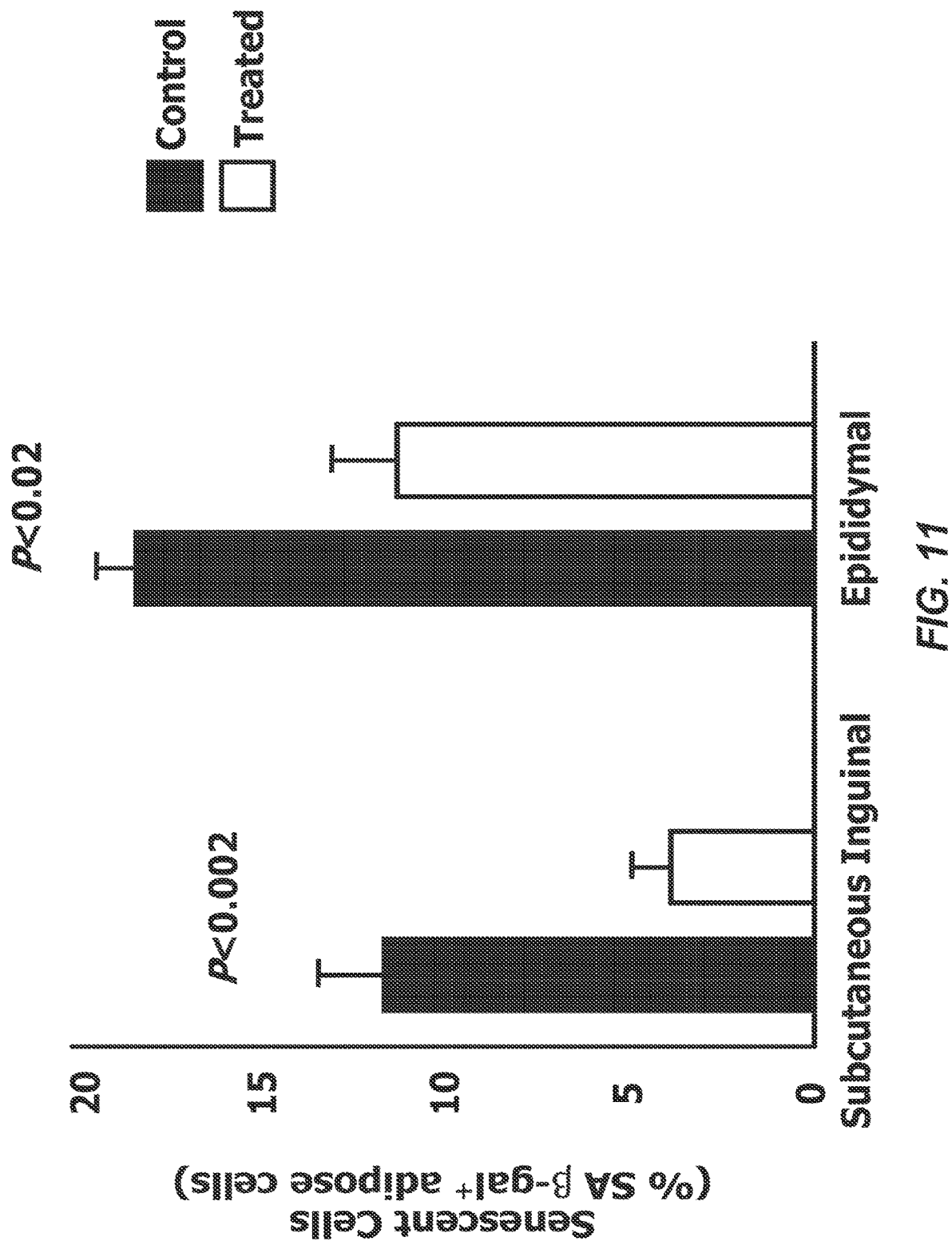
FIG. 11 depicts the level of senescent cells present in inguinal and epididymal adipose tissue of old (26 month) male mice. Animals were given a single dose of the senolytic combination dasatinib and quercetin (solid bars) or vehicle (open bars) by oral gavage 4 days before analysis (means+SEM; N=5; ANOVA). Senescent cells were detected by staining with SA-β-gal.

Dasatinib and Quercetin Treatment Decreases Presence of Senescent Cells in Adipose Tissue Old male mice (26 month) (n=5) were given a single dose of the combination, dasatinib (5 mg/kg) and quercetin (50 mg/kg), or vehicle by oral gavage. Four days after treatment, inguinal and epididymal adipose tissue were obtained from the animals. Senescent cells were detected by staining with SA-β-gal. Data are presented as means±SEM; n=5; ANOVA. The data are shown in FIG. 11. The extent to which the combination caused removal of senescent cells varied among adipose depots.

Example 9

Figure 12:
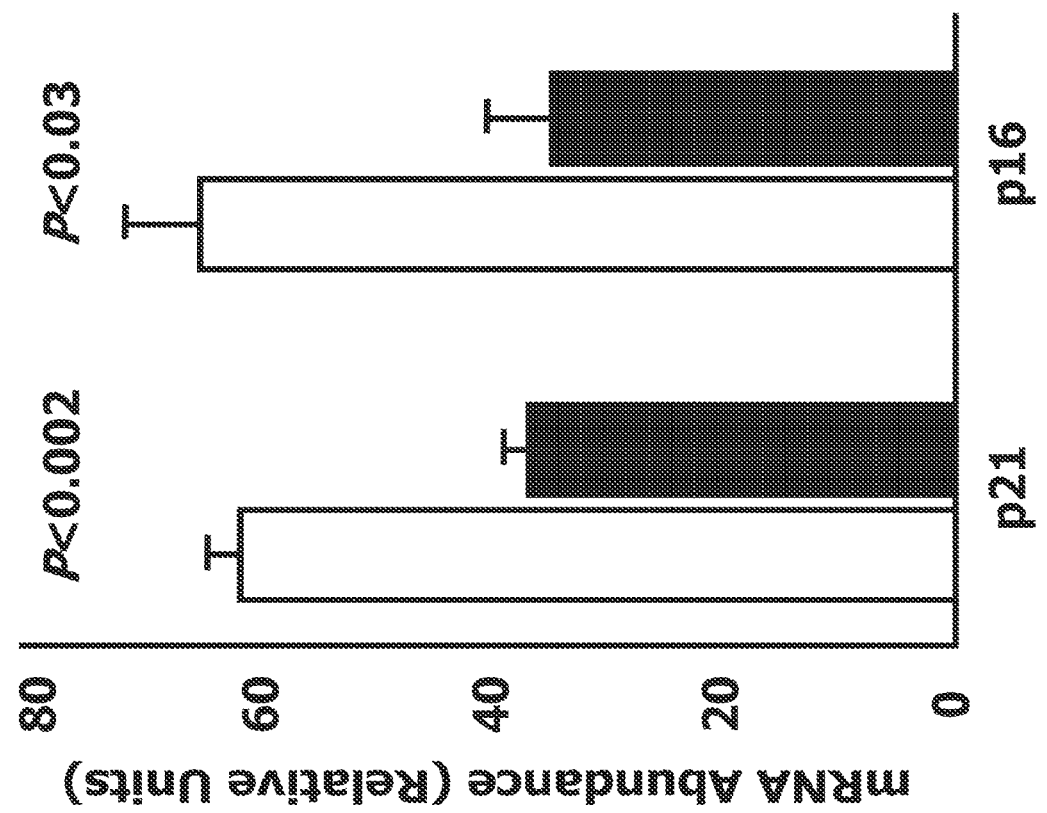
FIG. 12 shows the level of mRNA of senescent cell markers p16 and p21 in legs of mice exposed to 10 Gy collimated cesium radiation. Mice were treated once with the combination, dasatinib and quercetin, or vehicle. After 4 days, the levels of p21 and p16 mRNA were assayed by RT-PCR in muscle tissue from the radiated leg (N=5; T tests).

Reduction of Senescence Markers in Animals by Dasatinib and Quercetin Combination Treatment One leg of mice that were exposed to 10 Gy collimated cesium radiation two months. Two months after exposure, the animals developed grey hair and senescent cell accumulation in the radiated leg. Mice were treated once with the combination, dasatinib and quercetin, or vehicle. After 4 days, the level of p21 and p16 mRNA was assayed by RT-PCR in muscle tissue from the radiated leg (N=5; T tests). The senolytic combination resulted in a decrease muscle p16 and p21 in legs of radiation-exposed mice. p16 and p21 are senescent cell markers. The results are presented in FIG. 12.

Example 10

Figure 13:
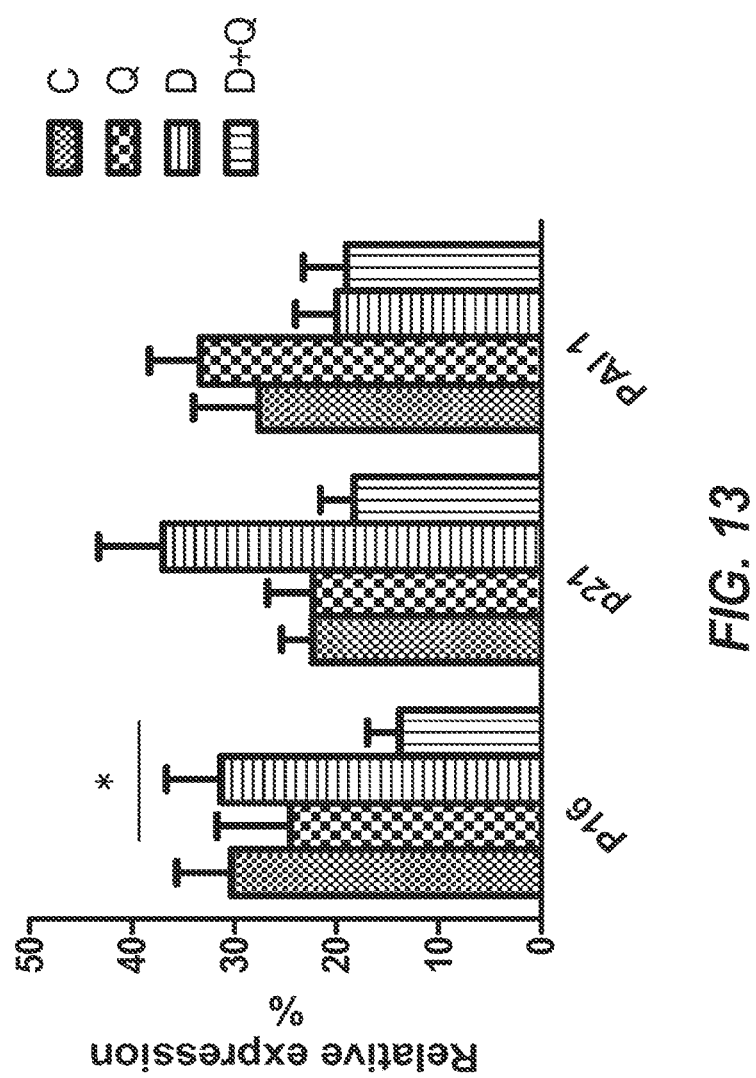
FIG. 13 illustrates mRNA expression of senescence markers (p16, p21, PAI-1) in inguinal fat of 24-month old male mice treated with a single dose of vehicle, quercetin, dasatinib, or combination of quercetin and dasatinib. The level of mRNA was assayed by RT-PCR in inguinal adipose tissue obtained five days after treatment. (p=0.049; Kruskal-Wallis Test, non-parametric ANOVA; n=8)

Reduction of Senescence Markers in Animals by Dasatinib and Quercetin Combination Treatment The level of mRNA expression of senescence markers (p16, p21, PAI-1) in inguinal fat of 24-month old male mice treated with a single dose of vehicle, quercetin (50 mg/kg), dasatinib (5 mg/kg), or combination of quercetin (50 mg/kg) and dasatinib (5 mg/kg) was determined. mRNA was assayed by RT-PCR in inguinal adipose tissue obtained five days after treatment. Kruskal-Wallis Test, non-parametric ANOVA; n=8. As shown in FIG. 13, the combination of quercetin and dasatinib reduced expression of p16 (p=0.049).

Figure 14A:
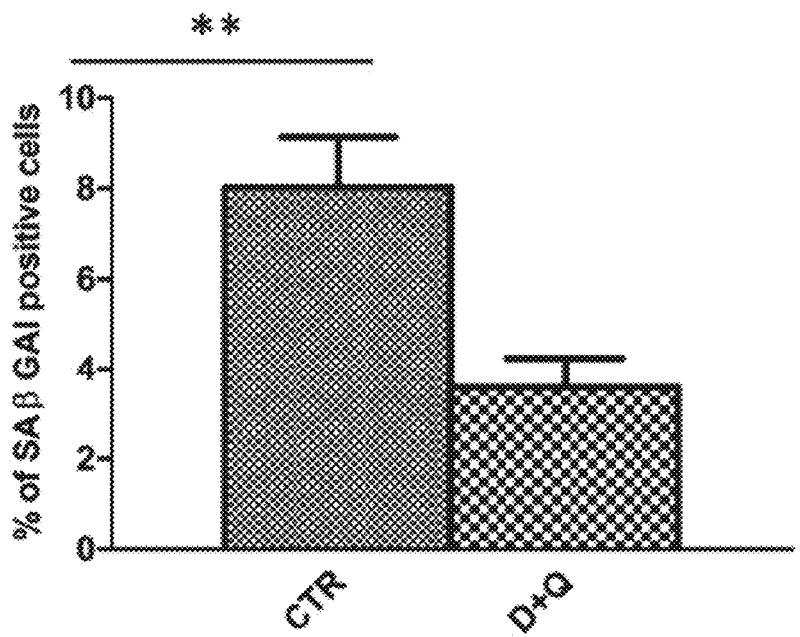
FIGS. 14A and 14B illustrate the percent positive SA-β-gal staining and p16 mRNA level in mice (n=14) treated with a single dose of vehicle or combination of quercetin and dasatinib. Five days after treatment, samples of inguinal fat were obtained and stained with the SA-β-gal (FIG. 14A) or analyzed for p16 mRNA expression by RT-PCR (FIG. 14 B). The data were analyzed by the Mann-Whitney test. SA-β-gal staining: p<0.0012; p16 mRNA expression: P<0.01
Figure 14B:
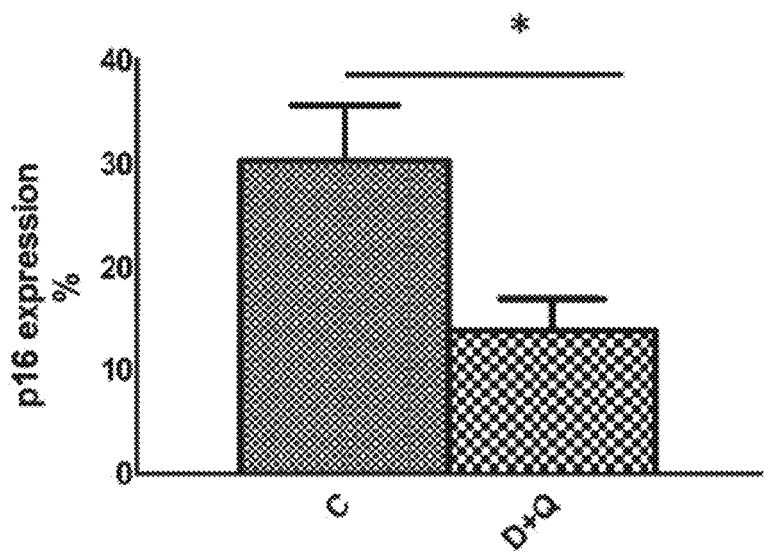

In a second experiment, groups of 24 month old mice (n=14) were treated with a single dose of vehicle or combination of quercetin and dasatinib. Five days after treatment, samples of inguinal fat were obtained and stained with the SA-β-gal or analyzed for p16 mRNA expression by RT-PCR. The results are presented in FIGS. 14A and B. The data were analyzed by the Mann-Whitney test. SA-β-gal staining: p<0.0012; p16 mRNA expression: P<0.01

Example 11

Effect Of Dasatinib and Quercetin Combination Treatment on Presence of Senescent Cells in Fat Tissue of Progeroid Mice BubR$^{H/H}$ mice have accelerated development of aging-like phenotypes. Four days after receiving 3 daily doses of the combination of dasatinib and quercetin (D+Q), SA-β-gal activity was lower in paraovarian and inguinal fat of older (8 months old–10-12 month is maximum lifespan in these mice) female BubR$^{H/H}$ mice vs. vehicle-treated controls. In these mice, inguinal fat on one side was biopsied 10 days before D+Q was given and analyzed at autopsy 4 days after. Levels of mRNA were determined by RT-PCR. p16 mRNA was decreased by D+Q (0.49+0.17 fold vs. baseline [=1]; P=0.07), as were p21 (0.37+0.15 fold; P<0.03); PAI-1 (0.37+0.01; P<0.00001), and IGFBP2 (0.30+0.15; P<0.02). In vehicle-treated mice, p16, p21, PAI-1, and IGFBP2 were not significantly lower vs. baseline (1.24+0.14, 1.25+0.41, 1.16+0.12, and 1.09+0.13, respectively; all p=NS).

Example 12

Cellular Senescence Increases in Diet-Induced Obese (D10) Mice

Figure 15:
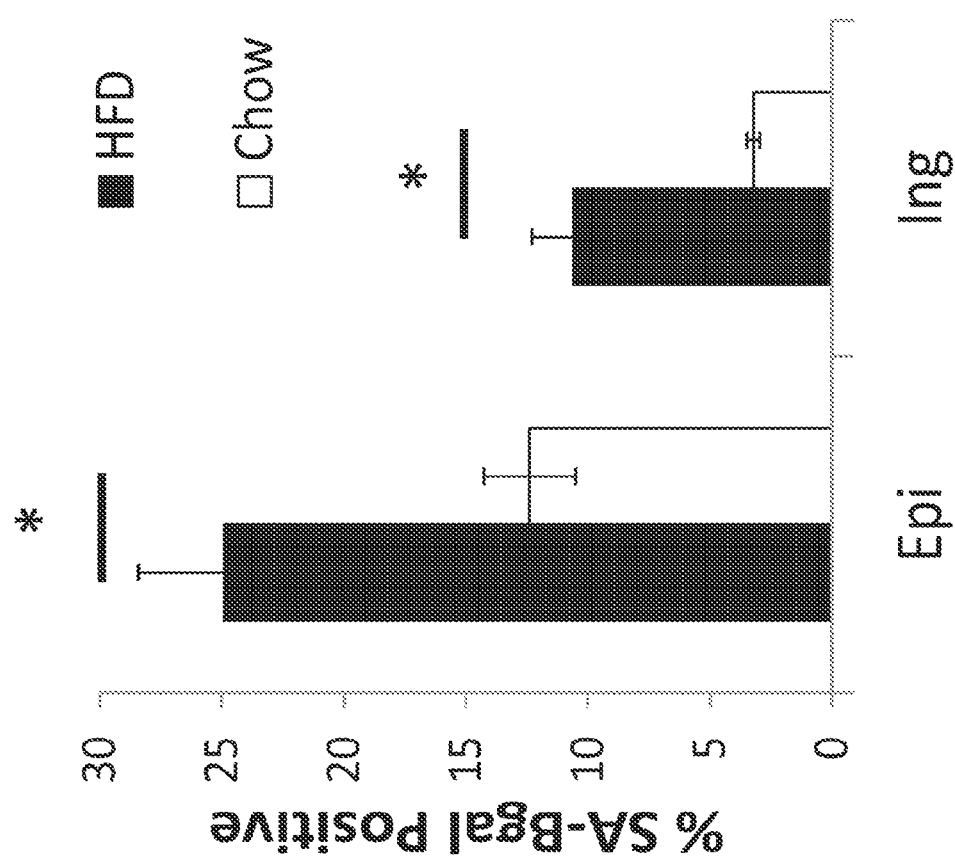
FIG. 15 illustrates the level of SA-β-gal positive cells in mice fed a high fat diet (HFD) vs. chow diet (Chow) for 4 month. Adipose tissue (inguinal (Ing) and epididymal (Epi) was stained for SA-13-gal.

An increased senescent cell burden was found in obese compared to lean, age-matched controls. Mice were fed a high fat vs. chow diet for 4 month. Adipose tissue (inguinal and epididymal) was stained for SA-β-gal. FIG. 15 shows that a higher burden of senescent cells are present in high-fat fed, obese animals than chow-fed controls.

Example 13

High Fat Feeding-Induced Senescence Reduced by Ganciclovir yn P16-3MR Mice

Figure 16:
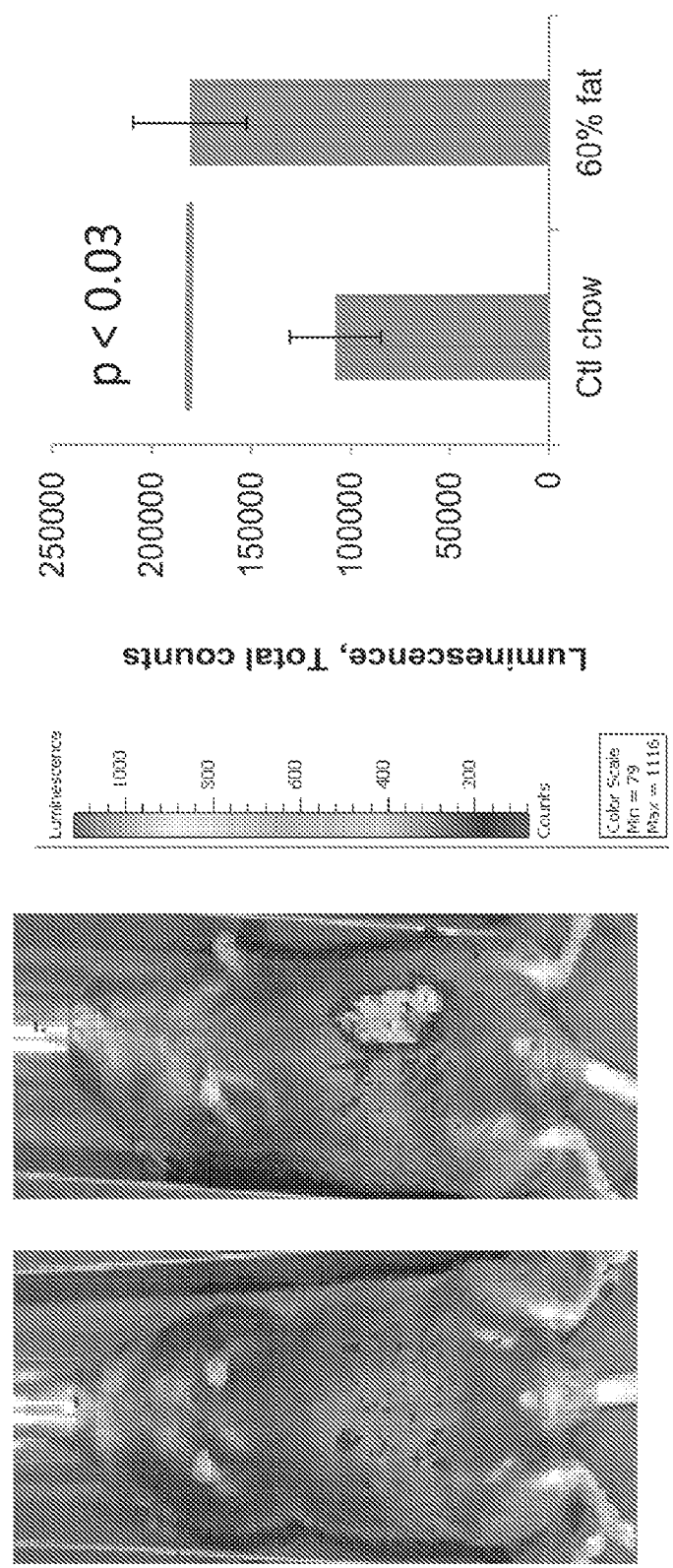
FIG. 16 shows that groups of p16-3MR mice (n=6) fed a high fat diet (high fat) for four months have increased numbers of senescence cells compared with mice fed a regular chow diet (chow fed) (n=6).

Groups of p16-3MR mice (n=6) were fed a high fat diet (60% fat) for four months mice or a regular chow diet. The presence of senescence cells was determined by measuring luminescence (i.e., p16 positive cells). As shown in FIG. 16, animals fed a high fat diet have increased numbers of senescence cells compared with the regular chow fed animals.

Figure 17:
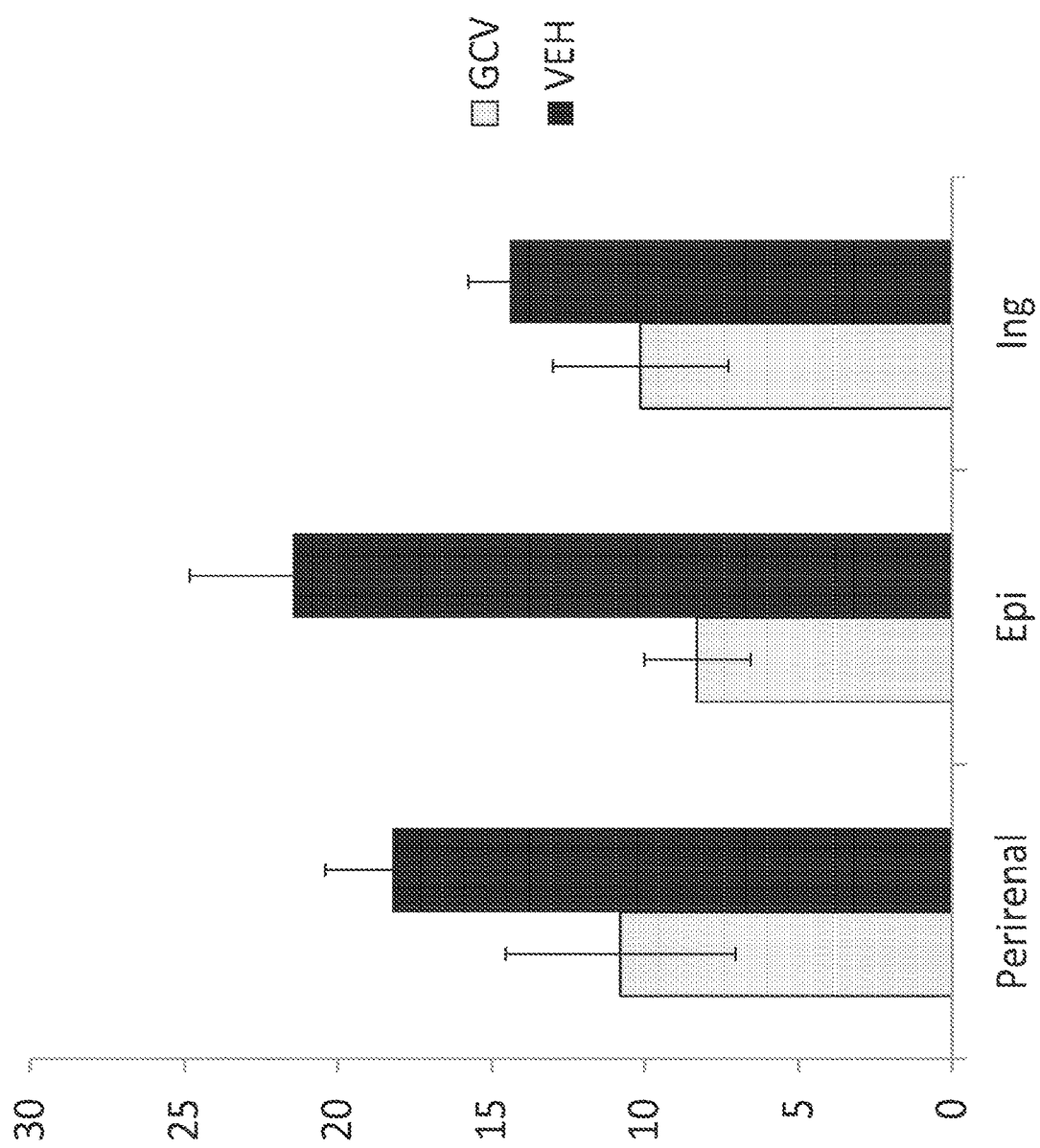
FIG. 17 illustrates decrease of senescent cells in adipose tissue of p16-3MR mice fed a high fat diet for four months and then treated with ganciclovir or vehicle. The presence of senescent cells in perirenal, epididymal (Epi), or subcutaneous inguinal (Ing) adipose tissue was detected by SA-β-Gal staining

Animals were then treated with ganciclovir or vehicle to determine if removal of senescent cells reduced the presence of senescent cells in adipose tissue. Groups of animals were treated with ganciclovir (GCV) or vehicle. Ganciclovir (25 mg/kg) was administered daily for five consecutive days. The presence of senescent cells in perirenal, epididymal, or subcutaneous inguinal adipose tissue was detected by SA-β-Gal staining Data were analyzed by ANOVA. The results are presented in FIG. 17. A significant reduction in presence of senescent cells was observed in epididymal fat. p=<0.004.

Example 14

Clearance of Senescent Cells Improves Glucose Tolerance and Insulin Sensitivity

Figure 18A:
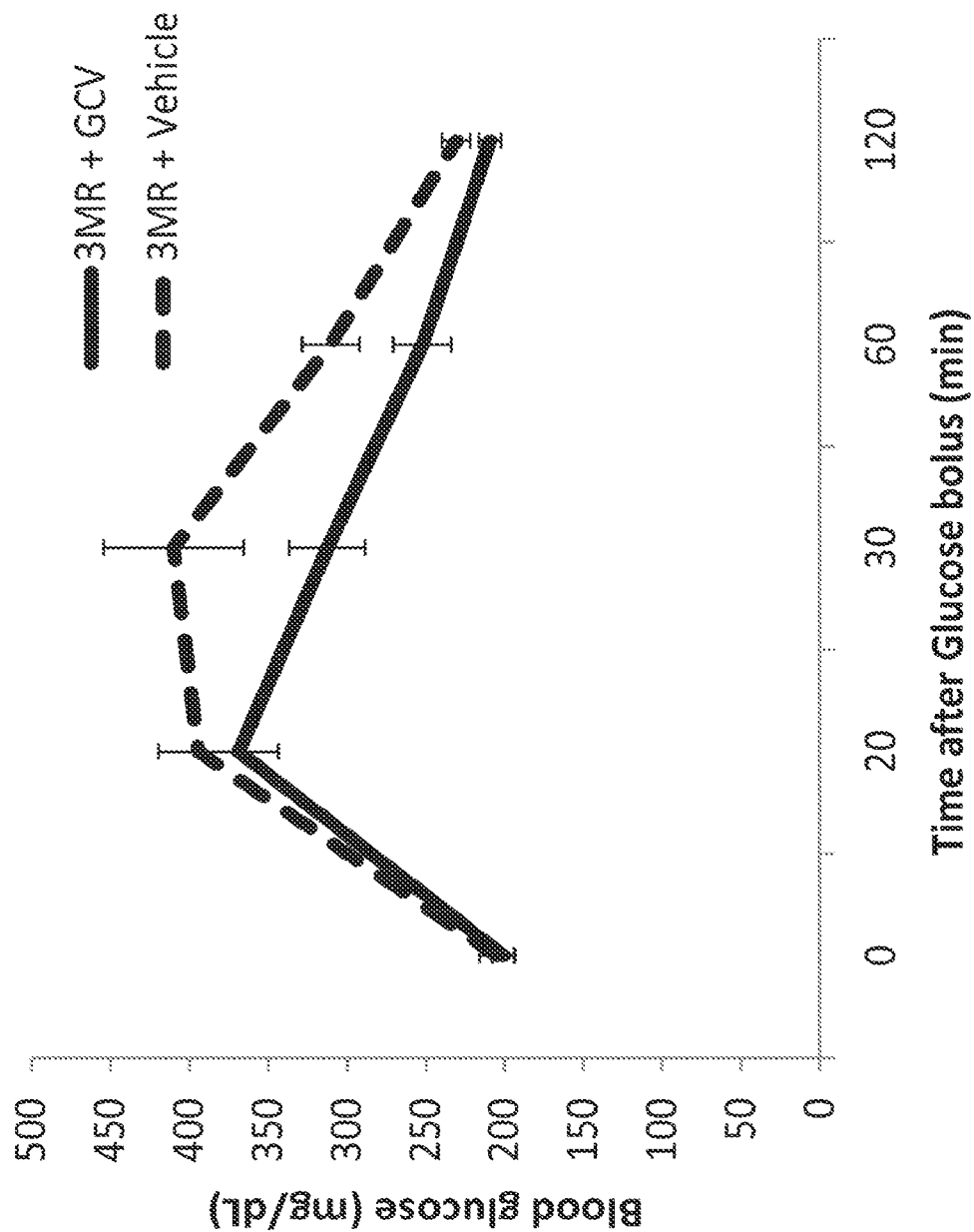
FIG. 18A-18C shows the effect of ganciclovir treatment on glucose tolerance in p16-3MR mice fed a high fat diet. A bolus of glucose was given at time zero, and blood glucose was monitored for up to 2 hours to determine efficacy of glucose disposal (FIG. 18A). This is quantified as area under the curve (AUC), with a higher AUC indicating glucose intolerance. The glucose tolerance test (GTT) AUC's of mice treated with ganciclovir is shown in FIG. 18B. Hemoglobin Alc is shown in FIG. 18C. n=9; ANOVA.
Figure 18B:
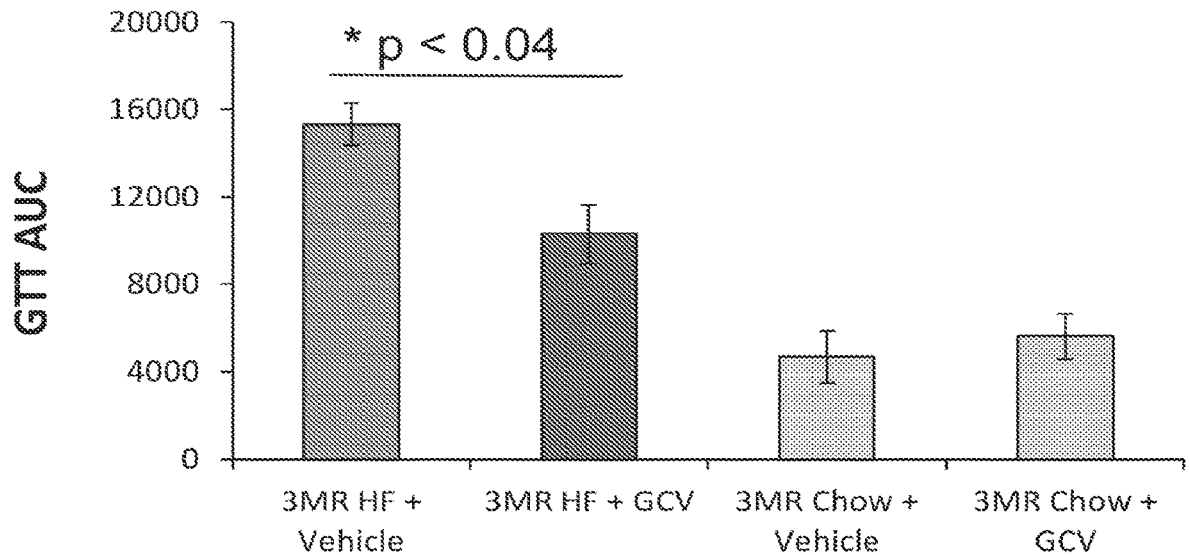
Figure 18C:
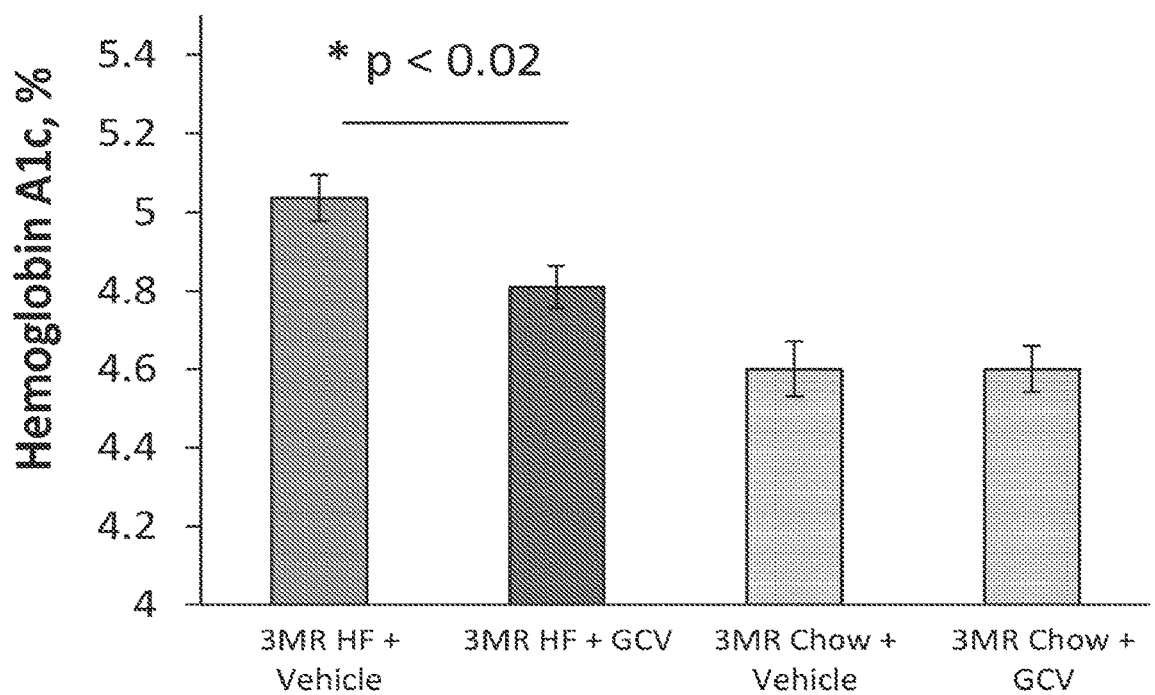

Groups of p16-3MR mice (n=9) were fed a high fat diet for four months mice or a regular chow diet. Animals were then treated with ganciclovir (3 rounds of 25 mg/kg ganciclovir administered daily for five consecutive days) or vehicle. A glucose bolus was given at time zero, and blood glucose was monitored at 20, 30, 60, and 120 minutes after delivering glucose to determine glucose disposal (see FIG. 18A). This was also quantified as "area under the curve" (AUC) (see FIGS. 18B and 18C), with a higher AUC value indicating glucose intolerance. AUCs of mice treated with ganciclovir were significantly lower than their vehicle-treated counterparts although not as low as chow-fed animals. Hemoglobin A1 c was lower in ganciclovir-treated mice (see FIG. 18C), suggesting that the animals' longer-term glucose handling was also improved.

Figure 19A:
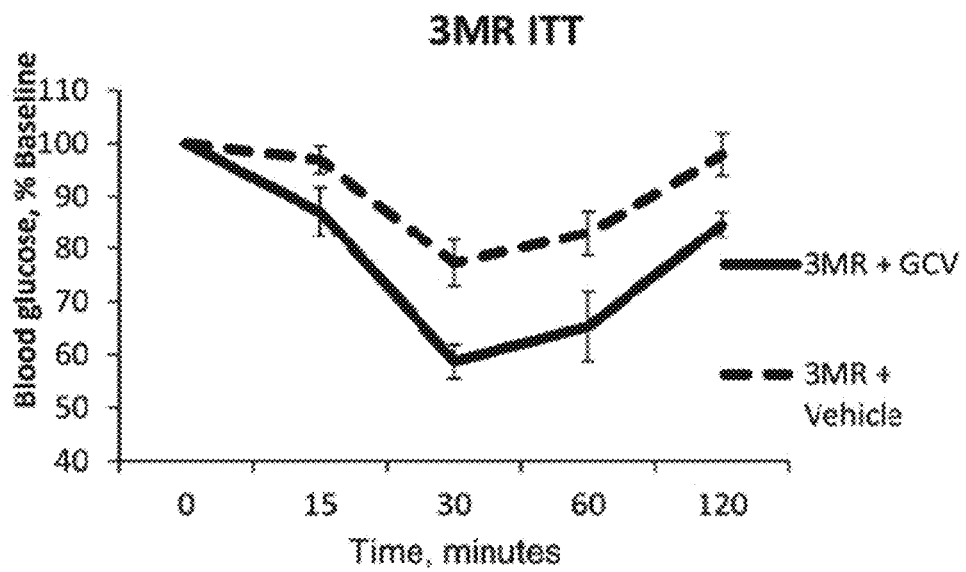
FIGS. 19A-19B show insulin sensitivity (Insulin Tolerance Testing (ITT)) of p16-3MR mice fed a high fat diet after ganciclovir administration. Blood glucose levels were measured at 0, 14, 30, 60, and 120 minutes after the administration of glucose bolus at time zero (see FIG. 19A). A change in insulin tolerance testing when ganciclovir was administered to wild-type mice was not observed (see FIG. 19B).
Figure 19B:
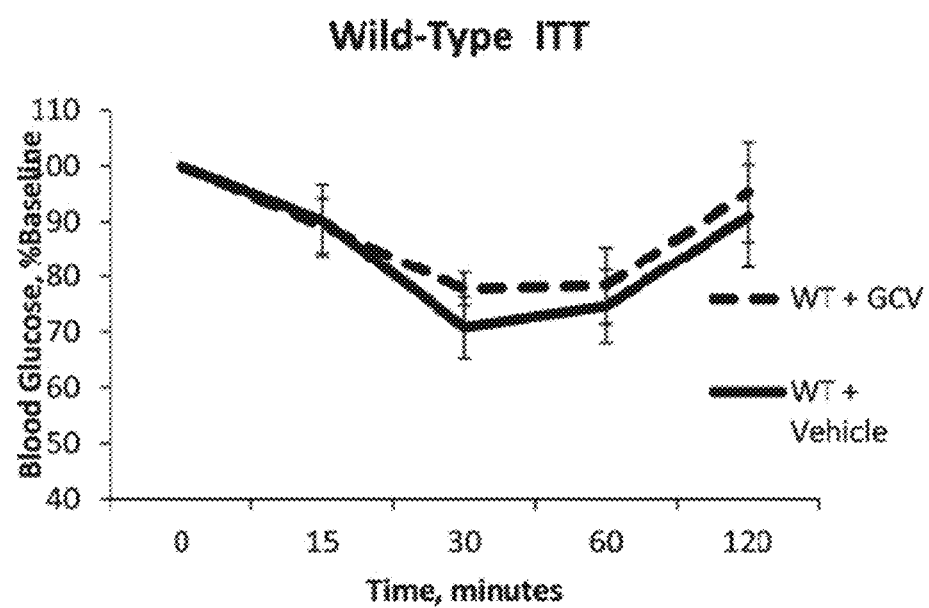

Insulin sensitivity was also determined (Insulin Tolerance Testing (ITT)). The results are presented in FIG. 19. Ganciclovir-treated mice showed a greater decrease in blood glucose at 0, 14, 30, 60, and 120 minutes after the administration of glucose bolus at time zero (see FIG. 19A), suggesting that senescent cell clearance improved insulin sensitivity. A change in insulin tolerance testing when ganciclovir was administered to wild-type mice was not observed (see FIG. 19B).

Changes in weight, body composition, and food intake were also monitored. Treatment by ganciclovir did not alter body weight, body composition monitored by measuring percent of fat, or food intake (measured in grams per week).

Example 15

Figure 20:
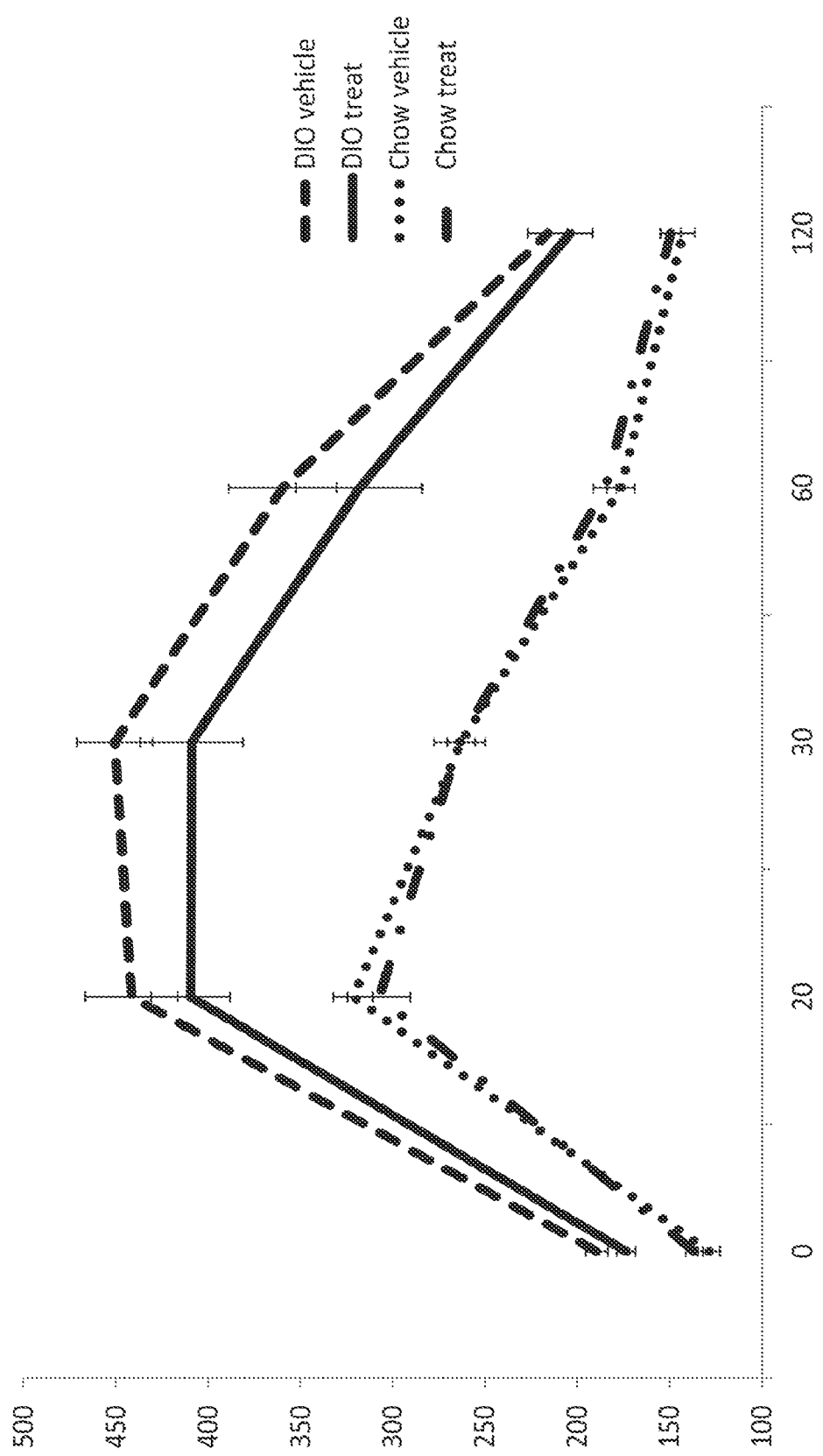
FIG. 20 illustrates results of glucose tolerance testing of wild-type diet-induced obese (DIO) mice treated with the combination of dasatinib and quercetin (DIO treat) or vehicle (DIO vehicle). Control non-obese animals were also treated with vehicle (Chow vehicle) or the combination (Chow treat).

Effect of Treatment with Dasatinib and Quercetin on Glucose Tolerance and Insulin Sensitivity The effect of treating wild-type diet-induced obese (DIO) mice with the combination of dasatinib and quercetin (D+Q) was determined. Glucose tolerance testing was performed. The results are presented in FIG. 20.

Example 16

Removal of Senescent Cells from DIO Mice Decreases Glucose Intolerance

Figure 21:
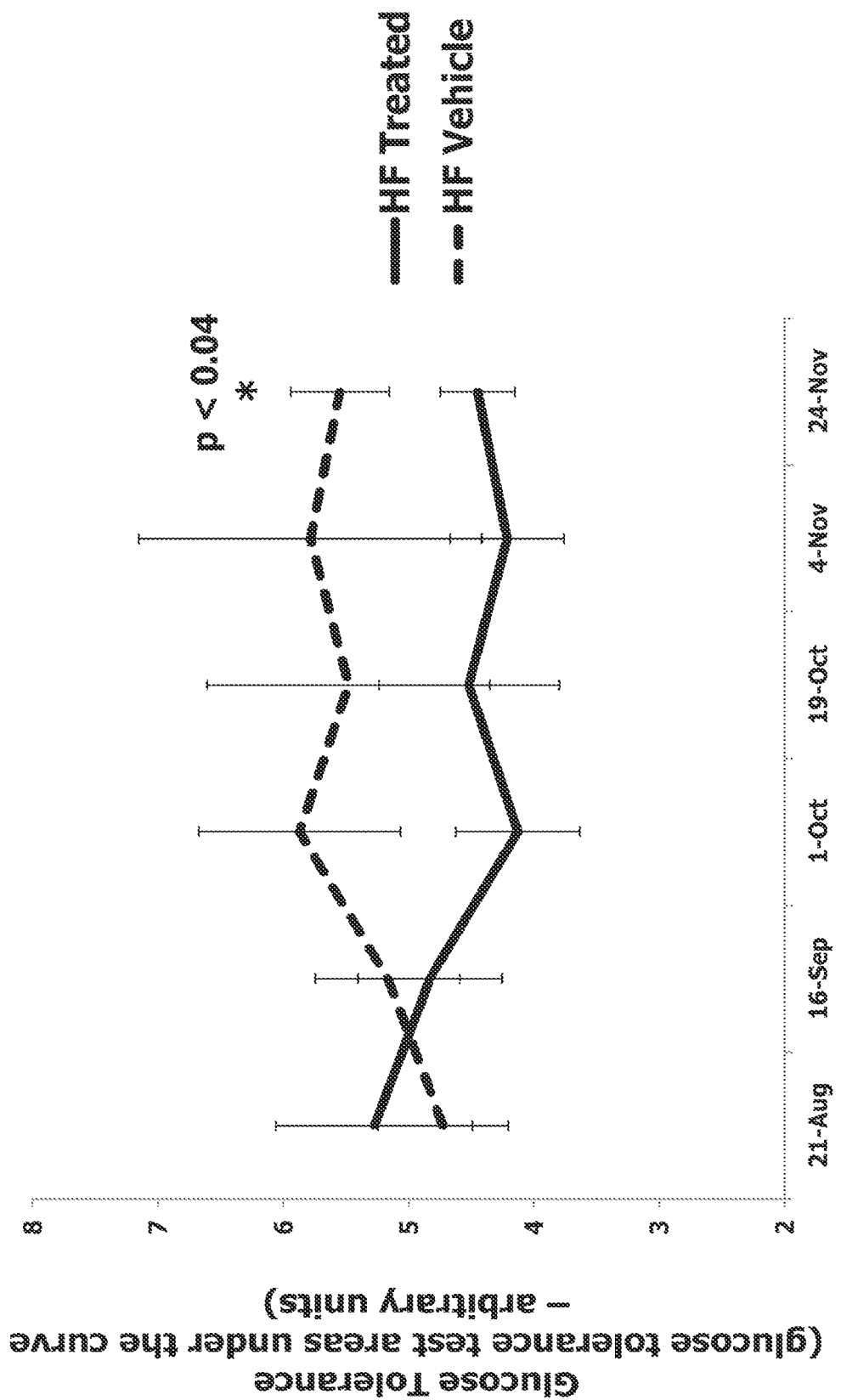
FIG. 21 depicts glucose tolerance testing results in diet-induced obese (DIO) mice. 3-month old INK-ATTAC,p16-3MR mice fed a high fat diet for 4 months and then treated with ganciclovir (HF Treated) or vehicle (HF Vehicle). DIO mice were treated with ganciclovir on September 1. Weights, fasting glucose levels, and areas under the curve in intraperitoneal glucose tolerance tests were higher in DIO mice than chow-fed controls, indicating glucose intolerance.

Three-month old INK-ATTAC,p16-3MR mice were fed a high fat diet for 4 months. The animals were then treated with ganciclovir or vehicle. DIO mice were treated with ganciclovir on September 1 (see FIG. 21). Glucose tolerance testing was performed, and the results are presented in FIG. 21. Weights, fasting glucose levels, and areas under the curve in intraperitoneal glucose tolerance tests were determined and were significantly higher in DIO mice than chow-fed controls, indicating glucose intolerance. Decreasing senescent cells in DIO mice by treating with ganciclovir led to sustained and improved glucose tolerance, as apparent from lower areas under the curve in glucose tolerance tests, compared to vehicle-treated DIO mice (lower vs. upper lines after 16-Sep, respectively).

Example 17

Treatment of DIO Mice with Dasatinib and Quercetin

Figure 22:
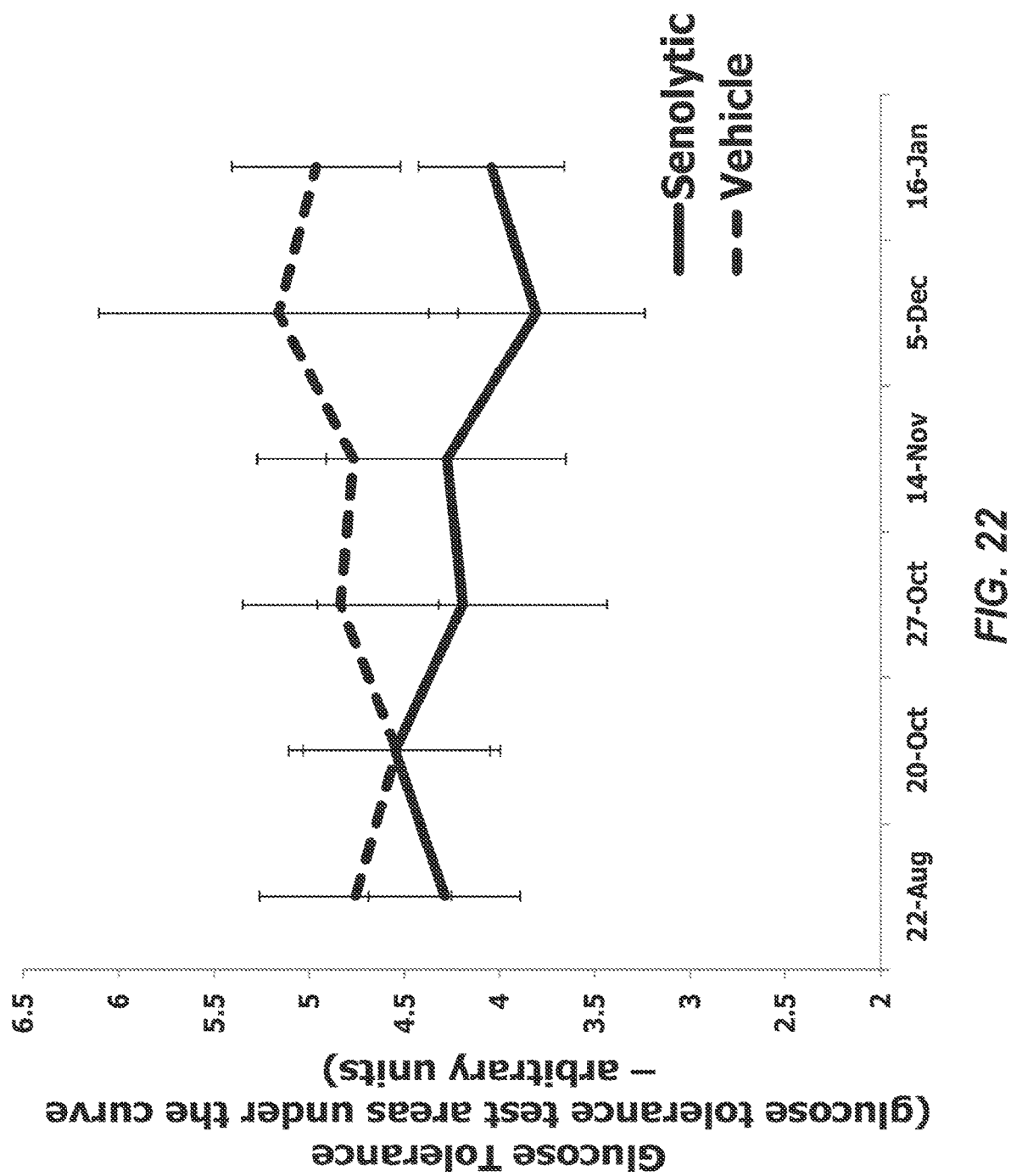
FIG. 22 illustrates glucose tolerance in animals. Groups of mice (n=10) were treated with a high fat diet for 4 months. Weights, fasting glucose levels, and areas under the curve in intra-peritoneal glucose tolerance tests were significantly higher in DIO than chow-fed controls. Animals received six doses of the combination of dasatinib and quercetin (D+Q) (Senolytic) or vehicle weekly. (P<0.01; ANOVA for repeated measures). Fasting glucose levels were lower in DIO mice after 6 doses of D+Q, each dose given weekly (P<0.05; N=10 mice/group; T test).

Diet-induced obese wild-type (DIO) mice were treated with the combination of dasatinib (5 mg/kg) and quercetin (50 mg/kg) (D+Q). Groups of mice (n=10) were treated with a high fat diet for 4 months. Weights, fasting glucose levels, and areas under the curve in intra-peritoneal glucose tolerance tests were significantly higher in DIO than chow-fed controls. Animals received six doses of D+Q weekly. The results are presented in FIG. 22. Treating with the combination D+Q once weekly led to improved glucose tolerance, as shown by lower areas under the curve in glucose tolerance tests compared to vehicle-treated DIO mice (lower vs. upper lines after 20-Oct, respectively; P<0.01; ANOVA for repeated measures). Fasting glucose levels were significantly lower in DIO mice after 6 doses of D+Q, each dose given weekly (P<0.05; N=10 mice/group; T test).

Figure 23A:
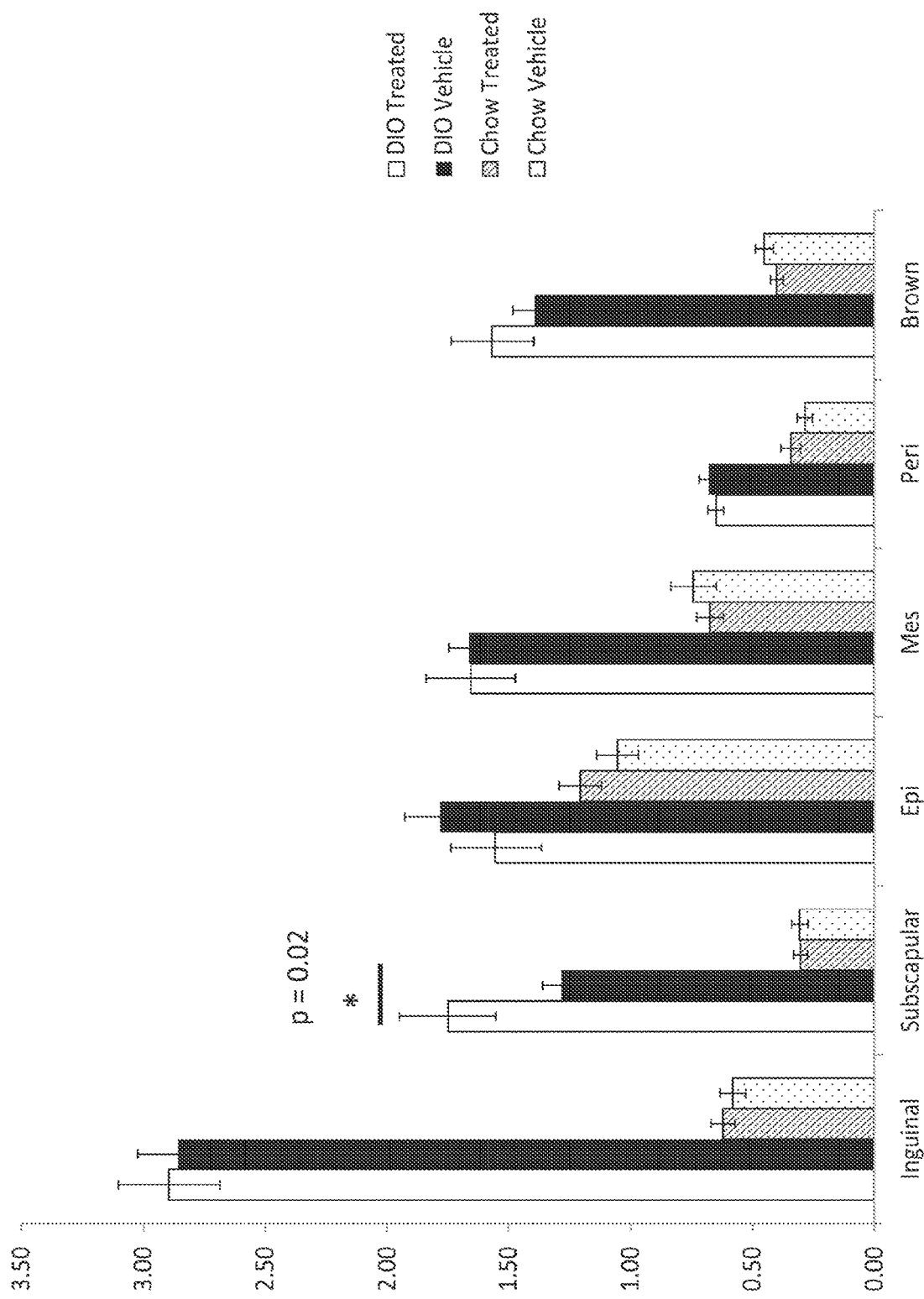
FIG. 23A-23B.
Figure 23B:
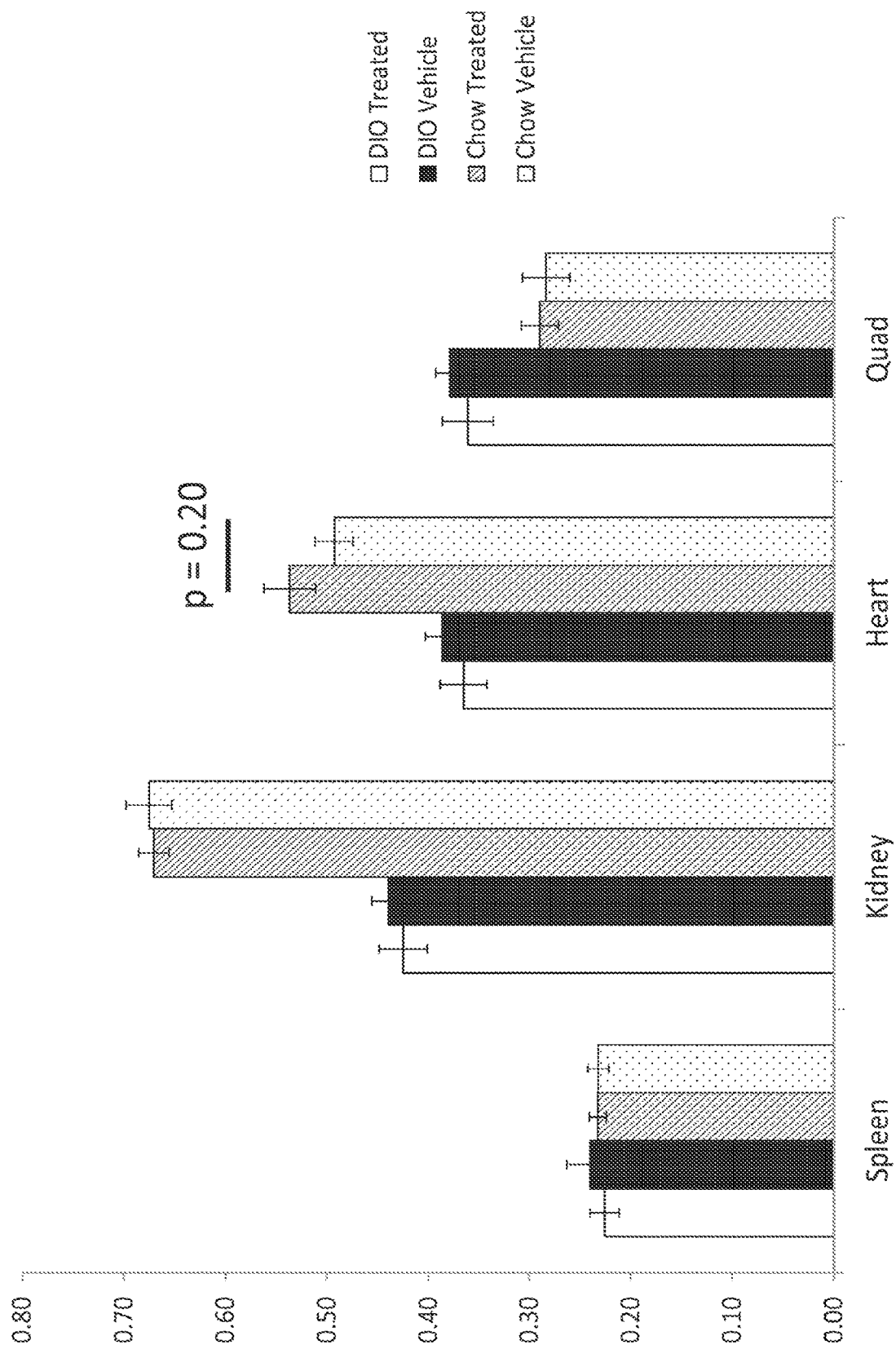

In a second experiment, diet-induced obese (DIO) mice treated with D+Q or vehicle. DIO mice were purchased from Jackson Laboratory at 8 weeks of age and maintained on a 60% fat (% cal.) diet throughout the study. Mice were treated with D+Q once per week (5 mg/kg D, 100 mg/kg Q) at 4 months of age. Mice were sacrificed after 28 weeks of treatment. Fat depot weights were measured at time of sacrifice and were expressed as percent of whole body weight. The results are presented in FIG. 23A. An increase in subscapular fat depot weight was seen in diet-induced obese (DIO) mice treated with D+Q (n=6) compared with vehicle-treated mice (n=10). No difference in chow-fed mice fat depot weights were seen between treatment and vehicle groups (n=9). Epididymal fat: p=0.34; Brown fat p=0.23. The weights of other organs obtained from the animals are shown FIG. 23B.

The various embodiments described above can be combined to provide further embodiments. All U.S. patents, U.S. patent application publications, U.S. patent applications, foreign patents, foreign patent applications and non-patent publications referred to in this specification and/or listed in the Application Data Sheet, including U.S. Provisional Patent Application No. 61/932,711 filed Jan. 28, 2014 and U.S. Provisional Patent Application No. 61/932,704 filed Jan. 28, 2014 are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A method for lessening symptoms of idiopathic pulmonary fibrosis in a subject in need thereof, comprising parenterally administering to the subject an effective amount of dasatinib and quercetin in a course of a daily dosing for a period of 1-7 days.

2. The method of claim 1, wherein the dasatinib and the quercetin is are administered in a repeated course of a period of 2-7 days every 0.5-12 months.

3. The method of claim 1, wherein the dasatinib and the quercetin are administered in a repeated course every 0.5-12 months.

* * * * *